United States Patent
Thompson et al.

(10) Patent No.: US 10,611,768 B2
(45) Date of Patent: Apr. 7, 2020

(54) P2X$_3$ AND/OR P2X$_{2/3}$ COMPOUNDS AND METHODS

(71) Applicant: Asana BioSciences, LLC, Lawrenceville, NJ (US)

(72) Inventors: Scott K. Thompson, Phoenixville, PA (US); Tony Priestley, West Chester, PA (US); Mrinalkanti Kundu, West Bengal (IN); Ashis Saha, Arlington, MA (US); Suvadeep Nath, Kolkata (IN)

(73) Assignee: Asana BioSciences, LLC, Lawrenceville, NJ (US)

( * ) Notice: Subject to any disclaimer, the term of this patent is extended or adjusted under 35 U.S.C. 154(b) by 0 days.

(21) Appl. No.: 16/205,553

(22) Filed: Nov. 30, 2018

(65) Prior Publication Data

US 2019/0092778 A1    Mar. 28, 2019

Related U.S. Application Data

(63) Continuation of application No. 15/717,185, filed on Sep. 27, 2017, now Pat. No. 10,174,039.

(60) Provisional application No. 62/402,280, filed on Sep. 30, 2016.

(51) Int. Cl.
| | | |
|---|---|---|
| C07D 487/04 | (2006.01) | |
| C07D 519/00 | (2006.01) | |
| A61P 25/00 | (2006.01) | |
| A61K 31/519 | (2006.01) | |

(52) U.S. Cl.
CPC ......... *C07D 487/04* (2013.01); *C07D 519/00* (2013.01)

(58) Field of Classification Search
CPC ..... C07D 487/04; C07D 519/00; A61P 25/00; A61P 31/519
See application file for complete search history.

(56) References Cited

U.S. PATENT DOCUMENTS

| | | | |
|---|---|---|---|
| 7,745,450 B2 | 6/2010 | Moravcova et al. | |
| 10,174,039 B2 * | 1/2019 | Thompson | C07D 487/04 |
| 2007/0039624 A1 * | 2/2007 | Roberts | A61J 7/04 |
| | | | 128/898 |
| 2007/0105877 A1 | 5/2007 | Bell et al. | |
| 2009/0182140 A1 | 7/2009 | Furukubo et al. | |
| 2011/0117055 A1 * | 5/2011 | MacDonald | A61K 31/167 |
| | | | 424/85.4 |
| 2012/0329780 A1 | 12/2012 | Thormann et al. | |
| 2015/0361078 A1 | 12/2015 | Buon et al. | |

FOREIGN PATENT DOCUMENTS

| | | | |
|---|---|---|---|
| JP | 2007055940 A * | 3/2007 | |
| WO | 2016/180380 A1 | 11/1916 | |
| WO | WO-2010118367 A2 * | 10/2010 | C07D 239/42 |

OTHER PUBLICATIONS

JP-2007055940-A (2007) ProQuest English Machine Translation Aug. 30, 2019: 1-37.*
Chen, J., Ch. 28 Pain. In: Pfaff, D.W. (ed.) 2013 Neuroscience in the 21st Century: From Basic to Clinical: 965-1023.*
Rumrich, I.K., Environmental Reduction Potential of Asthma Burden in Finland, University of Eastern Finland, 2014:1-115.*
International Search Report and Written Opinion from corresponding International Application No. PCT/US2017/053660; dated Feb. 13, 2018.
Database Registry, Chemical Abstracts Service, Columbus, OH, 2018, accession Nos. 1206144-97-9, 1206096-46-9 and 1206085-70-2; 1 page.
Vymetallova, L., "5-Substitued 3-isopropyl-7-[4-(2-pyridyl) benzyl] amino-1 (2) H-pyrazolo [4, 3-d] pyrimidines with anti-proliferative activity as potent and selective inhibitors of cyclin-dependent kinases", European Journal of Medicinal Chemistry, 110 (2016): 291-301.
International Preliminary Report on Patentability from counterpart International Application No. PCT/US2017/053660; dated Apr. 11, 2019.

* cited by examiner

*Primary Examiner* — John M Mauro
(74) *Attorney, Agent, or Firm* — DLA Piper LLP (US)

(57) ABSTRACT

The present disclosure provides novel compounds and methods for preparing and using these compounds. In one embodiment, the compounds are of the structure of formula (I), wherein $R^1$-$R^7$ are defined herein. In a further embodiment, these compounds are useful in method for regulating one or both of the P2X$_3$ or P2X$_{2/3}$ receptors. In another embodiment, these compounds are useful for treating pain in patients by administering one or more of the compounds to a patient. In another embodiment, these compounds are useful for treating respiratory dysfunction in patients by administering one or more of the compounds to a patient.

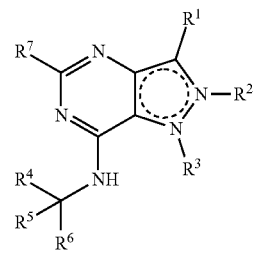

(I)

43 Claims, 1 Drawing Sheet

P2X$_3$ AND/OR P2X$_{2/3}$ COMPOUNDS AND METHODS

TECHNICAL FIELD

The present disclosure relates to compounds and methods for regulating activity of one or both of the P2X$_3$ or P2X$_{2/3}$ receptors.

BACKGROUND

Adenosine triphosphate (ATP) is well-recognized as the primary energy currency of living cells, but has also emerged as a significant signaling molecule that can shape physiological and pathophysiological processes by interacting with any of several 'purinergic' membrane-associated receptor molecules. The purinergic receptor family comprises both G-protein-coupled (GPCR) receptors (assigned a "P2Y" nomenclature) and ligand-gated ion channel or "P2X" variants.

ATP elicits an excitatory effect on afferent sensory nerves via an interaction with receptors of the P2X subfamily. The consequence of such hyperexcitability can be interpreted as pain when the ATP effect is elicited in skin, bone or visceral tissues, as pain and/or cough in airway tissues, or as pain and/or instability when it occurs in the bladder. See, e.g., Ford, *Purinergic Signalling*, 8 (Suppl 1), S3-S26, 2012 and Ford et al., *Frontiers in Cellular Neuroscience*, Volume 7, Article 267, 2013. Two particular receptor variants within the P2X subfamily, designated P2X$_3$ and P2X$_{2/3}$, have emerged as targets of particular interest in a variety of studies designed to measure nociception, airway or bladder function in rodents, since activation of these receptors by ATP is capable of generating the adverse events cited above. Agents which target P2X subfamily receptors would therefore have therapeutic value in treating conditions associated with these receptors, for example pain, respiratory disorders or bladder dysfunction.

Accordingly, there is a need for more potent and selective P2X$_3$/P2X$_{2/3}$ modulators.

SUMMARY

In one embodiment, a compound of formula (I) is provided, wherein R$^1$-R$^7$ are as described herein, or a pharmaceutically acceptable salt thereof.

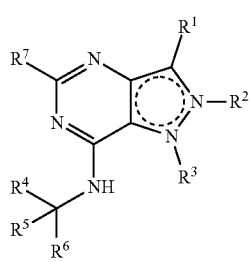

(I)

In another embodiment, the present disclosure provides a pharmaceutical composition comprising a compound of formula (I) and a pharmaceutically acceptable excipient.

In another embodiment, the present disclosure provides a kit comprising a compound of formula (I) or a pharmaceutical composition comprising a compound of formula (I).

In another embodiment, the present disclosure provides a method for regulating activity of one or both of the P2X$_3$ or P2X$_{2/3}$ receptors, comprising administering a compound of formula (I) to a subject in need thereof. In certain embodiments, regulating activity of one or both of the P2X$_3$ or P2X$_{2/3}$ receptors comprises inhibition of those receptors.

In another embodiment, the present disclosure provides a method for modulating one or both of the P2X$_3$ or P2X$_{2/3}$ pathways, comprising administering a compound of formula (I) to a patient.

In another embodiment, the present disclosure provides a method for treating pain in a subject, comprising administering to the subject a therapeutically effective amount of a compound of formula (I) or a pharmaceutical composition comprising a compound of formula (I).

In another embodiment, the present disclosure provides a method for treating a respiratory dysfunction in a subject, comprising administering to the subject a therapeutically effective amount of a compound of formula (I) or a pharmaceutical composition comprising a compound of formula (I). In some embodiments, the respiratory dysfunction is cough.

DETAILED DESCRIPTION

Figure 1A:
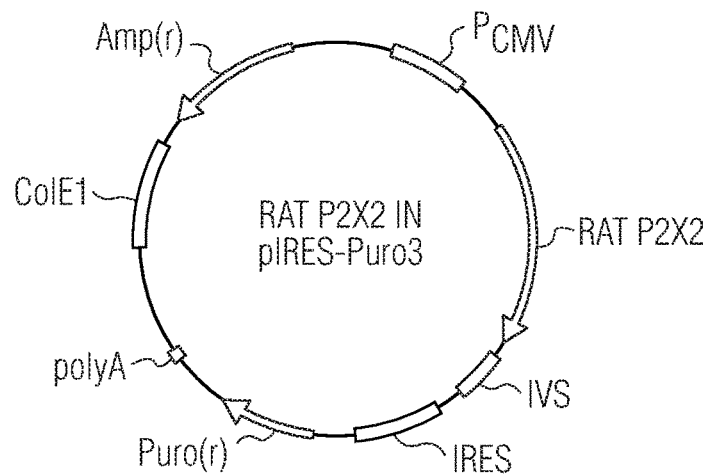
FIG. 1A is a map of a circular cloning plasmid pIRE-Spuro3 (Clontech Laboratories Inc., Mountain View, Calif.) into which the protein coding sequence of rat P2X2 has been cloned in the EcoRV-digested and dephosphorylated vector pIRES-puro3 within a multiple cloning site (MCS).

Discussed herein are novel compounds which can modulate the activity of one or both of the P2X$_3$ or P2X$_{2/3}$ pathways. These compounds can be used to treat any disease or disorder affected by a dysregulation of one or both of the P2X$_3$ or P2X$_{2/3}$ pathways.

The present disclosure thus provides compounds having the structure of formula (I), or prodrugs, enantiomers or pharmaceutically acceptable salts thereof:

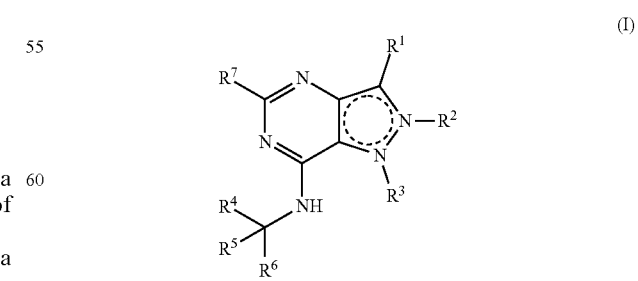

(I)

R$^1$ is H, halogen, C$_1$-C$_6$ alkyl, C$_3$-C$_6$ cycloalkyl, CN or CONH$_2$;

R$^2$ is none, C$_1$-C$_6$ alkyl or aryl;

$R^3$ is none, optionally substituted $C_1$-$C_6$ alkyl, $C_3$-$C_6$ cycloalkyl or heterocycle;

$R^4$ is optionally substituted heteroaryl, optionally substituted $C_1$-$C_6$ alkyl, optionally substituted $C_3$-$C_6$ cycloalkyl or optionally substituted aryl;

$R^5$, $R^6$ are independently H, $C_1$-$C_6$ alkyl or $C_3$-$C_6$ cycloalkyl; and $R^7$ is $CONHR^8$, optionally substituted heterocycle or optionally substituted heteroaryl, wherein $R_8$ is H, alkyl or cycloalkyl.

In some embodiments, the optional substituents for $R^3$, $R^4$ and $R^7$ are halogen, $C_1$-$C_6$ alkyl, $C_3$-$C_6$ cycloalkyl, $CONH_2$, $C_1$-$C_6$ alkoxy optionally substituted with halogen or $C_3$-$C_6$ cycloalkyl, heterocycle, heteroaryl or aryl optionally substituted with halogen or $C_3$-$C_6$ cycloalkyl.

In certain embodiments, compounds of formula (I) are provided wherein $R^1$ is H.

In certain embodiments, compounds of formula (I) are provided wherein $R^2$ is optionally substituted $C_1$-$C_6$ alkyl.

In certain embodiments, compounds of formula (I) are provided wherein $R^3$ is H.

In certain embodiments, compounds of formula (I) are provided wherein $R^1$ is halogen, $C_1$-$C_6$ alkyl, or CN.

In certain embodiments, compounds of formula (I) are provided wherein $R^7$ is $CONHR^8$, wherein $R^8$ is H, alkyl or cycloalkyl. In some embodiments, $R^8$ is cyclopropyl.

In certain embodiments, compounds of formula (I) are provided wherein $R^7$ is an optionally substituted morpholine or piperazine, for example

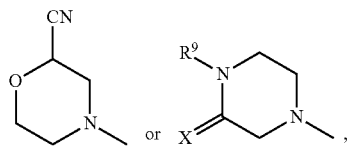

wherein X is O or H, H; and $R^9$ is H, optionally substituted $C_1$-$C_6$ alkyl, $CO(C_1$-$C_6$ alkyl$)$, $CONH_2$, $C(NH)NH_2$, $C(N\!\!-\!\!CN)NH_2$ or $SO_2NH_2$.

In certain embodiments, compounds of formula (I) are provided wherein $R^7$ is an optionally substituted heteroaryl selected from the group consisting of pyrazole, triazole, oxadiazole or pyridazine, for example:

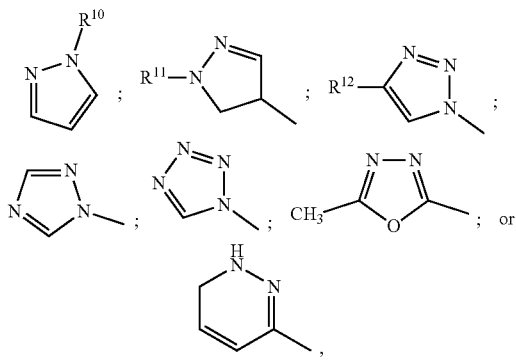

wherein $R^{10}$ is H or alkyl optionally substituted with —OH; $R^{11}$ is H, $CH_2$—$CONH_2$ or alkyl optionally substituted with —OH or halogen; and $R^{12}$ is H or $CONH_2$.

In certain embodiments, compounds of formula (I) are provided wherein $R^9$ is $CO(C_1$-$C_6$ alkyl$)$ or $CONH_2$.

In certain embodiments, compounds of formula (I) are provided wherein $R^4$ is optionally substituted heteroaryl.

In certain embodiments, compounds of formula (I) are provided wherein $R^4$ is optionally substituted aryl.

In certain embodiments, compounds of formula (I) are provided wherein $R^1$ and $R^3$ are H.

In certain embodiments, compounds of formula (I) are provided wherein $R^5$ and $R^6$ are independently H or $C_1$-$C_6$ alkyl or $C_3$-$C_6$ cycloalkyl.

In certain embodiments, compounds of formula (I) are provided wherein $R^5$ and $R^6$ are independently H or $C_3$-$C_6$ cycloalkyl.

In certain embodiments, compounds of formula (I) are provided wherein $R^1$ and $R^3$ are H and $R^2$ is optionally substituted $C_1$-$C_6$ alkyl.

In certain embodiments, compounds of formula (I) are provided wherein $R^1$ and $R^3$ are H, $R^2$ is optionally substituted $C_1$-$C_6$ alkyl and $R^4$ is optionally substituted heteroaryl.

In certain embodiments, compounds of formula (I) are provided wherein $R^1$ and $R^3$ are H, $R^2$ is optionally substituted $C_1$-$C_6$ alkyl, $R^4$ is optionally substituted heteroaryl, $R^5$ and $R^6$ are independently H or $C_1$-$C_6$ alkyl or are independently H and $C_3$-$C_6$ cycloalkyl, $R^7$ is

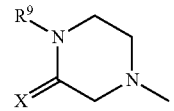

wherein X is H, H and $R^9$ is $CONH_2$.

In certain embodiments, compounds of formula (I) are provided wherein $R^4$ is an optionally substituted heteroaryl selected from the group consisting of quinoline, benzofuran, pyridine, benzothiophene, imidazopyridine and indazole.

Representative "pharmaceutically acceptable salts" of compounds of formula (I) include, for example, those of an acid or base. In one embodiment, the pharmaceutically acceptable salt is selected from among water-soluble and water-insoluble salts. The pharmaceutically acceptable salt can be of an acid selected from, e.g., among acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. The pharmaceutically acceptable salt can also be of a base selected from, e.g., sodium, potassium, calcium, and ammonium. In some embodiments, a composition, including a pharmaceutical composition, of the present disclosure can contain both a pharmaceutically acceptable salt and the free base form of a compound of formula (I).

Compounds of formula (I) can also comprise a prodrug of formula (I). Prodrugs of compounds of formula (I) can be prepared using various methods known to those skilled in the art. See, e.g., Rautio, Nature Reviews Drug Discovery, 7:255-270 (2008) and Ettcaner, J. Med. Chem., 47:2393-2404 (2004), which are hereby incorporated by reference. In the case of drugs containing a hydroxy or carbonyl moiety, acetyl and other ester analogs are contemplated for use as prodrugs. See, e.g., Beaumont, Current Drug Metabolism, 4:461-485 (2003), which is hereby incorporated by reference. In the case of drugs containing an amine moiety, prodrugs containing amides and carbamates are contemplated. See, e.g., Simplício, Molecules, 13:519-547 (2008), which is hereby incorporated by reference. As specific examples, (alkoxycarbonyloxy)alkyl carbamates, (acyloxy) alkyl carbamates, and (oxodioxolenyl)alkyl carbamates can be utilized as effective prodrug strategies for amines. See, e.g., Li, Bioorg. Med. Chem. Lett., 7:2909-2912 (1997); Alexander, J. Med. Chem., 34:78-81 (1991); Alexander, J. Med. Chem., 31:318-322 (1988); and Alexander, J. Med. Chem., 39:480-486 (1996), all of which are incorporated by reference herein.

Some compounds of formula (I) possess one or more chiral centers. Therefore, the disclosure of each compound includes its separate enantiomers as well as mixtures of the enantiomers (e.g., racemates). Where multiple chiral centers exist in compounds of formula (I), also provided are each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. Given the teachings herein, one of ordinary skill in the art could readily prepare optically active forms of compounds of formula (I), such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein is determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that can be straight or branched. In one embodiment, an alkyl contains 1 to 6 (inclusive) carbon atoms. In another embodiment, an alkyl contains 1 to 5 (inclusive) carbon atoms. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, for example, methyl, ethyl, propyl, butyl, pentyl, and hexyl, where all isomers of these examples are contemplated.

"Cycloalkyl" refers to carbocyclic rings that include, for example, cyclopropyl, cyclobutyl, cyclopentyl, cyclohexyl, and the like. In one embodiment, the carbocyclic ring is 3- to 6-membered. In another embodiment, the carbocyclic ring is a 3- to 5-membered ring. In a further embodiment, the carbocyclic ring is 4- to 6-membered. In still a further embodiment, the carbocyclic ring is 3- or 4-membered, i.e., cyclopropyl or cyclobutyl. Unless specifically noted, the alkyl groups are unsubstituted, i.e., they contain carbon and hydrogen atoms only. However, when the alkyl group or carbocyclic ring is substituted, it is prefaced with the term "optionally substituted" or "substituted". The optional substituents of the alkyl groups or carbocyclic rings can include, for example, halogen, CN, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy, heterocyclyloxy, aryl, heterocycle, heteroaryl, C(O)($C_1$ to $C_6$ alkyl), C(O)(heterocycle), C(O)NH$_2$, C(O)NH($C_1$ to $C_6$ alkyl), C(O)N($C_1$ to $C_6$ alkyl) ($C_1$ to $C_6$ alkyl), NHC(O)($C_1$ to $C_6$ alkyl), NH$_2$, NH(aryl), N($C_1$ to $C_6$ alkyl)($C_1$ to $C_6$ alkyl), and NHC(O)NH$_2$.

"Alkoxy" refers to ∼O(alkyl), where the alkyl is unsubstituted or substituted and is defined above. In one embodiment, an alkoxy contains 1 to 6 (inclusive) carbon atoms or integers or ranges there between. In another embodiment, an alkoxy contains 1 to 5 (inclusive) carbon atoms or ranges therebetween. In a further embodiment, an alkoxy contains 1 to 4 (inclusive) carbon atoms. In still a further embodiment, an alkoxy contains 1 to 3 (inclusive) carbon atoms. In still a further embodiment, an alkoxy contains 1 or 2 carbon atoms. Examples of alkoxy include, for example, methoxy, ethoxy, propoxy, and butoxy. The alkyl radical of an alkoxy group can be unsubstituted or substituted as defined above for "alkyl".

"Aryl" refers to an aromatic hydrocarbon group containing carbon atoms. In one embodiment, the aryl contains 6 to 10 carbon atoms, i.e., 6-, 7-, 8-, 9- or 10-membered. In another embodiment, aryl is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be optionally substituted with one or more groups including, without limitation, halogen, NO$_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)NH$_2$, C(O)NH($C_1$ to $C_6$ alkyl), C(O)N($C_1$ to $C_6$ alkyl)($C_1$ to $C_6$ alkyl), SO$_2$($C_1$ to $C_6$ alkyl), SO$_2$($C_2$ to $C_6$ alkynyl), SO$_2$NH($C_1$ to $C_6$ alkyl), SO$_2$(heterocycle), NHSO$_2$($C_1$ to $C_6$ alkyl), N($C_1$ to $C_6$ alkyl) SO$_2$($C_1$ to $C_6$ alkyl), NH$_2$, NH(aryl) or NHC(O)NH$_2$.

"Halogen" refers to F, $C_1$, Br and I.

The term "heteroatom" refers to a sulfur, nitrogen, or oxygen atom. It will be apparent and understood by one of ordinary skill in the art that the chemical structures represented herein that contain heteroatoms may, in certain circumstances, have one or more bound hydrogens that are not shown. "Heteroaryl" refers to a monocyclic aromatic 5- or 6-membered ring containing one to four heteroatoms or heterogroups selected from —O—, —N—, —S—, —S(=O)—, —S(=O)$_2$, or —C(=O)—. In one embodiment, the heteroaryl contains 1 to 5 carbon atoms (inclusive) or integers or ranges therebetween. In another embodiment, the heteroaryl contains 2 to 5 carbon atoms (inclusive). In a further embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In a further embodiment, the bicyclic heteroaryl is a pyridine fused to a 5- or 6-membered monocyclic heteroaryl. In still a further embodiment, the heteroaryl ring has 1 or 2 nitrogen atoms in the ring. In still a further embodiment, the heteroaryl ring has 1 nitrogen atom and 1 oxygen atom. In still a further embodiment, the heteroaryl ring has 1 nitrogen atom and 1 sulfur atom. Examples of heteroaryl groups include, for example, furan, thiophene, indole, azaindole, oxazole, thiazole, isoxazole, isothiazole, imidazole, pyridine, pyridone, pyrazole, pyrimidine, pyrazine, pyridazine, pyrrole, oxadiazole such as 1,3,4-oxadiazole, triazole such as 1,2,4-triazole and 1,2,3-triazole, tetrazole, benzoxazole, benzothiazole, benzofuran, benzisoxazole, benzimidazole, azabenzimidazole, indazole, quinazoline, quinoline, isoquinoline, benzothiophene and imidazopyridine. A heteroaryl can be optionally substituted with one or more groups including, without limitation, halogen, CN, $NO_2$, $C_1$ to $C_6$ alkyl, OH, $C_1$ to $C_6$ alkoxy, $C_3$ to $C_8$ cycloalkyl, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, $C_1$ or $C_6$ alkyl containing 1 to 3 fluorine atoms, $C_1$ to $C_6$ alkoxy containing 1 to 3 fluorine atoms, $C_3$ to $C_6$ cycloalkyl-$C_1$ to $C_6$ alkyl, $C_1$ to $C_6$ hydroxyalkyl, heterocyclyloxy, $C_1$ to $C_6$ alkylthio, aryl, heterocycle, heteroaryl, $C(O)(C_1$ to $C_6$ alkyl), $C(O)$(heterocycle), $C(O)O(C_1$ to $C_6$ alkyl), $C(O)NH_2$, $C(O)NH(C_1$ to $C_6$ alkyl), $C(O)N(C_1$ to $C_6$ alkyl)($C_1$ to $C_6$ alkyl), $SO_2(C_1$ to $C_6$ alkyl), $SO_2(C_2$ to $C_6$ alkynyl), $SO_2NH(C_1$ to $C_6$ alkyl), $SO_2$(heterocycle), $NHC(O)(C_1$ to $C_6$ alkyl), $NHSO_2(C_1$ to $C_6$ alkyl), $N(C_1$ to $C_6$ alkyl)$SO_2(C_1$ to $C_6$ alkyl), $NH_2$, NH(aryl), $N(C_1$ to $C_6$ alkyl)($C_1$ to $C_6$ alkyl) and $NHC(O)NH_2$. In one embodiment, "heteroaryl" refers to 5-membered heteroaryl containing one to four heteroatoms selected from —O—, —N—, or —S—, which is unsubstituted or substituted with one or more halogen, $C_1$ to $C_6$ alkyl, $C_3$ to $C_6$ cycloalkyl, $C_3$ to $C_6$ cycloalkyl-$C_1$ to $C_6$ alkyl, $C_1$ to $C_6$ hydroxyalkyl, $C_1$ to $C_6$ alkoxy, $C_1$ to $C_6$ alkyl containing 1 to 3 fluorine atoms, or $CH_2CONH_2$. Non-limiting examples of 5-membered heteroaryl rings include, for example, oxadiazole, pyrazole, thiophene, isoxazole, imidazole, tetrazole, triazole, furan, pyrrole, thiazole, isothiazole, or thiadizole. Each of these 5-membered heteroaryl can be substituted with one or more halogen, $C_1$ to $C_6$ alkyl, $C_3$ to $C_6$ cycloalkyl, $C_3$ to $C_6$ cycloalkyl-$C_1$ to $C_6$ alkyl, $C_1$ to $C_6$ hydroxyalkyl, $C_1$ to $C_6$ alkoxy, $C_1$ to $C_6$ alkyl containing 1 to 3 fluorine atoms, or $CH_2CONH_2$.

"Heterocycle" refers to a monocyclic or bicyclic group having one to three heteroatoms or heterogroups selected from —O—, —N—, —S—, —S(=O)—, —S(=O)$_2$, or —C(=O)—. A heterocycle can be saturated or partially saturated. In one embodiment, the heterocycle contains 3 to 7 carbon atoms (inclusive) or integers or ranges therebetween. In another embodiment, the heterocycle contains 4 to 7 carbon atoms (inclusive). In a further embodiment, the heterocycle contains 4 to 6 carbon atoms (inclusive). In still a further embodiment, the heterocycle contains 5 or 6 carbon atoms (inclusive). Examples of heterocycles include, for example, to aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In still a further embodiment, the heterocycle contains 1 or 2 nitrogen atoms, 3 to 6 carbon atoms, and 1 oxygen atom. In a still further embodiment, the heterocycle is 5- to 8-membered. In still a further embodiment, the heterocycle is 5-membered. In a still further embodiment, the heterocycle is 6-membered. In still a further embodiment, the heterocycle is 8-membered. A heterocycle can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, heterocyclyloxy, $C_1$ to $C_6$ alkylthio, aryl, heterocycle, heteroaryl, $C(O)(C_1$ to $C_6$ alkyl), $C(O)$(heterocycle), $C(O)O(C_1$ to $C_6$ alkyl), $C(O)NH_2$, $C(O)NH(C_1$ to $C_6$ alkyl), $C(O)N(C_1$ to $C_6$ alkyl)($C_1$ to $C_6$ alkyl), $SO_2(C_1$ to $C_6$ alkyl), $SO_2(C_2$ to $C_6$ alkynyl), $SO_2NH(C_1$ to $C_6$ alkyl), $SO_2$(heterocycle), $NHC(O)(C_1$ to $C_6$ alkyl), $NHSO_2(C_1$ to $C_6$ alkyl), $N(C_1$ to $C_6$ alkyl)$SO_2(C_1$ to $C_6$ alkyl), $NH_2$, NH(aryl), $N(C_1$ to $C_6$ alkyl)($C_1$ to $C_6$ alkyl) and $NHC(O)NH_2$.

"Ester" refers to ∼C(O)O(alkyl), which is bound through the carbon atom. The alkyl group is defined and unsubstituted or substituted as described above. Examples of ester include, without limitation, $C(O)OCH_3$, $C(O)O(CH_2CH_3)$, $C(O)O(CH_2CH_2CH_3)$, and $C(O)(O)(CH_2CH_2CH_2CH_3)$.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

As used herein, the terms "subject" and "patient" are used interchangeably and include any animal such as a mammal, e.g., a human, mouse, rat, guinea pig, dog, cat, horse, cow, pig, or non-human primate, such as a monkey, chimpanzee, baboon or gorilla.

As used herein, the terms "disease", "disorder" and "condition" are used interchangeably, to indicate an abnormal state in a subject.

In one embodiment, the present disclosure provides a pharmaceutical composition comprising a compound of formula (I). Pharmaceutical compositions of the present disclosure as described herein can comprise a compound of formula (I) optionally with one or more pharmaceutically acceptable excipients. Pharmaceutical compositions of the present disclosure can also comprise a compound of formula (I) and one or more therapeutic agents, i.e., active ingredients, as described below. In a further embodiment, Pharmaceutical compositions of the present disclosure comprise a compound of formula (I), one or more pharmaceutically acceptable excipients and one or more therapeutic agents.

The pharmaceutical compositions of the present disclosure can comprise an amount of a compound of formula (I) that is effective for regulating the $P2X_3$ or $P2X_{2/3}$ pathways, for example to achieve a therapeutic effect, such as the treatment of pain and/or respiratory dysfunctions in a subject. The amount of a compound of formula (I) administered to a subject (either alone or comprising a pharmaceutical composition) which is effective for regulating the P2X$_3$ or P2X$_{2/3}$ pathways to achieve a therapeutic effect is a "therapeutically effective amount."

In some embodiments, the therapeutically effective amount of the compounds of formula (I) will depend on factors such as the formulation, pharmacological potency of the drug, age, weight and sex of the patient, condition being treated, disease penetration and/or severity of the patient's symptoms, specific compounds of formula (I), route of delivery, and response pattern of the patient. It is also contemplated that the treatment and dosage of the compounds of formula (I) can be administered in a dosage form, and that one skilled in the art can adjust the dosage form accordingly to reflect the relative level of activity needed or desired to administer a therapeutically effective amount. The particular dosage to be employed (and also, for example, the number of times to be administered per day) to administer a therapeutically effective amount can be readily determined by an ordinarily-skilled physician, and can be varied, for example, by titration of the dosage to the particular circumstances in order to produce a desired therapeutic effect. Further, the ordinarily-skilled physician can readily calculate any changes needed or desired in the amounts of any one of the compounds of formula (I) to administer a therapeutically effective amount; for example, changes in components or dilutions of compounds or pharmaceutical compositions of the present disclosure. In one embodiment, the compounds or compositions can be diluted about 2-fold, 4-fold, or 8-fold prior to administration to a subject.

In one embodiment, the present disclosure provides a method of treating pain in a subject, comprising administering to the subject a therapeutically effective amount of a compound of formula (I) (either alone or comprising a pharmaceutical composition). For treating pain according to the present method, exemplary dosages to administer a therapeutically effective amount include the following: about 0.0001% to about 25% w/v (i.e., weight of drug per mL of formulation); less than about 20% w/v, about 15% w/v, about 10% w/v, about 5% w/v, or about 1% w/v; about 0.0001% to about 10% w/v; about 0.005 to about 5% w/v. In certain embodiments, a therapeutically effective amount of a compound of formula (I) is about 0.01 to about 5% w/v; about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, or about 5% w/v. In one embodiment, the therapeutically effective amount of a compound of formula (I) is about 0.2% w/v or about 0.5% w/v.

In some embodiments, the therapeutically effect amount of a compound of formula (I) administered to treat pain in a subject can be about 1 mg to about 1000 mg per dose based on a 70 kg mammalian, for example human, subject. In another embodiment, the therapeutically effective amount is about 2 mg to about 250 mg per dose or about 5 mg to about 100 mg per dose. In a further embodiment, the therapeutically effective amount is about 25 mg to 50 mg, about 20 mg, about 15 mg, about 10 mg, about 5 mg, about 1 mg, about 0.1 mg, about 0.01 mg or about 0.001 mg per dose.

In one embodiment, the present disclosure provides a method of treating respiratory dysfunctions in a subject, comprising administering to the subject a therapeutically effective amount of a compound of formula (I) (either alone or comprising a pharmaceutical composition). For treating of respiratory dysfunctions according to the present method, exemplary dosages to administer a therapeutically effective amount of a compound of formula (I) include the following: about 0.0001% to about 50% w/v (i.e., weight of drug per mL of formulation); about 0.5% to about 25% w/v; about 1% to about 20% w/v; or about 5% to 10% w/v. In a further embodiment, the therapeutically effective amount is about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, or about 5% w/v.

In some embodiments, the therapeutically effective amount of a compound of formula (I) administered to treat respiratory dysfunction in a subject can be about 0.001 mg to about 1,000 mg per dose based on a 70 kg mammalian, for example human. In one embodiment, a therapeutically effective amount is about 1 mg to about 250 mg per dose or about 5 mg to about 100 mg per dose. In some embodiments, a therapeutically effective amount of a compound of formula (I) comprises a dosage of about 0.1 mg, 1 mg, about 5 mg, about 10 mg, about 15 mg, about 20 mg, about 25 mg, about 50 mg, about 100 mg, about 200 mg, about 300 mg, about 400 mg, about 500 mg, about 600 mg, about 700 mg, about 800 mg, about 900 mg, about 1,000 mg per dose.

In methods of the present disclosure, a therapeutically effective amount of a compound of formula (I) can be administered (either alone or comprising a pharmaceutical composition) to a subject on regular schedule, i.e., on a daily, weekly, monthly, or yearly basis or on an irregular schedule with varying administration days, weeks, months, etc. Alternatively, the therapeutically effective amount can be administered in multiple doses, which can be divided equally or unequally. Each dose can constitute a therapeutically effective amount, or the total amount dosed can constitute a therapeutically effective amount. For example in one embodiment, the therapeutically effective amount for the first dose can be higher than the therapeutically effective amount for one or more of the subsequent doses. In another embodiment, the therapeutically effective amount for the first dose is lower than the therapeutically effective amount for one or more of the subsequent doses. Equally or unequally divided doses can be administered over various time periods including, for example, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy can be determined according to the judgment of an ordinarily-skilled physician. As mentioned above, the therapeutically effective amounts described herein can refer to each dose of a compound of formula (I) given, or can refer to the total amounts administered for a given time period; that is, if more than one compound of formula (I) is administered to a subject, the therapeutically effective amounts can correspond to the total amount administered. The duration of treatment can last for days, weeks, months or years. In some embodiments, treatment lasts for two weeks. In some embodiments, treatment lasts one month. In some embodiments, treatment can proceed indefinitely.

In methods of the present disclosure, a therapeutically effective amount of a compound of formula (I) can be administered (either alone or comprising a pharmaceutical composition) to a subject by any route, taking into consideration the specific condition being treated. Suitable routes of administration include orally, by injection, inhalation (including orally, intranasally and intratracheally), ocularly, transdermally (e.g., via simple passive diffusion formulations or via facilitated delivery using, for example, iontophoresis, microporation with microneedles, radio-frequency ablation or the like), intravascularly, cutaneously, subcutaneously, intramuscularly, sublingually, intracranially, epidurally, rectally, intravesically, and vaginally, among others.

As discussed above, compounds of formula (I) can be administered to a subject alone according to the present methods, or these compounds can be administered as a pharmaceutical composition. Pharmaceutical compositions of the present disclosure comprise a compound of formula (I) and one or more pharmaceutical excipients that are physiologically compatible with the subject to which they are administered. The present pharmaceutical compositions can be in dry or liquid form. Thus in some embodiments, pharmaceutical excipient(s) for use in the present pharmaceutical compositions can be solid or liquid and can incorporate, for example, both solid and liquid excipients/matrices. Pharmaceutical compositions comprising a compound of formula (I) can be formulated neat or with one or more pharmaceutical excipients for administration to a subject, for example for administration to a human. The nature and amount of the pharmaceutical excipient(s) comprising the pharmaceutical compositions of the present disclosure can be determined by factors such as the solubility and other chemical properties of the compounds of formula (I), chosen route of administration and standard pharmacological practice. In some embodiments, pharmaceutical compositions of the present disclosure optionally contain one or more excipients and one or more compounds of formula (I).

Examples of suitable excipients for use in pharmaceutical compositions of the present disclosure include surfactants, adjuvants, antioxidants, binders, buffers, coatings, coloring agents, compression aids, diluents, disintegrants, emulsifiers (e.g., polyoxyethylene fatty acid esters), emollients, encapsulating materials, fillers, flavoring agents, glidants, granulating agents, lubricants, metal chelators, osmo-regulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc.) or viscosity regulators (such as polymers to increase viscosity), for example as described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In some embodiments, the compounds of formula (I) can be formulated into pharmaceutical compositions with one or more a solid excipients. In one embodiments, the pharmaceutical compositions can be compacted into a unit dose form, i.e., tablet or caplet. In another embodiment, the pharmaceutical compositions can be added to unit dose form, i.e., a capsule. In a further embodiment, the pharmaceutical compositions can be formulated for administration as a powder. The solid excipient comprising a pharmaceutical composition of the present disclosure can perform a variety of functions; i.e., can perform the functions of two or more of the excipients described below. For example, a solid excipient can act as a flavoring agent, lubricant, solubilizer, suspending agent, filler, glidant, compression aid, binder, disintegrant, or encapsulating material. In one embodiment, a solid excipient acts as a lubricant, solubilizer, suspending agent, binder, disintegrant, or encapsulating material. Similarly, a variety of suitable solid (e.g., rigid or flexible) excipients and excipients are well-known to those of skill in the art. Such suitable solid excipients can also be designed so as to undergo a state transition when introduced into the body, for example into a body cavity such as the bladder (e.g., liquid to gel, liquid to solid, gel to solid), and such materials are well-known to those skilled in the art. Such suitable solid excipients can also comprise a membrane, for example comprising a thermoelastic polymer, which defines a reservoir containing a solid or liquid pharmaceutical composition of the present disclosure. Other suitable solid excipients can comprise a thermoelastic polymer matrix, in which a pharmaceutical composition of the present disclosure is embedded. The compounds of formula (I) or a pharmaceutical composition of the present disclosure comprising a compounds of formula (I) can also be administered to a subject together with other-membrane stabilizers (e.g., local anesthetics), for example to form eutectic mixtures.

Liquid pharmaceutical compositions of the present disclosure can comprise sterile solutions or suspensions. When liquid excipients are utilized, they can be sterile liquids. Other suitable liquid excipients can be utilized in preparing liquid pharmaceutical compositions of the present disclosure, for example formulated as solutions, suspensions, emulsions, syrups and elixirs. In one embodiment, a liquid pharmaceutical composition of the present disclosure comprises a compound of formula (I) dissolved a liquid excipient. In another embodiment, a liquid pharmaceutical composition of the present disclosure comprises a compound of formula (I) suspended in a liquid excipient. A variety of suitable liquid excipients are well-known and can be readily selected by one of skill in the art and can include, e.g., dimethylsulfoxide (DMSO), saline, buffered saline, cyclodextrin, hydroxypropylcyclodextrin (HPβCD), n-dodecyl-β-D-maltoside (DDM) and mixtures thereof.

In some embodiments, the present pharmaceutical compositions can be sub-divided into unit dosage forms to contain appropriate quantities (e.g., therapeutically effective amounts) of a compound of formula (I). For example, the unit dosage can comprise packaged compositions, e.g., packeted powders, vials, ampoules, prefilled syringes or sachets containing liquids.

In one embodiment, the pharmaceutical compositions of the present disclosure can be utilized as inhalants. For this route of administration, pharmaceutical compositions of the present disclosure can be prepared as fluid unit doses comprising a compound of formula (I) and a vehicle for delivery, for example, by an atomizing spray pump, or as a dry powder comprising a compound of formula (I) for insufflation.

In another embodiment, pharmaceutical compositions of the present disclosure can be administered according to the present methods as aerosols; i.e., for oral or intranasal administration. For such routes of administration, the present pharmaceutical compositions can be formulated, for example, for use in a pressurized aerosol container together with a gaseous or liquefied propellant; e.g., dichlorodifluoromethane, carbon dioxide, nitrogen, propane, and the like, and can be delivered as a metered dose in one or more actuations of a suitable delivery device. In certain embodiments, pharmaceutical compositions of the present disclosure formulated for inhalation can comprise any well-known pharmaceutically acceptable medically inert excipient, such as diluents, excipients, surfactants and flavorings.

In another embodiment, pharmaceutical compositions of the present disclosure can comprise an ingestible liquid, such as a syrup, elixir, solution, suspension, emulsion, microemulsion, nano-emulsion, colloid, liquid gel, or the like. In still another embodiment, the present pharmaceutical compositions can be formulated for oral administration in an oral film, lozenge, drop, or chewable dosage form which can include, for example, a pill, gum and the like. Pharmaceutical compositions of the present disclosure formulated as oral dosage forms can be useful for treating subjects that are young, elderly, or have swallowing issues, or for subjects that are non-human animals.

In another embodiment, pharmaceutical compositions of the present disclosure can be formulated to achieve a modified-release of the compound of formula (I). "Modified-release" as used herein refers to delivery of a therapeutically effective amount of a compound of formula (I) which is controlled, for example, to prevent immediate release or to release the compound of formula (I) over an extended or sustained period; for example over at least about 8 hours (e.g., extended delivery) to at least about 12 hours (e.g., sustained delivery). Pharmaceutical compositions of the present disclosure can also be formulated to permit immediate release of a therapeutically effective amount of a compound of formula (I) (e.g., where therapeutic levels are achieved in less than about 1 hour or in less than about 2 hours).

Compounds of formula (I) or pharmaceutical compositions of the present disclosure can also be administered to a subject according to the present methods by a modified release delivery device. Suitable modified release delivery devices include, for example, drug-eluting implants. Such implants can comprise a thermoelastic polymer matrix, such as a silicon or ethylene vinyl acetate matrix, wherein one or more compounds of formula (I), optionally with one or more pharmaceutically acceptable excipients, is embedded. Suitable implants are described, for example, in U.S. Pat. No. 7,736,665 and US Patent Publication No. US-2011/0280922, the disclosures of which are herein incorporated by reference.

Other suitable drug-eluting implants can comprise an "osmotic pump" or other mechanism by which a solution comprising one or more compounds of formula (I), or a pharmaceutical composition comprising a compound of formula (I), contained within the device is forced out, for example through the implant walls or through one or more apertures, by osmotic pressure which builds within the device once it is implanted into a subject. Suitable osmotic pump drug eluting implants are described, for example, in U.S. Pat. Nos. 5,035,891 and 6,464,688, the disclosures of which are herein incorporated by reference.

Still other suitable drug-eluting implants can comprise a hydrogel such as a polymethacrylate-based polymer (e.g., as described in U.S. Pat. Nos. 5,292,515 and 5,266,325, the disclosures of which are herein incorporated by reference), or a thermoelastic polymer, such as a polyurethane (e.g., as described in U.S. Pat. Nos. 7,858,110 and 7,842,303, the disclosures of which are herein incorporated by reference), which define a reservoir containing a solid or liquid composition comprising one or more compounds of formula (I) or pharmaceutical compositions of the present disclosure. Still other drug-eluting implants suitable for use in the present methods can comprise a bio-degradable or bio-erodable polymer and at least one or more compounds of formula (I) or pharmaceutical compositions of the present disclosure, for example as described in U.S. Pat. Nos. 4,906,474 and 5,633,002, the disclosures of which are herein incorporated by reference.

Modified release of the compounds of formula (I) or a pharmaceutical composition comprising a compounds of formula (I) can also be achieved by injecting the compounds or compositions into the bladder tissue (e.g., into the urothelium or muscularis propria) with a device that can be employed via an endoscope inserted into the bladder or percutaneously. For example, compounds of formula (I) or pharmaceutical compositions of the present disclosure can be injected into the bladder tissue via a needle, or a needleless device, for example as described in US Patent Publication No. US-2011/0046600, the disclosure of which is incorporated by reference. A suitable needleless injection device for use in the present methods includes the Jet-Touch™ platform (American Medical Systems; Minnetonka, Minn.). The injected compounds of formula (I) or pharmaceutical compositions of the present disclosure can form a depot, and in certain embodiments, the injected compounds of formula (I) or pharmaceutical compositions of the present disclosure can be encapsulated in a bio-degradable or bio-erodable polymer, for example as described in U.S. Pat. Nos. 5,480,656 and 6,036,976, the disclosures of which are incorporated by reference.

Modified release of the compounds of formula (I) or pharmaceutical compositions of the present disclosure can also be achieved by instilling the compounds or pharmaceutical compositions with at least one material that solidifies or gels upon administration, for example once instilled into the bladder or upon contact with the bladder urothelium, to coat at least a portion of the bladder wall. The compounds of formula (I) or pharmaceutical compositions of the present disclosure can then elute from the solidified or gelled material. See, e.g., U.S. Pat. Nos. 6,894,071; 5,575,815 and 6,039,967, the disclosures of which are incorporated by reference, for examples of suitable gelling or solidifying materials.

In still a further embodiment, the compounds of formula (I) or pharmaceutical compositions of the present disclosure can be administered transdermally, e.g., via the use of a drug-eluting patch. In one embodiment, the drug-eluting patch is an "iontophoretic" transdermal patch in drug delivery is effected using, e.g., microprocessor-controlled, electrical current produced by, for example, an external source or an on-board battery. In a further embodiment, the drug-eluting patch is a "microneedle" transdermal patch, which contains microneedles coated with or containing (e.g., in dissolvable or non-dissolvable form) a compound of formula (I) or pharmaceutical composition of the present disclosure. Suitable "microneedle" transdermal patches are described in, e.g., U.S. Pat. Nos. 7,798,987 and 7,537,795, the disclosures of which are herein incorporated by reference. The microneedles can themselves be dissolvable or non-dissolvable; see, for example, the "microneedle" technology described in Sullivan, "Dissolving Polymer Microneedle Patches for Influenza Vaccination", Nature Medicine, 16:915-920 (Jul. 18, 2010 online publication) and Lee, "Dissolving Microneedle Patch for Transdermal Delivery of Human Growth Hormone", Small, 7(4):531-539 (Jan. 4, 2011 online publication), which are herein incorporated by reference.

Other suitable transdermal delivery systems for use in the present methods include the radio-frequency ablation systems described in Sintov, "Radiofrequency-Driven Skin Microchanneling as a New Way for Electrically Assisted Transdermal Delivery of Hydrophilic Drugs", Controlled Release 89: 311-320 (2003), and U.S. Pat. No. 7,558,625, the disclosures of which are herein incorporated by reference, and the transdermal patches described in U.S. Pat. Nos. 5,411,738 and 5,827,528 and Prausnitz and Langer, "Transdermal drug delivery", Nature Biotechnology, 26(11): 1261-1268, November 2006, which are herein incorporated by reference.

In some embodiments, a transdermal delivery system for use according to methods of the present disclosure can be selected which permits or assists a compound of formula (I) in passing through the dermal layer and to the targeted area, such as muscular tissues or a perineural space. Such systems can include formulation or use of a compound of formula (I) with skin penetration enhancers. Suitable skin penetration enhancers include, for example, physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulfoxides, azones, glycols, alkanols, terpenes, etc.). Other suitable chemical enhancers include, e.g., propylene glycol, polyethylene glycol, isopropanol, ethanol, oleic acid, N-methylpyrrolidone, which can increase the permeability of the skin to the compounds, and permit the compounds to penetrate through the skin to deeper tissues. Suitable examples of chemical skin penetration enhancers for use in the present methods are also described in, for example, Sagie & Kohane, "Prolonged Sensory-Selective Nerve Blockade", PNAS, 2010(8): 3740-3745, 2010, which is herein incorporated by reference.

In one embodiment, a transdermal patch for use according to the present methods is applied via a suitable adhesive on the skin, where it remains in place for at least one hour. In a further embodiment, the patch remains in place for about 1 hour and is replaced weekly, for a total of about 2 or about 3 hours wear time. In another embodiment, the patch remains in place for about 2 hours, about 3 hours, about 4 hours, about 6 hours, about 12 hours or about 24 hours. In yet another embodiment, the patch remains in place for longer or shorter periods of time.

In certain embodiments of treatment methods of the present disclosure, a compound of formula (I) can be administered in combination with one or more other medications or therapeutic agents. In one embodiment, a compounds of formula (I) can be combined with other medications or therapeutic agents in a single pharmaceutical composition. In other embodiments, a compound of formula (I) can be administered in one or more separate formulations from other compounds of formula (I), or other medications or therapeutic agents as described below. For treating pain and respiratory dysfunction, these other medications or therapeutic agents for administration in combination with the compounds of formula (I) can include, for example, TRPV1 and TRPA receptor activators and inhibitors, inhibitors of voltage-gated ion channels, non-steroidal anti-inflammatory drugs (NSAIDs), steroids, inhibitors of Spleen Tyrosine Kinase and the JAK-STAT pathway, cytokine inhibitors or modulators, opioids, tricyclic antidepressants, amine transporter inhibitors, and anticonvulsants (such as gabapentinoids). Other medications or therapeutic agents that can be used in combination with compounds of formula (I) for treating respiratory conditions include anticholinergic agents and beta-receptor agonists.

In one embodiment, methods of the present disclosure comprise administering to a subject a compound of formula (I), or pharmaceutical compositions comprising a compound of formula (I), with a with a TRPV1 receptor activator for regulating activity of either or both of the $P2X_3$ or $P2X_{2/3}$ pathways. Regulation of either or both of the $P2X_3$ or $P2X_{2/3}$ pathways can result in the treatment of pain or respiratory dysfunction in a subject. The term "TRPV1 receptor activator" as used herein refers to any agent or stimulus that activates TRPV1 receptors on nociceptors or puriceptors, and allows for entry of at least one inhibitor of voltage-gated ion (e.g., sodium or calcium) channels. In one embodiment, the TRPV1 receptor activator includes, for example, capsaicin, dihydrocapsaicin and nordihydrocapsaicin, lidocaine, articaine, procaine, tetracaine, mepivicaine, bupivicaine, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), Cl 8 N-acylethanolamines, lipoxygenase derivatives (such as 12-hydroperoxyeicosatetraenoic acid), inhibitor cysteine knot (ICK) peptides (vanillotoxins), MSK1 95 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-α-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea) nonivamide, and fatty acyl amides of tetrahydroisoquinolines. In another embodiment, the TRPV1 receptor activator is lidocaine, aprindine, benzocaine, butacaine, cocaine, dibucaine, encainide, mexiletine, oxetacaine (oxethazaine), prilocaine, proparacaine, procainamide, n-acetylprocainamide, chloroprocaine (nesacaine, nescaine), dyclonine, etidocaine, levobupivacaine, ropivacaine, cyclomethycaine, dimethocaine (larocaine), propoxycaine, trimecaine, and sympocaine. In a further embodiment, the TRPV1 receptor activator is lidocaine. In another embodiment, the TRPV1 activator can be a detergent or a surfactant, examples of which can be found in commonly-used hygiene products such as soaps and shampoos (e.g., sodium lauryl sulfate), for example as described in Lilja, "Surfactant-Induced TRPV1 activity—A Novel Mechanism for Eye Irritation?" Technological Sciences, 99(1):174-180, 2007, which is incorporated herein by reference. In another embodiment, the TRPV1 receptor activator is not a chemical agent, but is heat or inflammation, both of which are known to activate TRPV1 receptors.

In one embodiment, the amount of the TRPV1 receptor activator used in the present methods is about 0.0001% to about 10% w/v. One of skill in the art would readily understand that the recited TRPV1 receptor activator amount can be based, where appropriate, on the free base of the TRPV1 receptor activator. In some embodiments, the TRPV1 receptor activator amount is less than about 10% w/v, about 9% w/v, about 8% w/v, about 7% w/v, about 6% w/v, about 5% w/v, about 4% w/v, about 3% w/v, about 2% w/v, or about 1% w/v. In another embodiment, the therapeutically effective amount is about 0.1% to about 5% w/v, for example about 0.5 to about 3% w/v; about 0.5 to about 2% w/v; or about 2% w/v. In another embodiment, the TRPV1 receptor activator amount is about 1% w/v or about 0.5% w/v.

In some embodiments, the amount of the TRPV1 receptor activator can be about 0.001 mg to about 100 mg per dose based on a 70 kg mammalian subject, for example about 0.1 mg to about 25 mg per dose; or about 1 mg to about 5 mg per dose. In other embodiments, the amount of the TRPV1 receptor activator can be about 0.1 mg, about 0.5 mg, about 1 mg, about 2 mg, about 3 mg, about 4 mg, about 5 mg, about 6 mg, about 7 mg, or about 8 mg per dose.

In one embodiment, a pharmaceutical composition of the present disclosure comprises a compound of formula (I) and lidocaine; for example about 0.01% to about 1% w/v of a compound of formula (I) and about 0.1% to about 5% w/v of lidocaine; about 0.1% to about 0.7% w/v of a compound of formula (I) and about 1% to about 3% w/v of lidocaine;

about 0.2% to about 0.5% w/v of a compound of formula (I) and about 1% to about 3% w/v of lidocaine; about 0.2% to about 0.5% w/v of a compound of formula (I) and about 2% w/v of lidocaine; about 0.2% w/v of a compound of formula (I) and about 2% w/v of lidocaine; or about 0.5% w/v of a compound of formula (I) and about 2% w/v of lidocaine. As discussed above, these compositions can be further diluted. In one embodiment, these pharmaceutical compositions can be diluted 2-fold. In another embodiment, these pharmaceutical compositions can be diluted 4-fold.

Also contemplated for use in the present methods are pharmaceutical compositions comprising a compound of formula (I) and inhibitors of voltage-gated ion channels. In one embodiment, the voltage-gated ion channels are sodium or calcium ion channels. Suitable voltage-gated sodium channel inhibitors include, for example, QX-314, N-methyl-procaine (QX-222), N-octyl-guanidine, 9-aminoacridine, and pancuronium. Suitable voltage-gated calcium channel inhibitors include, for example, D-890 (quaternary methoxyverapamil) and CERM 1 1888 (quaternary bepridil). Other suitable voltage-gated ion channel inhibitors include, for example, riluzole, mexilitine, phenytoin, carbamazepine, procaine, tocainide, prilocaine, diisopyramide, bencyclane, quinidine, bretylium, lifarizine, lamotrigine, flunarizine, articaine, bupivicaine, mepivicaine, fluspirilene, orphenadrine, phenbenzamine, bepridil, pimozide, penfluridol, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine.

Pharmaceutical compositions of the present disclosure can also comprise a compound of formula (I) and a membrane permeable inhibitor of voltage-gated ion channels. Suitable membrane permeable inhibitor of voltage-gated ion channels include, for example, cocaine, carbamazepine, disopyramide, lamotrigine, procainamide, phenytoin, oxcarbazepine, topiramate, zonisamide, tetracaine, ethyl aminobenzoate, prilocaine, disopyramide phosphate, flecainide acetate, mexiletine, propafenone, quinidine gluconate, quinidine polygalacturonate, chloroprocaine, dibucaine, dyclonine, mepivacaine, pramoxine, procaine, tetracaine, oxethazaine, propitocaine, levobupivacaine, bupivacaine, lidocaine, moricizine, tocainide, proparacaine, ropivacaine, quinidine sulfate, encainide, ropivacaine, etidocaine, moricizine, quinidine, encainide, flecainide, tocainide, fosphenytoin, chloroprocaine, dyclonine, L-(−)-1-butyl-2',6'-pipecoloxylidide and pramoxine.

Pharmaceutical compositions of the present disclosure can also comprise a compound of formula (I) and a vasoconstrictor, e.g., epinephrine or vasopressin or (for example when formulated as injectable solutions) can comprise glucose or dextrose and a compound of formula (I), and can be administered as an infusion or as a regional analgesic or anti-pruritic.

In some embodiments, the present disclosure also provides regimens, kits or packages comprising a compound of formula (I) or pharmaceutical formulations comprising the compounds of formula (I), or one or more dosage forms thereof, optionally together with instructions for storage and/or use.

The kits of the present disclosure can further comprise packaging or a container holding the present compounds or pharmaceutical compositions formulated for a given route of administration. The kit can optionally comprise instructions on dosing and/or an insert regarding the compounds of formula (I). The optional instructions can, for example, contain information regarding assays for monitoring local or circulating levels of compounds of formula (I) or their metabolites, and the kit can further comprise materials for performing such assays including, e.g., reagents, well plates, containers, markers or labels, and the like.

Kits of the present disclosure can be readily packaged in a manner suitable for treatment of an indication. For example, the kit can comprise a patch, spray pump, nasal spray, inhaler (including aerosol, metered dose, and dry powder inhalers, nebulizer, or other suitable device, and optionally instructions for their use. Other suitable components to include in kits of the present disclosure will be readily apparent to one of skill in the art, taking into consideration the indication and the delivery route, and can comprise, for example, lubricants, antiseptic solutions and local anesthetic agents to facilitate the placement and use of the delivery device.

As discussed above, the compounds of formula (I) or pharmaceutical compositions of the present disclosure can be administered to a subject in single dose or in multiple doses, for example for continuous or periodic discontinuous administration. For continuous administration, a package or kit of the present disclosure can comprise a compound of formula (I) or a pharmaceutical composition comprising a compound of formula (I) in one or more dosage units; e.g., solution, lotion, tablet, pill, drug-eluting unit/patch or other unit dosage form described above or which can be utilized in drug delivery, and optionally instructions for administering the doses (for example less-than-daily, daily, weekly, or monthly) for a predetermined length of time or as prescribed. When the compounds or pharmaceutical compositions of the present disclosure are to be delivered periodically in a discontinuous fashion, a package or kit can comprise placebos during periods when the compounds of formula (I) or pharmaceutical compositions are not delivered. When treatment methods of the present disclosure comprise varying concentrations of a composition, of the components of the composition, or the relative ratios of the compounds of formula (I) or agents or excipients comprising a pharmaceutical a composition over time, a package or kit can contain a sequence of dosage units which provide the variability.

A number of packages for dispensing pharmaceutical agents for periodic oral use suitable for use in kits of the present disclosure are well-known in the art. In one embodiment, the package can comprise indicators for each period. In another embodiment, the package comprises a foil or blister package, labeled ampoule, vial or bottle.

In some embodiments, the kit of the present disclosure can itself be used to effect administration of a compound of formula (I) or a pharmaceutical composition comprising a compound of formula (I), and can comprise a drug delivery device such as an inhaler, syringe, pipette, eye dropper, catheter, cytoscope, trocar, cannula, pressure ejection device, or other such apparatus, for example from which the present compounds or pharmaceutical compositions can be administered to a subject, (e.g., by application to an affected area of the subject's body).

A compound of formula (I), or a pharmaceutical composition comprising a compound of formula (I), comprising a kit of the present disclosure can be provided in dried or lyophilized forms, for reconstitution by the addition of a suitable solvent, which solvent can be provided with the kit. In some embodiments, the suitable solvent also can be provided in another package.

In some embodiments, the kits of the present disclosure can comprise a means (e.g., vials or other suitable packaging means) for containing compounds of formula (I), or pharmaceutical compositions comprising a compound of formula (I), in close confinement for commercial sale such as, e.g., injection or blow-molded plastic containers.

The compounds of formula (I) (either alone or comprising pharmaceutical formulations) are useful in regulating the the $P2X_3$ and/or $P2X_{2/3}$ pathways, which regulation can result in treating conditions which are associated with the $P2X_3$ and/or $P2X_{2/3}$ pathways, such as pain or respiratory dysfunction. The term "regulation," "modulation" or variations thereof, as used herein, are used interchangeably and refer to the ability of a compound of formula (I) to inhibit or reduce the activity of one or more components of a biological pathway. In one embodiment, "regulation" refers to inhibition of $P2X_3$ activity. In another embodiment, "regulation" refers to inhibition of $P2X_{2/3}$ activity. In a further embodiment, "regulation" refers to dual inhibition of $P2X_3$ and $P2X_{2/3}$ activity.

Accordingly, in one embodiment, the present disclosure provides a method of treating pain in a subject, comprising administering to the subject a therapeutically effective amount of a compound of formula (I) (either alone or comprising a pharmaceutical formulation). Any type of pain can be treated by the methods of the present disclosure. The term "pain" as used herein thus includes all types of pain, for example acute or chronic. In another embodiment, the pain can be somatic, central, visceral, idiopathic, dysfunctional, nociceptive, neuropathic, inflammatory, and/or procedural pain.

"Somatic pain" includes pain from bone, joint, muscle, skin, or connective tissue.

"Central pain" includes pain arising as a consequence of brain trauma, stroke, or spinal cord injury.

"Visceral pain" includes pain from visceral organs, such as the respiratory or gastrointestinal tract and pancreas, the urinary tract and reproductive organs. In one embodiment, visceral pain results from tumor involvement of the organ capsule. In another embodiment, visceral pain results from obstruction of hollow viscus. In a further embodiment, visceral pain results from inflammation as in cystitis or reflux esophagitis.

"Idiopathic pain" refers to pain which has no underlying cause or refers to pain caused by condition which remains undiagnosed.

"Dysfunctional pain" refers to pain which occurs in the absence of a noxious stimulus, tissue damage or a lesion to the nervous system. In one embodiment, dysfunctional pain results from rheumatologic conditions such as arthritis and fibromyalgia, tension type headache, irritable bowel disorders and erythermalgia.

"Nociceptive pain" includes pain caused by noxious stimuli that threaten to or actually injure body tissues. In one embodiment, nociceptive pain results from a cut, bruise, bone fracture, crush injury, burn, trauma, surgery, labor, sprain, bump, injection, dental procedure, skin biopsy, or obstruction. In another embodiment, nociceptive pain is located in the skin, musculoskeletal system, or internal organs.

"Neuropathic pain" is pain due to abnormal processing of sensory input by the peripheral or central nervous system consequent on a lesion to these systems. In one embodiment, neuropathic pain is chronic and non-malignant. In one embodiment, neuropathic pain is due to trauma, surgery, herniation of an intervertebral disk, spinal cord injury, diabetes, infection with herpes zoster (shingles), HIV/AIDS, late-stage cancer, amputation (such as mastectomy), carpal tunnel syndrome, chronic alcohol use, exposure to radiation, and as an unintended side-effect of neurotoxic treatment agents, such as certain anti-HIV and chemotherapeutic drugs. In another embodiment, neuropathic pain is can be described as "burning," "electric," "tingling," or "shooting".

"Inflammatory pain" includes pain resulting from inflammation caused by any number of factors. In one embodiment, inflammatory pain occurs due to tissue damage or inflammation. In another embodiment, inflammatory pain is due to injury (including joints, muscle, and tendons injuries), surgical procedures, infection, and/or arthritis.

"Procedural pain" refers to pain arising from a medical procedure. The medical procedure can include any type of medical, dental or surgical procedure. In one embodiment, the procedural pain is postoperative. In another embodiment, the pain is associated with an injection, draining an abscess, surgery, dermatological, dental procedure, ophthalmic procedure, arthroscopy and use of other medical instrumentation, and/or cosmetic surgery.

For example, the pain can be from a migraine, back pain, neck pain, gynecological pain, pre-labor or labor pain, orthopedic pain, post-stroke pain, post-surgical or procedural pain, post herpetic neuralgia, sickle cell crises, interstitial cystitis, urological pain (such as urethritis), dental pain, headache, pain from a wound or from a medical procedure such as surgery (such as bunionectomy or hip, knee or other joint replacement), suturing, setting a fracture, biopsy, and the like. Pain can also occur in patients with cancer, which can be due to multiple causes, such as inflammation, nerve compression, and mechanical forces resulting from tissue distension as a consequence of invasion by a tumor and tumor metastasis into bone or other tissues. In one embodiment, the cancer is bone cancer.

In one embodiment, the pain is neuropathic pain, such as post-herpetic neuralgia. In another embodiment, the pain is inflammatory pain. In a further embodiment, the pain is nociceptive pain. In still another embodiment, the pain is procedural pain. In yet a further embodiment, the pain is caused by esophageal cancer, colitis, cystitis, irritable bowel syndrome, colitis or idiopathic neuropathy. In still another embodiment, the pain is caused by airway, bladder or visceral organ dysfunction.

The term "treat", "treating", or any variation thereof is meant to include any therapy utilized to stabilize, lessen or ameliorate a health problem or condition in a patient or subject. In one embodiment, the health problem or condition can be eliminated permanently or for a shorter period of time. In another embodiment, the severity of the health problem or condition, or of one or more symptoms characteristic of the health problem or condition, can be delayed, kept from worsening, prevented from occurring, or lessened permanently or for a shorter period of time. The effectiveness of a treatment of pain can be determined using any standard pain index, such as those described herein, or can be determined based on the patient's subjective pain. A patient can be considered "treated" if there is a reported reduction in pain or a reduced reaction to stimuli that should cause pain.

Thus for the treatment of pain according to the present methods, a subject is treated for pain, for example, if there is a measurable change in a relevant biological or chemical marker (including by measurement of a change in degree of binding affinity, etc. of such a marker) that is consistent with a reduction in pain, or if the subject experiences or is observed to experience a reduction in pain frequency, duration or intensity, or an improved quality of life apparently due to reduction in pain. For the treatment of respiratory dysfunction according to the present methods, a subject is treated for respiratory dysfunction if there is a measurable change in a relevant biological or chemical marker (including by measurement of a change in degree of binding affinity, etc. of such a marker) that is consistent with a reduction in one or more symptoms or a lessening of the severity of a respiratory condition, for example if the subject experiences or is observed to experience less frequent or less intense cough, labored breathing, etc.

In order to measure the usefulness or effectiveness of any the treatment methods of the present disclosure, any suitable measurement index can be used. Indices that are suitable for the measurement of pain associated with musculo skeletal, immunoinflammatory and neuropathic disorders include a visual analog scale (VAS), a Likert scale, categorical pain scales, subjective patient descriptors, the Lequesne index, the WOMAC index, and the AUSCAN index, each of which is well known in the art. Such indices can be used to measure pain, function, stiffness, or other variables.

Indices that are useful of the measurement of pain associated with interstitial cystitis include the interstitial cystitis symptom index (ICSI), the interstitial cystitis problem index (ICPI), the pain-urgency-frequency score (PUF), the Wisconsin Symptom Instrument (UWI) and a visual analog scale (VAS) such as the Likert scale and other categorical pain scales.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a subject can be asked to rank a sensation of pain by choosing the spot on the line that best corresponds to the sensation of pain, where one end of the line corresponds to "no pain" (score of 0 cm) and the other end of the line corresponds to "unbearable pain". This procedure provides a simple and rapid approach to obtaining quantitative information about how the patient is experiencing pain. VAS scales and their use are described, e.g., in U.S. Pat. Nos. 6,709,406 and 6,432,937, the relevant disclosures of which are herein incorporated by reference.

A Likert scale similarly provides a measure of a one-dimensional quantity. Generally, a Likert scale has discrete integer values ranging from a low value, e.g., 0, meaning no pain, to a high value, e.g., 7, meaning extreme pain. A patient experiencing pain is asked to choose a number between the low value and the high value to represent the degree of pain experienced. Likert scales and their use are described, e.g., in U.S. Pat. Nos. 6,623,040 and 6,766,319, the relevant disclosures of which are herein incorporated by reference.

The Lequesne index and the Western Ontario and McMaster Universities (WOMAC) osteoarthritis (OA) index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert scale. Both the WOMAC index and the Lequesne index questionnaires have been extensively validated in OA, including in surgical settings, e.g., knee and hip arthroplasty, and their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index can utilize, e.g., a Likert or a VAS scale.

The O'Leary-Sant score and IC Problem Index are self-administered indices for measuring lower urinary tract symptoms.

The Pain-Urgency-Frequency symptom scale is balanced assessment of urinary dysfunction, pelvic pain and symptoms associated with sexual intercourse and frequently used in conjunction with intravesical potassium chloride administration.

The UWI utilizes seven IC-related questions about frequency, urgency, noctuira and pain.

In addition to the indices discussed above, other suitable indices that are useful for the measurement of pain include the Pain Descriptor Scale (PDS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

In another embodiment, the present disclosure provides a method of treating respiratory dysfunction in a subject, comprising administering to the subject a therapeutically effective amount of a compound of formula (I) (either alone or comprising a pharmaceutical composition). The term "respiratory dysfunction" as used herein includes, for example, any disruption of normal respiratory function in a subject, such as bronchial hyperactivity, bronchoconstriction, bronchospasm, hypersecretion, cough, cough hypersensitivity syndrome, wheezing, dyspnea, breathless, and chest tightness, for example due to a respiratory disease or disorder. The term "respiratory disease or disorder" as used herein includes, for example, idiopathic pulmonary fibrosis (IPF), chronic obstructive pulmonary disease (COPD), asthma, upper respiratory infection, interstitial lung disease (ILD), post-nasal drip, and bronchitis. The respiratory dysfunction can also be associated with gastroesophageal reflux disease (GERD), or can be an iatrogenic cough, including cough associated with treatment with an ACE (Angiotensin Converting Enzyme) inhibitor, or can be "smoker's cough"; that is, cough associated with smoking or exposure to smoke, dust, ash or the like. The term "cough" as used herein thus refers to any cough including, for example, sub-acute cough, chronic cough, treatment-resistant cough, idiopathic chronic cough, cough associated with upper respiratory infection, post-viral cough, iatrogenic cough, smoker's cough, cough associated with bronchitis, post-nasal drip or any other irritation of the bronchi or esophagus, the urge to cough associated with any respiratory disease, cough-variant asthma, interstitial lung disease, and whooping cough.

The terms "acute cough" refers to a cough lasting up to two weeks in duration. For instance, acute cough can be the result of an acute disease, such as a cold or flu. An acute cough will disappear when the underlying cause (e.g., cold or flu) is eliminated.

The terms "sub-acute cough" refers to a cough lasting between two and eight weeks. In some cases, a sub-acute cough follows a period in which a subject is infected with a disease (e.g., cold or flu). A sub-acute cough is one that often remains after the underlying cause has been removed. For instance, a sub-acute cough is found post-infection (e.g., post-viral infection).

The terms "chronic cough" refers to a persistent or refractory cough lasting longer than eight weeks that does not have an obvious underlying cause and can not be associated with other respiratory diseases, such as asthma or COPD. Chronic cough also generally has no hallmarks to define and diagnose it, in contrast to other respiratory diseases (e.g., COPD), and a subject suffering from chronic cough can be apparently normal in most other aspects. Chronic cough is characterized by frequent coughing (e.g., at least 5-10 coughs per hour during daytime) and bothersome coughing during sleep. Chronic cough can last for a period of years, including over a decade.

Various tools have been developed to assess cough in clinical practice and in clinical studies. For example, the visual analog scale (VAS) as described above for the assessment of pain, is also widely used for the assessment of cough severity. The Leicester cough questionnaire (LCQ) and the cough-specific quality of life questionnaire (CQLQ) are also used to assess the impact of chronic cough. Ambulatory devices consisting of a microphone and recording device, such as the Leicester cough monitor (LCM) and the Vitalo-Jak, are effective tools to measure cough frequency, particularly in clinical studies. Use of these tools can provides evidence to measure a reduction in cough frequency and/or severity for a patient, following treatment of a subject according to the present methods.

In one embodiment, the present disclosure provides a method of treating a respiratory condition in a subject comprising administering a therapeutically effective amount of a compound of formula (I) (either alone or comprising a pharmaceutical composition), wherein the respiratory condition is selected from the group consisting of acute cough, chronic cough, and cough associated with idiopathic pulmonary fibrosis (IPF). Treatment of the respiratory condition can be measured, for example, by one or more techniques selected from the group consisting of the visual analog scale (VAS) for cough severity, the Leicester cough questionnaire (LCQ), the cough-specific quality of life questionnaire (CQLQ) and the Leicester cough monitor (LCM).

The following examples are illustrative only and are not intended to limit the present disclosure.

EXAMPLES

Unless otherwise stated, all the raw materials are purchased from commercially available common suppliers. $^1$H-NMR spectra were recorded using tetramethylsilane (TMS) as the internal reference for CDCl$_3$ dissolved compounds. For DMSO-d$_6$, MeOD and D$_2$O dissolved compounds the instrument was calibrated at δ 2.5, 3.3 and 4.82 ppm respectively. The chemical shift values are quoted in δ (parts per million).

For LCMS analysis LCMS/MS API 2000 (Applied Biosystem) instrument was used.

The columns included:
Column V: Zorbax® C18 column, 4.6×50 mm, 5μ
Column W: Zorbax® Extend C18 column, 4.6×50 mm, 5μ
Column X: Gemini® NX C18 column, 4.6×50 mm, 5μ
Column Y: Xbridge® C18 column, 4.6×50 mm, 5μ
Column Z: Reprosil® column, 4.6×50 mm, 5μ

The eluent (solvent) typically included (acidic or basic buffer as aqueous phase):
A channel: (i) 0.05% formic acid in water; (ii) 10 mM ammonium acetate in water; or (iii) 0.05% TFA in water.
B channel: acetonitrile (organic phase).
The detector was UV measured at dual wavelengths: 220 and 260 nm.

The LCMS gradients were one of the following:
1. LCMS reaction monitoring and final compound analysis method (for general polarity compounds)
Gradient condition: 5 min run time
Time Programs: P1:10 mM ammonium acetate in water/acetonitrile
Q1: 0.05% TFA in water/acetonitrile,
R1: 0.05% formic acid in water/acetonitrile.
The gradient varied acetonitrile from 10% to 90% to 10%.
Flow rate: 1.2 mL/min.
2. LCMS reaction monitoring and final compound analysis method in 12 min run (for close eluting compounds):
Gradient condition: 12 min run time
Time Programs: P2: 10 mM ammonium acetate in water/acetonitrile
Q2: 0.05% TFA in water/acetonitrile
R2: 0.05% formic acid in water/acetonitrile
The gradient varied acetonitrile from 5% to 90% to 5%
Flow rate: 1.0 mL/min.
3. LCMS after method development in HPLC—gradient conditions are as per HPLC.

Mass spectral data was obtained using the following:
Ionization technique: ESI (Electron Spray Ionization) using API (Atmospheric pressure Ionization) source.
Declustering Potential: 10-70 V depending on the ionization of compound
Mass range: 100-800 amu
Scan type: Q1
Polarity: +/−ve
Ion Source: Turbo spray
Ion spray voltage: +5500 for +ve mode and −4500 for −ve mode
Mass Source temperature: 200° C.

Synthesis of Intermediates Used in Producing Compounds of Formula (I).

The following eighteen schemes show the synthesis of certain intermediates used to make compounds of formula (I). It will be apparent and understood by one of ordinary skill in the art that the chemical structures represented below that contain heteroatoms may, in certain circumstances, have one or more bound hydrogens that are not shown.

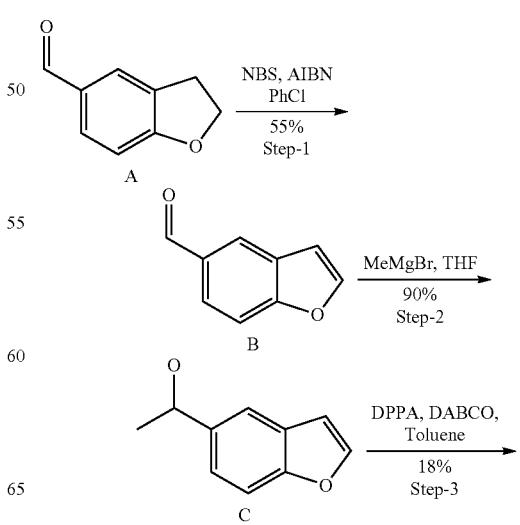

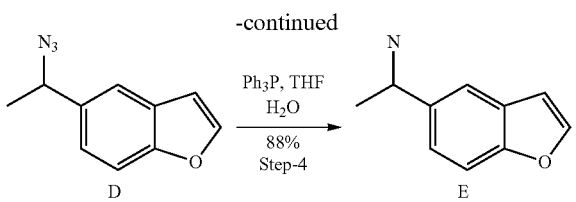

Step 1: Preparation of benzofuran-5-carbaldehyde (B)

To an ice-cold stirred solution of compound A (500 mg, 3.37 mmol, 1 eq) in chlorobenzene (10 ml) were added NBS (721 mg, 4.05 mmol, 1.2 eq) in portions and AIBN (11 mg, 0.07 mmol, 0.02 eq) and the resulting solution was stirred at 80° C. for 4 h. The reaction mixture was cooled to RT, concentrated in vacuo and the residue was washed with saturated aq. $NaHCO_3$ solution (20 ml). The organic components were extracted with ethyl acetate (50 ml) and the ethyl acetate layer was concentrated in vacuo. The crude material was purified by flash chromatography (Combiflash) using 100-200 mesh silica gel eluting with 5% ethyl acetate/hexane to obtain the compound B (270 mg, 55%) as white solid.

$^1$H NMR (400 MHz, DMSO-$d_6$) δ 10.06 (s, 1H), 8.28 (s, 1H), 8.16-8.16 (m, 1H), 7.89-7.87 (m, 1H), 7.81-7.79 (m, 1H), 7.16-7.15 (m, 1H);

LCMS: m/z=147.4 [M+H], RT=2.99 minutes; (Program R1, Column Y).

Step 2: Preparation of 1-benzofuran-5-yl-ethanol (C)

To a stirred solution of compound B (900 mg, 6.16 mmol, 1 eq) in dry THF (20 mL) was added methyl magnesium bromide (3 M in diethyl ether, 4.1 mL, 12.3 mmol, 2 eq) drop wise at −50° C. and the resulting mixture was stirred for 4 h at −50° C. The reaction mixture was quenched with saturated aq. $NH_4Cl$ solution (20 ml) and the organic components were extracted with ethyl acetate (200 ml). The ethyl acetate layer was dried over anhydrous sodium sulfate, concentrated in vacuo to obtain compound C (900 mg, 90%) as colorless sticky material which was used in the next step without further purification.

$^1$H NMR (400 MHz, DMSO-$d_6$) δ 7.97-7.94 (m, 1H), 7.60 (s, 1H), 7.50 (d, J=8 Hz, 1H), 7.29-7.27 (m, 1H), 6.94-6.91 (m, 1H), 5.15 (d, J=8 Hz, 1H), 4.84-4.78 (m, 1H), 1.35 (d, J=8 Hz, 3H).

Step 3: Preparation of 5-(1-azido-ethyl)-benzofuran (D)

To a stirred solution of compound C (200 mg, 1.23 mmol, 1 eq) in dry toluene (10 mL) were added DPPA (408 mg, 1.5 mmol, 1.2 eq) and DABCO (168 mg, 1.5 mmol, 1.2 eq) at 0° C. and the resulting mixture was stirred at 23° C. for 18 h. The reaction mixture was concentrated in vacuo. The crude residue was purified by flash chromatography (Combiflash) using 100-200 mesh silica gel and eluting with 20% ethyl acetate/hexane to obtain the compound D (40 mg, 18%) as brown sticky material.

$^1$H NMR (400 MHz, DMSO-$d_6$) δ 8.02-8.02 (m, 1H), 7.69 (s, 1H), 7.62 (d, J=8 Hz, 1H), 7.34 (d, J=8 Hz, 1H), 6.98-6.98 (m, 1H), 4.96-4.91 (m, 1H), 1.50 (d, J=4 Hz, 3H).

Step 4: Preparation of 1-benzofuran-5-yl-ethylamine (E)

To a stirred solution of compound D (40 mg, 0.21 mmol, 1 eq) in a mixture of THF (5 mL) and $H_2O$ (1 ml) was added triphenylphosphine (111 mg, 0.42 mmol, 2 eq) and the resulting mixture was stirred at 70° C. for 18 h. The reaction mixture was cooled to RT and concentrated in vacuo. The crude residue was purified by flash chromatography (Combiflash) using 100-200 mesh silica gel and eluting with 10% methanol/dichloromethane to obtain the compound E (30 mg, 88%) as brown sticky material.

$^1$H NMR (400 MHz, DMSO-$d_6$) δ 7.95 (d, J=4 Hz, 1H), 7.63 (s, 1H), 7.50 (d, J=8 Hz, 1H), 7.33-7.31 (m, 1H), 6.91-6.91 (m, 1H), 4.16-4.11 (m, 1H), 1.30 (d, J=8 Hz, 3H);

LCMS: m/z=162.2 [M+H], RT=1.56 minutes; (Program R1, Column Y).

SCHEME-2: Synthesis of 1-(2-Methyl-benzofuran-5-yl)-ethylamine

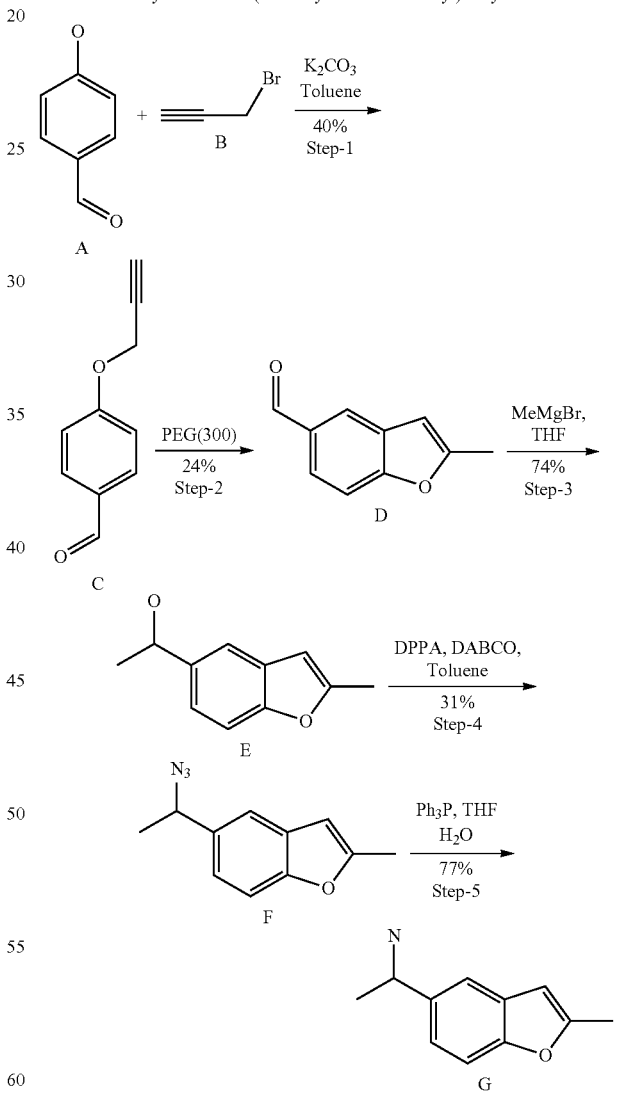

Step 1: Preparation of 4-prop-2-ynyloxy-benzaldehyde (C)

To a stirred solution of compound A (5.91 g, 48.4 mmol, 1 eq) in toluene (80 mL) were added compound B (80 wt.

% in toluene, 8 mL, 89.8 mmol, 1.85 eq) and $K_2CO_3$ (87.4 g, 633 mmol, 13 eq) at 0° C. and the resulting mixture was stirred at 100° C. for 8 h. The reaction mixture was cooled to RT, filtered and the filtrate was concentrated in vacuo. The crude material was purified by flash chromatography (Combiflash) using 100-200 mesh silica gel eluting with 20% ethyl acetate/hexane to obtain the compound C (3 g, 40%) as white solid.

$^1$H NMR (400 MHz, DMSO-$d_6$) δ 9.88 (s, 1H), 7.89 (d, J=8 Hz, 2H), 7.17 (d, J=8 Hz, 2H), 4.94 (d, J=2 Hz, 2H), 3.64 (br s, J=4 Hz, 1H);

LCMS: m/z=161.2 [M+H], RT=2.96 minutes; (Program R1, Column Y).

Step 2: Preparation of 2-methyl-benzofuran-5-carbaldehyde (D)

To compound C (3 g, 18.75 mmol, 1 eq) was added PEG-300 (30 mL) and the resulting mixture was heated to 220° C. for 4 h. The reaction mixture was cooled to RT, diluted with ice-water (70 ml) and the organic components were extracted with ethyl acetate (200 ml). The ethyl acetate layer was concentrated in vacuo and the crude material was purified by flash chromatography (Combiflash) using 100-200 mesh silica gel eluting with 20% ethyl acetate/hexane to obtain the compound D (700 mg, 24%) as white solid.

$^1$H NMR (400 MHz, DMSO-$d_6$) δ 10.02 (s, 1H), 8.12 (s, 1H), 7.80-7.78 (m, 1H), 7.69-7.67 (m, 1H), 6.76 (s, 1H), 2.48 (s, 3H);

LCMS: m/z=161.2 [M+H], RT=3.22 minutes; (Program R1, Column Y).

Step 3: Preparation of 1-(2-methyl-benzofuran-5-yl)-ethanol (E)

To a stirred solution of compound D (700 mg, 4.37 mmol, 1 eq) in dry THF (15 mL) was added methyl magnesium bromide (3M in diethyl ether, 3 mL, 8.75 mmol, 2 eq) drop wise at −50° C. and the resulting mixture was stirred for 4 h at −50° C. The reaction mixture was quenched with saturated aqueous $NH_4Cl$ solution (20 ml) and the organic components were extracted with ethyl acetate (50 ml). The ethyl acetate layer was concentrated in vacuo to obtain compound E (570 mg, 74%) as colorless sticky material.

$^1$H NMR (400 MHz, DMSO-$d_6$) δ 7.45 (s, 1H), 7.38 (d, J=8 Hz, 1H), 7.19-7.16 (m, 1H), 6.52 (s, 1H), 5.11 (d, J=4 Hz, 1H), 4.79-4.76 (m, 1H), 2.42 (s, 3H), 1.34 (d, J=4 Hz, 3H);

LCMS: m/z=175.0 [M−H], RT=3.03 minutes; (Program R1, Column Y).

Step 4: Preparation of 5-(1-azido-ethyl)-2-methyl-benzofuran (F)

To a stirred solution of compound E (600 mg, 3.41 mmol, 1 eq) in dry toluene (10 mL) were added DPPA(1.12 g, 4.09 mmol, 1.2 eq) and DABCO (459 mg, 4.09 mmol, 1.2 eq) at 0° C. and the resulting mixture was stirred at 23° C. for 18 h. The reaction mixture was concentrated in vacuo and the crude was purified by flash chromatography (Combiflash) using 100-200 mesh silica gel eluting with 10% ethyl acetate/hexane to obtain the compound F (210 mg, 31%) as brown sticky material.

$^1$H NMR (400 MHz, DMSO-$d_6$) δ 7.54 (s, 1H), 7.49 (d, J=8 Hz, 1H), 7.24-7.22 (m, 1H), 6.59 (s, 1H), 4.90-4.88 (m, 1H), 2.44 (s, 3H), 1.48 (d, J=8 Hz, 3H).

Step 5: Preparation of 1-(2-methyl-benzofuran-5-yl)-ethylamine (G)

To a stirred solution of compound F (210 mg, 1.04 mmol, 1 eq) in a mixture of THF (20 mL) and $H_2O$ (4 ml) was added triphenylphosphine (550 mg, 2.09 mmol, 2 eq) and the resulting mixture was stirred at 70° C. for 18 h. The reaction mixture was cooled to RT and concentrated in vacuo. The crude material was purified by flash chromatography (Combiflash) using 100-200 mesh silica gel eluting with 10% methanol/dichloromethane to obtain the compound G (130 mg, 77%) as brown sticky material.

$^1$H NMR (400 MHz, DMSO-$d_6$) δ 7.48 (s, 1H), 7.36 (d, J=8 Hz, 1H), 7.21-7.19 (m, 1H), 6.51 (s, 1H), 4.08-4.03 (m, 1H), 2.41 (s, 3H), 2.15 (br, 2H), 1.26 (d, J=8 Hz, 3H);

LCMS: m/z=176.1 [M+H], RT=2.06 minutes; (Program R1, Column Y).

SCHEME-3: Synthesis of 1-(4-Isopropoxy-phenyl)-ethylamine

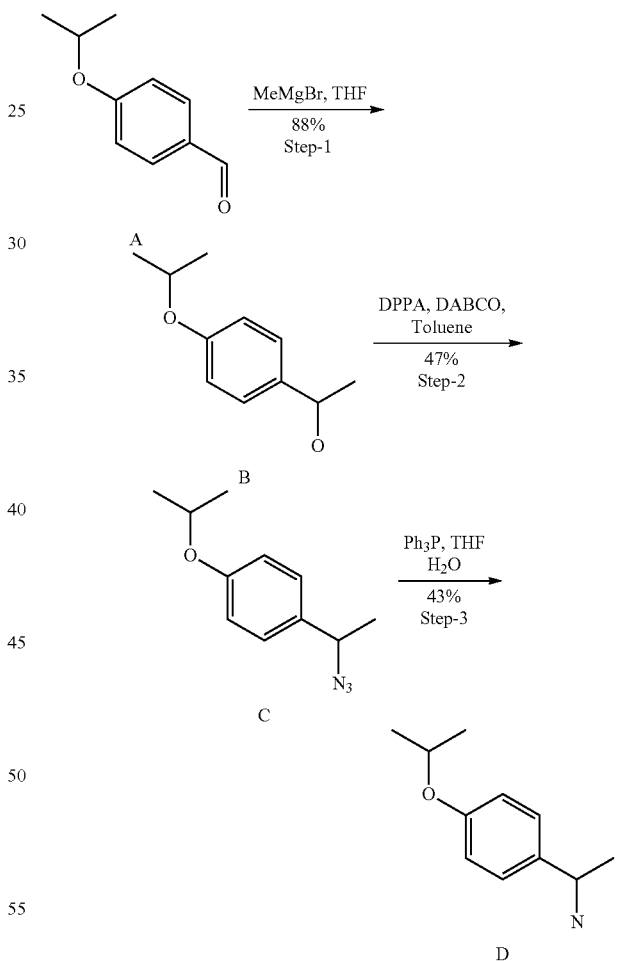

Step 1: Preparation of 1-(4-Isopropoxy-phenyl)-ethanol (B)

To a stirred solution of compound A (1 g, 6.09 mmol, 1 eq) in dry THF (20 mL) was added methyl magnesium bromide (3 M in diethyl ether, 4 mL, 12.18 mmol, 2 eq) drop wise at −50° C. and stirred for 4 h at −50° C. The reaction mixture was quenched with saturated aq. $NH_4Cl$ solution (30 ml) and the organic components were extracted with ethyl acetate (100 ml). The solvent was finally removed in vacuo to obtain the compound B (960 mg, 88%) as colorless sticky material.

$^1$H NMR (400 MHz, DMSO-d$_6$) δ 7.21 (d, J=8 Hz, 2H), 6.83 (d, J=8 Hz, 2H), 4.99 (d, J=4 Hz, 1H), 4.66-4.60 (m, 1H), 4.58-4.52 (m, 1H), 1.28 (d, J=8 Hz, 3H), 1.24 (d, J=4 Hz, 6H);

LCMS: m/z=163.1 [M+H], RT=3.40 minutes; (Program R1, Column Y).

Step 2: Preparation of
1-(1-Azido-ethyl)-4-isopropoxy-benzene (C)

To a stirred solution of compound B (450 mg, 2.5 mmol, 1 eq) in dry toluene (10 mL) was added DPPA (826 mg, 3 mmol, 1.2 eq) and DABCO (337 mg, 3 mmol, 1.2 eq) respectively at 0° C. and the reaction mixture was stirred at 23° C. for 18 h. The reaction mixture was concentrated in vacuo and the crude was purified by flash chromatography (Combiflash) using 100-200 mesh silica gel eluting with 10% ethylacetate/hexane to obtain the compound C (240 mg, 47%) as brown sticky material.

$^1$H NMR (400 MHz, DMSO-d$_6$) δ 7.28 (d, J=8 Hz, 1H), 7.15-7.12 (m, 1H), 6.92-6.79 (m, 2H), 4.77-4.72 (m, 1H), 4.65- (m, 1H), 1.42 (d, J=8 Hz, 3H), 1.33 (d, J=8 Hz, 6H).

Step 3: Preparation of
1-(4-Isopropoxy-phenyl)-ethylamine (D)

To a stirred solution of compound C (240 mg, 1.17 mmol, 1 eq) in THF (20 mL) and H$_2$O (4 ml) mixture, was added triphenylphosphine (615 mg, 2.34 mmol, 2 eq) and stirred at 70° C. for 18 h. The reaction mixture was concentrated in vacuo and the crude was purified by flash chromatography (Combiflash) using 100-200 mesh silica gel eluting with 10% methanol/dichloromethane to obtain the compound G (90 mg, 43%) as brown sticky material.

$^1$H NMR (400 MHz, DMSO-d$_6$) δ 7.23 (d, J=8 Hz, 2H), 6.81 (d, J=8 Hz, 2H), 4.57-4.51 (m, 1H), 3.94-3.89 (m, 1H), 2.1 (br s, 2H), 1.24-1.19 (m, 9H);

LCMS: m/z=180.3 [M+H], RT=2.06 minutes; (Program R1, Column Y).

SCHEME-4: Synthesis of 1-(2-Cyclopropyl-benzofuran-5-yl)-ethylamine

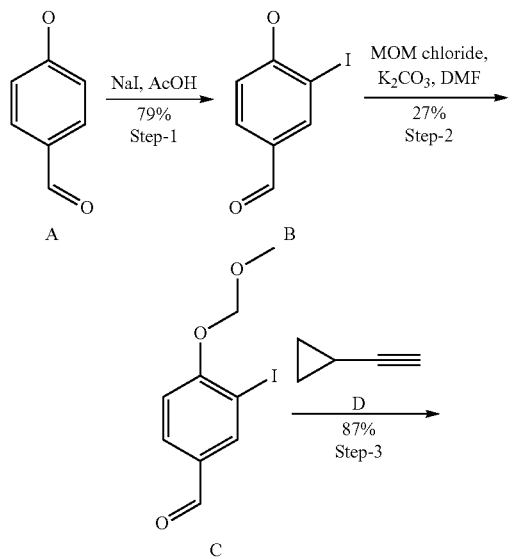

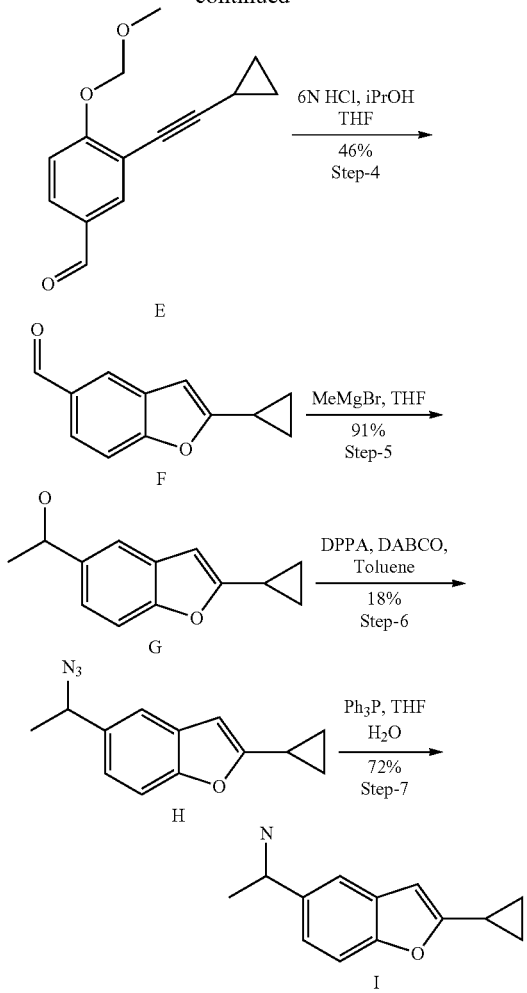

Step 1: Preparation of
4-hydroxy-3-iodo-benzaldehyde (B)

To a stirred solution of compound A (2 g, 16.4 mmol, 1 eq) in AcOH (30 mL) was added NIS (4.5 g, 19.7 mmol, 1.2 eq) in portions and the resulting mixture was stirred for 18 h at 23° C. The reaction mixture was filtered and the filtrate was diluted with ethyl acetate (100 mL). The ethyl acetate layer was washed with water (30 mL) and concentrated in vacuo to obtain the compound B (3.2 g, 79%) as white solid which was used in the next step without further purification.

$^1$H NMR (400 MHz, DMSO-d$_6$) δ 11.51 (s, 1H), 11.1 (br s, 1H), 8.23 (s, 1H), 7.02 (d, J=8 Hz, 1H), 6.92 (d, J=8 Hz, 1H);

LCMS: m/z=249.2 [M+H], RT=3.23 minutes; (Program R1, Column Y).

Step 2: Preparation of
3-iodo-4-methoxymethoxy-benzaldehyde (C)

To a stirred solution of compound B (3.2 g, 12.9 mmol, 1 eq) in dry DMF (15 mL) were added K$_2$CO$_3$ (7.12 g, 51.6 mmol, 4 eq) and MOM chloride (1.3 g, 15.5 mmol, 1.2 eq) in portions at 0° C. and the resulting mixture was stirred for 16 h at 23° C. The reaction mixture was diluted with ice-water (30 ml) and the organic components were extracted with ethyl acetate (100 ml). The organic layer was concentrated in vacuo and the crude material was purified by flash chromatography (Combiflash) using 100-200 mesh silica gel eluting with 20% ethylacetate/hexane to obtain the compound C (1 g, 27%) as white solid.

$^1$H NMR (400 MHz, DMSO-$d_6$) δ 9.83 (s, 1H), 8.31 (d, J=4 Hz, 1H), 7.91-7.88 (m, 1H), 7.27 (d, J=8 Hz, 1H), 5.40 (s, 2H), 3.41 (s, 3H);

LCMS: m/z=293.0 [M+H], RT=3.71 minutes; (Program R1, Column Y).

Step 3: Preparation of 3-cyclopropylethynyl-4-methoxymethoxy-benzaldehyde (E)

To a solution of compound C (200 mg, 0.68 mmol, 1 eq) in triethylamine (2 mL) in sealed tube were added compound D (50 mg, 0.75 mmol, 1.1 eq) and CuI (3 mg, 0.013 mmol, 0.02 eq) the mixture was degassed with argon for 15 minutes. PdCl$_2$(Ph$_3$P)$_2$ (10 mg, 0.013 mmol, 0.02 eq) was added to it and the resulting mixture was degassed with argon for 10 minutes and stirred at 50° C. for 18 h. The reaction mixture was cooled to RT, filtered and the filtrate was diluted with ethyl acetate (20 ml). The organic layer was washed with water (10 ml) and concentrated in vacuo. The crude material was purified by flash chromatography (Combiflash) using 100-200 mesh silica gel eluting with 10% ethyl acetate/hexane to obtain the compound E (140 mg, 87%) as white solid.

$^1$H NMR (400 MHz, DMSO-$d_6$) δ 9.83 (s, 1H), 7.87 (d, J=4 Hz, 1H), 7.73-7.70 (m, 1H), 7.19 (d, J=8 Hz, 1H), 5.30 (s, 2H), 3.51 (s, 3H), 1.53-1.46 (m, 1H), 0.92-0.87 (m, 2H), 0.85-0.82 (m, 2H);

LCMS: m/z=231.2 [M+H], RT=3.77 minutes; (Program R1, Column Y).

Step 4: Preparation of 2-cyclopropyl-benzofuran-5-carbaldehyde (F)

To a stirred solution of compound E (2.7 g, 11.74 mmol 1 eq) in a mixture of iPrOH (30 mL) and THF (30 mL) was added 6N aqueous HCl (30 mL) drop wise at 0° C. and the resulting mixture was stirred for 18 h at 23° C. The reaction mixture was concentrated in vacuo and the residue was diluted with ethyl acetate (100 ml). The ethyl acetate layer was washed with water (30 ml) and concentrated in vacuo. The crude material was purified by flash chromatography (Combiflash) using 100-200 mesh silica gel eluting with 20% ethylacetate/hexane to obtain the compound F (1 g, 46%) as white solid $^1$H NMR (400 MHz, DMSO-$d_6$) δ 10.01 (s, 1H), 8.08 (s, 1H), 7.78-7.76 (m, 1H), 7.65 (d, J=8 Hz, 1H), 6.75 (s, 1H), 2.20-2.13 (m, 1H), 1.10-1.00 (m, 2H), 0.98-0.95 (m, 2H).

Step 5: Preparation of 1-(2-cyclopropyl-benzofuran-5-yl)-ethanol (G)

To a stirred solution of compound F (1 g, 5.38 mmol, 1 eq) in dry THF (20 mL) was added methyl magnesium bromide (3M in diethyl ether 3.6 mL, 10.75 mmol, 2 eq) drop wise at −50° C. and the resulting mixture was stirred for 4 h at −50° C. The reaction mixture was quenched with saturated aq. NH$_4$Cl solution and the organic components were extracted with ethyl acetate (100 ml). The ethyl acetate layer was concentrated in vacuo to obtain the compound G (980 mg, 91%) as colorless sticky material which was used in the next step without further purification.

$^1$H NMR (400 MHz, DMSO-$d_6$) δ 7.42 (s, 1H), 7.35 (d, J=8 Hz, 1H), 7.16-7.14 (m, 1H), 6.52 (s, 1H), 5.093 (d, J=4 Hz, 1H), 4.79-4.74 (m, 1H), 2.12-2.05 (m, 1H), 1.329 (d, J=6 Hz, 3H), 1.01-0.96 (m, 2H), 0.87-0.84 (m, 2H);

LCMS: m/z=202.2 [M+H], RT=3.65 minutes; (Program R1, Column Y).

Step 6: Preparation of 5-(1-azido-ethyl)-2-cyclopropyl-benzofuran (H)

To a stirred solution of compound G (200 mg, 0.99 mmol, 1 eq) in dry toluene (5 mL) were added DPPA (327 mg, 1.19 mmol, 1.2 eq) and DABCO (134 mg, 1.19 mmol, 1.2 eq) at 0° C. for 2 h followed by at 23° C. 18 h. The reaction mixture was concentrated in vacuo and the crude material was purified by flash chromatography (Combiflash) using 100-200 mesh silica gel eluting with 10% ethyl acetate/hexane to obtain the compound H (40 mg, 18%) as colorless sticky material.

$^1$H NMR (400 MHz, DMSO-$d_6$) δ 7.51-7.45 (m, 2H), 7.33-7.32 (m, 1H), 7.22-7.20 (m, 1H), 4.89-4.88 (m, 1H), 1.47 (d, J=8 Hz, 3H), 1.29-1.27 (m, 1H), 1.01-0.99 (m, 2H), 0.89-0.88 (m, 2H).

Step 7: Preparation of 1-(2-cyclopropyl-benzofuran-5-yl)-ethylamine (I)

To a stirred solution of compound H (40 mg, 0.18 mmol, 1 eq) in a mixture of THF (50 mL) and H$_2$O (1 ml) was added triphenylphosphine (93 mg, 0.35 mmol, 2 eq) and the resulting mixture was stirred at 70° C. for 18 h. The reaction mixture was cooled to RT, concentrated in vacuo and the crude was purified by flash chromatography (Combiflash) using 100-200 mesh silica gel eluting with 10% methanol/dichloromethane to obtain the compound I (25 mg, 72%) as brown sticky material.

$^1$H NMR (400 MHz, DMSO-$d_6$) δ 7.45 (s, 1H), 7.33 (d, J=8 Hz, 1H), 7.19-7.17 (m, 1H), 6.51 (s, 1H), 4.08-4.03 (m, 1H), 2.11-2.06 (m, 1H), 1.26 (d, J=8 Hz, 3H), 1.01-0.96 (m, 2H), 0.87-0.83 (m, 2H);

LCMS: m/z=202.4 [M+H], RT=2.72 minutes; (Program R1, Column Y).

SCHEME-5: Synthesis of C-Cyclopropyl-C-(6-fluoro-quinolin-3-yl)-methylamine

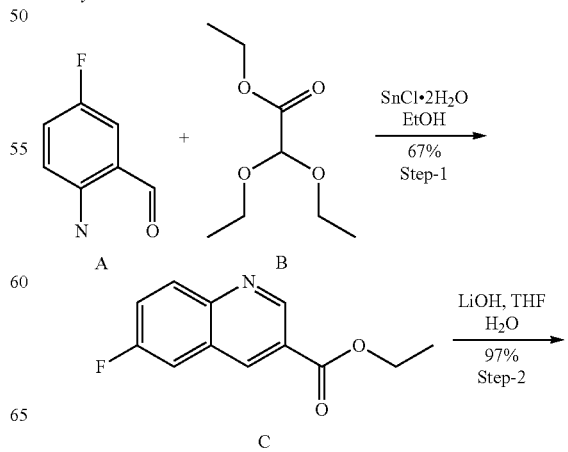

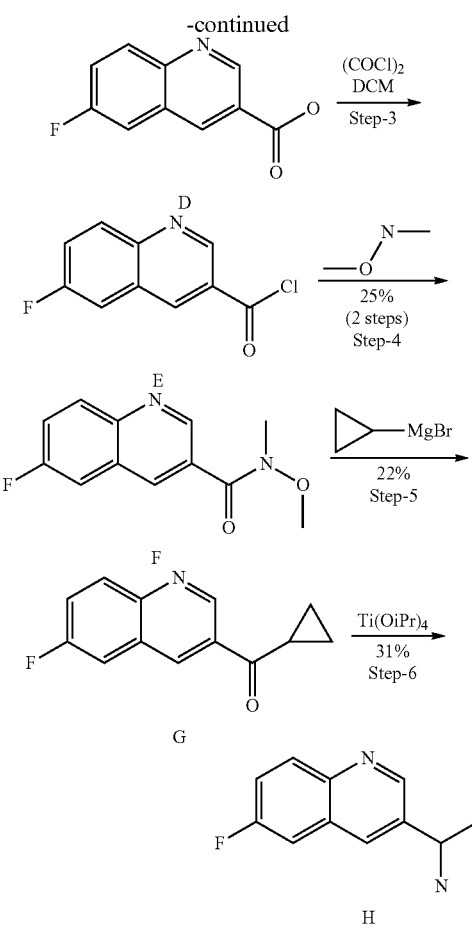

Step 1: Preparation of 6-fluoro-quinoline-3-carboxylic acid ethyl ester (C)

To a stirred solution of compound A (3 g, 17.74 mmol, 1 eq) in EtOH (100 mL) were added $SnCl_2.2H_2O$ (48 g, 212.9 mmol, 12 eq) and compound B (8.43 g, 44.34 mmol, 2.5 eq) drop wise and the resulting mixture was stirred at 70° C. for 12 h. The reaction mixture was concentrated in vacuo and the residue was diluted with water. The aqueous part was further diluted with saturated aq. $NaHCO_3$ solution (100 ml) and filtered. Organic components were extracted with ethyl acetate (300 ml) and the ethyl acetate layer was dried over anhydrous sodium sulfate and removed in vacuo. The crude residue was purified by flash chromatography (Combiflash) using 100-200 mesh silica gel and eluting with 30% ethyl acetate/hexane to obtain compound C (2.6 g, 67%) as white solid.

$^1$H NMR (400 MHz, DMSO-$d_6$) δ 9.29 (s, 1H), 9.01 (s, 1H), 8.20-8.16 (m, 1H), 8.07-8.04 (m, 1H), 7.87-7.82 (m, 1H), 4.42 (q, J=8 Hz, 2H), 1.38 (t, J=8 Hz, 3H);

LCMS: m/z=219.8 [M+H], RT=3.66 minutes; (Program R1, Column Y).

Step 2: Preparation of 6-fluoro-quinoline-3-carboxylic acid (D)

To a stirred solution of compound C (2.6 g, 11.9 mmol, 1 eq) in THF (60 mL) was added LiOH (1.5 g, 35.6 mmol, 3 eq) in water (10 mL) drop wise at 0° C. and the resulting mixture was stirred for 4 h at 23° C. The reaction mixture was concentrated in vacuo and the residue was diluted with water. The aqueous part was washed with ethyl acetate (20 mL) and then acidified with saturated aq. citric acid solution to pH 5. The organic components were extracted with ethyl acetate (200 mL), ethyl acetate layer was dried over anhydrous sodium sulfate and concentrated in vacuo to obtain the compound D (2.2 g, 97%) as gummy material which was used in the next step without further purification.

$^1$H NMR (400 MHz, DMSO-$d_6$) δ 9.28 (d, J=2 Hz, 1H), 8.97 (d, J=2 Hz, 1H), 8.19-8.15 (m, 1H), 8.04-8.01 (m, 1H), 7.85-7.79 (m, 1H);

LCMS: m/z=192.1 [M+H], RT=2.69 minutes; (Program R1, Column Y).

Step 3: Preparation of 6-fluoro-quinoline-3-carbonyl chloride (E)

To a stirred solution of compound D (2.2 g, 11.5 mmol, 1 eq) in dry $CH_2Cl_2$ (100 mL) was added oxalyl chloride (8.77 g, 69.1 mmol, 6 eq) drop wise at 0° C. and the resulting mixture was stirred for 4 h at 23° C. The reaction mixture was concentrated in vacuo under nitrogen atmosphere to obtain the compound E (2.4 g) as colorless liquid which was used in the next step without further purification.

Step 4: Preparation of 6-fluoro-quinoline-3-carboxylic acid methoxy-methyl-amide (F)

To a stirred solution of compound E (2.4 g, 11.5 mmol, 1 eq) in dry $CH_2Cl_2$ (100 mL) were added N,O-dimethylhydroxylamine hydrochloride (1.7 g, 17.2 mmol, 1.5 eq) and DIPEA (14.8 g, 114.8 mmol, 10 eq) drop wise at 0° C. and the resulting mixture was stirred for 18 h at 23° C. The reaction mixture was concentrated in vacuo and the residue was diluted with $CH_2Cl_2$ (200 ml). DCM layer was washed with water (50 ml) and concentrated in vacuo. The crude material was purified by flash chromatography (Combiflash) using 100-200 mesh silica gel eluting with 60% ethyl acetate/hexane to obtain the compound F (650 mg, 25%) as off white solid.

$^1$H NMR (400 MHz, DMSO-$d_6$) δ 9.03 (d, J=2 Hz, 1H), 8.66 (d, J=4 Hz, 1H), 8.16-8.12 (m, 1H), 7.95-7.92 (m, 1H), 7.80-7.75 (m, 1H), 3.65 (s, 3H), 3.35 (s, 3H);

LCMS: m/z=235.2 [M+H], RT=3.02 minutes; (Program R1, Column Y).

Step 5: Preparation of cyclopropyl-(6-fluoro-quinolin-3-yl)-methanone (G)

To a stirred solution of compound F (650 mg, 2.78 mmol, 1 eq) in dry THF (20 mL) was added cyclopropyl magnesium bromide (0.5 M in THF, 8.5 mL, 4.2 mmol, 1.5 eq) drop wise at −78° C. and the resulting mixture was stirred for 40 h at 23° C. The reaction mixture was quenched with saturated aq. $NH_4Cl$ solution and the organic components were extracted with ethyl acetate (50 ml). Ethyl acetate layer was concentrated in vacuo and the crude material was purified by flash chromatography (Combiflash) using 100-200 mesh silica gel eluting with 50% ethyl acetate/hexane to obtain the compound G (130 mg, 22%) as colorless sticky material $^1$H NMR (400 MHz, DMSO-$d_6$) δ 9.36 (d, J=2 Hz, 1H), 9.16 (d, J=2 Hz, 1H), 8.20-8.16 (m, 1H), 8.01-7.98 (m, 1H), 7.87-7.82 (m, 1H), 1.821.75 (m, 1H), 1.18-1.15 (m, 4H);

LCMS: m/z=215.9 [M+H], RT=3.51 minutes; (Program R1, Column Y).

Step 6: Preparation of cyclopropyl-C-(6-fluoro-quinolin-3-yl)-methylamine (H)

To a stirred solution of compound G (130 mg, 0.6 mmol, 1 eq) in methanolic ammonia (7 N, 10 mL) was added titanium isopropoxide (344 mg, 1.2 mmol, 2 eq) drop wise at 0° C. and the mixture was stirred for 12 h at 23° C. Sodium borohydride (35 mg, 0.9 mmol, 1.5 eq) was added in small portions to it at 0° C. and the resulting mixture was stirred for 18 h at 23° C. The reaction mixture was quenched with ice and was concentrated in vacuo. The crude material was purified by flash chromatography (Combiflash) using 100-200 mesh silica gel eluting with 10% methanol/dichloromethane to obtain the compound H (40 mg, 31%) as brown sticky material.

$^1$H NMR (400 MHz, DMSO-$d_6$) δ 8.96 (d, J=2 Hz, 1H), 8.27-8.29 (m, 1H), 8.07-8.03 (m, 1H), 7.76-7.73 (m, 1H), 7.63-7.58 (m, 1H), 4.40 (m, 1H), 2.20 (br s, 2H), 0.53-0.51 (m, 1H), 0.43-0.40 (m, 4H);

LCMS: m/z=217.2 [M+H], RT=2.00 minutes; (Program R1, Column Y).

SCHEME-6: Synthesis of 1-(1H-Indazol-3-yl)-ethylamine

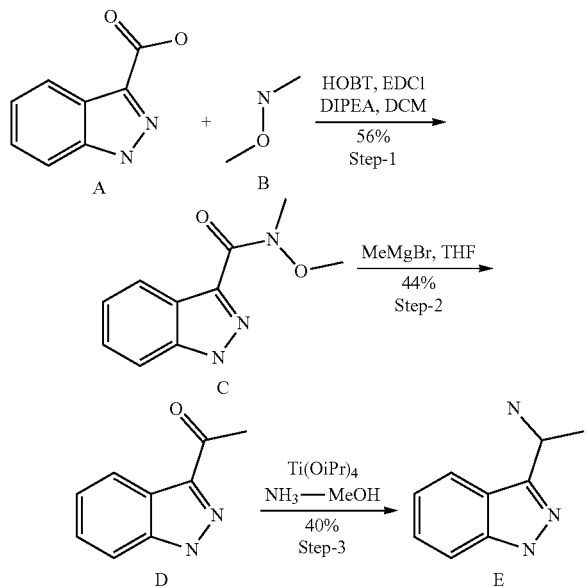

Step 1: Preparation of 1H-indazole-3-carboxylic acid methoxy-methyl-amide (C)

To a stirred solution of compound A (1 g, 6.2 mmol, 1 eq) in CH$_2$Cl$_2$ (30 mL) were added compound B (903 mg, 9.25 mmol, 1.5 eq), HOBT (1 g, 7.4 mmol, 1.2 eq) and EDCI (2.4 g, 12.3 mmol, 2 eq) at 0° C. DIPEA (4 g, 30.8 mmol, 5 eq) was added to it at 0° C. and the resulting mixture was stirred for 18 h at 23° C. The reaction mixture was diluted with CH$_2$Cl$_2$ (100 ml) and DCM layer was washed with water (30 ml). DCM layer was removed in vacuo and the crude residue was purified by flash chromatography (Combiflash) using 100-200 mesh silica gel and eluting with 50% ethyl acetate/hexane to obtain the compound C (700 mg, 56%) as off white solid.

$^1$H NMR (400 MHz, DMSO-$d_6$) δ 13.60 (s, 1H) 8.00 (d, J=8 Hz, 1H), 7.61 (d, J=8 Hz, 1H), 7.41 (t, J=8 Hz, 1H), 7.23 (t, J=8 Hz, 1H), 3.78 (s, 3H), 3.45 (s, 3H);

LCMS: m/z=206.2 [M+H], RT=2.55 minutes; (Program R1, Column W).

Step 2: Preparation of 1-(1H-indazol-3-yl)-ethanone (D)

To a stirred solution of compound C (700 mg, 3.4 mmol, 1 eq) in dry THF (40 mL) was added methyl magnesium bromide (1 M in diethyl ether, 11 mL, 10.2 mmol, 3 eq) drop wise at 0° C. and the resulting mixture was stirred for 18 h at 23° C. The reaction mixture was quenched with saturated aq. NH$_4$Cl solution and the organic components were extracted with ethyl acetate (100 ml). Ethyl acetate layer was concentrated in vacuo and the crude material was purified by flash chromatography (Combiflash) using 100-200 mesh silica gel eluting with 40% ethyl acetate/hexane to obtain the compound D (250 mg, 44%) as colorless sticky material.

$^1$H NMR (400 MHz, DMSO-$d_6$) δ 13.82 (s, 1H), 8.17 (d, J=8 Hz, 1H), 7.66 (d, J=8 Hz, 1H), 7.47-7.43 (m, 1H), 7.31 (t, J=8 Hz, 1H), 2.63 (s, 3H);

LCMS: m/z=161.1 [M+H], RT=2.94 minutes; (Program R1, Column W).

Step 3: Preparation of 1-(1H-indazol-3-yl)-ethylamine (E)

To a stirred solution of compound D (250 mg, 1.56 mmol, 1 eq) in methanolic ammonia (7 N, 10 mL) was added titanium isopropoxide (890 mg, 3.12 mmol, 2 eq) drop wise at 0° C. and the mixture was stirred for 6 h at 23° C. Sodium borohydride (90 mg, 2.34 mmol, 1.5 eq) was added to it in small portions at 0° C. and the resulting mixture was stirred for 18 h at 23° C. The reaction mixture was quenched with ice and concentrated in vacuo. The crude material was purified by flash chromatography (Combiflash) using 100-200 mesh silica gel eluting with 10% methanol/dichloromethane to obtain the compound E (100 mg, 40%) as brown sticky material $^1$H NMR (400 MHz, DMSO-$d_6$) δ 12.61 (s, 1H), 7.93 (d, J=8 Hz, 1H), 7.44 (d, J=8 Hz, 1H), 7.29 (t, J=8 Hz, 1H), 7.04 (t, J=8 Hz, 1H), 4.42-4.37 (m, 1H), 1.45 (d, J=8 Hz, 3H);

LCMS: m/z=162.3 [M+H], RT=0.57 minutes; (Program R1, Column W).

SCHEME-7: Synthesis of C-Cyclopropyl-C-imidazo[1,2-a]pyridin-6-yl methylamine

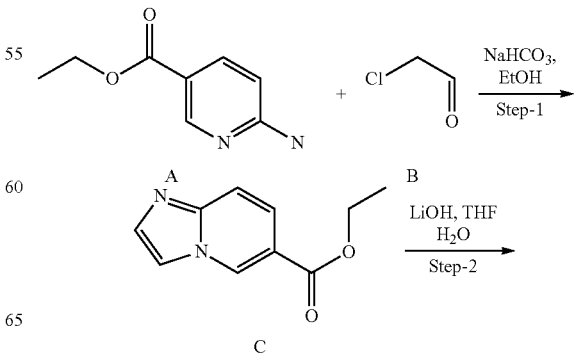

-continued

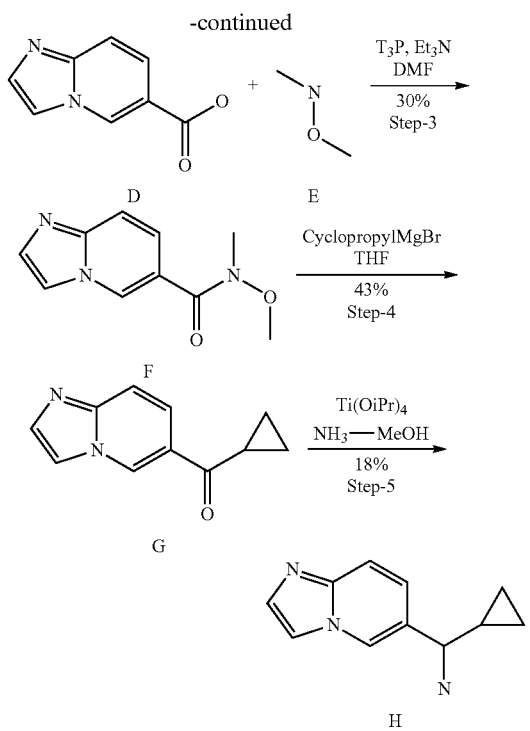

Step 1: Preparation of imidazo[1,2-a]pyridine-6-carboxylic acid ethyl ester (C)

To a stirred solution of compound A (3.2 g, 19.3 mmol, 1 eq) in EtOH (300 mL) were added NaHCO$_3$ (32.4 g, 385.5 mmol, 20 eq) and compound B (~55% aq. solution, 30 ml, 192.8 mmol, 10 eq) at 23° C. and the resulting mixture was heated to 70° C. for 18 h. The reaction mixture was cooled to RT, filtered and the filtrated was concentrated in vacuo and the residue was diluted with ethyl acetate (200 ml). Ethyl acetate layer was washed with water (50 ml), dried over anhydrous Na$_2$SO$_4$, concentrated in vacuo to obtain the compound C (3.7 g) which was used in the next step without further purification.

LCMS: m/z=190.7 [M+H], RT=0.62 minutes; (Program R1, Column W).

Step 2: Preparation of imidazo[1,2-a]pyridine-6-carboxylic acid (D)

To a stirred solution of compound C (3.7 g, 19.5 mmol, 1 eq) in THF (45 mL) was added a solution of LiOH (2.5 g, 58.4 mmol, 3 eq) in water (5 mL) drop wise at 0° C. and the resulting mixture was stirred for 18 h at 23° C. The reaction mixture was concentrated in vacuo and the residue was diluted with water. The aqueous part was washed with ethyl acetate (20 mL), acidified with saturated aq. citric acid solution to pH 5. The organic components were extracted from the aq. part with 10% MeOH/CH$_2$Cl$_2$ (100 mL) and the organic layer was concentrated in vacuo to obtain the compound D (3 g) as off white solid which was used in the next step without further purification.

LCMS: m/z=163.1 [M+H], RT=0.40 minutes; (Program R1, Column W).

Step 3: Preparation of imidazo[1,2-a]pyridine-6-carboxylic acid methoxy-methyl-amide (F)

To a stirred solution of compound D (2.5 g, 15.4 mmol, 1 eq) in DMF (50 mL) were added compound E (2.3 g, 23.1 mmol, 1.5 eq), triethylamine (15.6 g, 154.3 mmol, 10 eq) and T3P (~50% in ethyl acetate, 14.8 g, 23.1 mmol, 1.5 eq) at 23° C. and the resulting mixture was heated at 120° C. for 18 h. The reaction mixture was cooled to RT, quenched with water and the organic components were extracted with 10% methanol/CH$_2$Cl$_2$. The organic layer was concentrated in vacuo and the crude material was purified by flash chromatography (Combiflash) using 100-200 mesh silica gel eluting with 10% MeOH/CH$_2$Cl$_2$ to obtain the compound F (600 mg, 20%) as off white solid.

$^1$H NMR (400 MHz, DMSO-d$_6$) δ 9.03 (s, 1H), 8.06 (s, 1H), 7.64 (m, 1H), 7.59 (d, J=8 Hz, 1H), 7.47-7.44 (m, 1H), 3.61 (s, 3H), 3.32 (s, 3H);

LCMS: m/z=206.2 [M+H], RT=0.54 minutes; (Program R1, Column W).

Step 4: Preparation of cyclopropyl-imidazo[1,2-a]pyridin-6-yl-methanone (G)

To a stirred solution of compound F (600 mg, 2.9 mmol, 1 eq) in dry THF (30 mL) was added cyclopropyl magnesium bromide (0.5 M in THF, 12 mL, 5.8 mmol, 2 eq) drop wise at 0° C. and the resulting mixture was stirred for 18 h at 23° C. The reaction mixture was quenched with saturated aq. NH$_4$Cl solution and the organic components were extracted with ethyl acetate (50 ml). Ethyl acetate layer was concentrated in vacuo and the crude material was purified by flash chromatography (Combiflash) using 100-200 mesh silica gel eluting with 10% MeOH/CH$_2$Cl$_2$ to obtain the compound G (230 mg, 43%) as colorless sticky material $^1$H NMR (400 MHz, DMSO-d$_6$) δ 9.63 (s, 1H), 8.07 (s, 1H), 7.70 (m, 2H), 7.63 (m, 1H), 1.78 (m, 1H), 0.75-0.90 (m, 4H);

LCMS: m/z=187.2 [M+H], RT=0.60 minutes; (Program R1, Column W).

Step 5: Preparation of C-cyclopropyl-C-imidazo[1,2-a]pyridin-6-yl-methylamine (H)

To a stirred solution of compound G (230 mg, 1.2 mmol, 1 eq) in methanolic ammonia (7 N, 10 mL) was added titanium isopropoxide (703 mg, 2.47 mmol, 2 eq) drop wise at 0° C. and the mixture was stirred for 18 h at 23° C. Sodium borohydride (71 mg, 1.85 mmol, 1.5 eq) was added to it in small portions at 0° C. and the resulting mixture was stirred for 18 h at 23° C. The reaction mixture was quenched with ice and concentrated in vacuo. The crude residue was purified by flash chromatography (Combiflash) using 100-200 mesh silica gel eluting with 10% methanol/dichloromethane to obtain the compound H (40 mg, 18%) as brown sticky material.

$^1$H NMR (400 MHz, DMSO-d$_6$) δ 8.52 (s, 1H), 7.92 (s, 1H), 7.56-7.54 (m, 2H), 7.39-7.37 (m, 1H), 4.00-4.20 (m, 1H), 1.00-1.20 (m, 1H), 0.58 (m, 1H), 0.47-0.40 (m, 2H), 0.25-0.35 (m, 1H);

LCMS: m/z=188.2 [M+H], RT=0.38 minutes; (Program R1, Column W).

SCHEME-8: Synthesis of C-Cyclopropyl-C-(6-phenyl-pyridin-3-yl)-methylamine

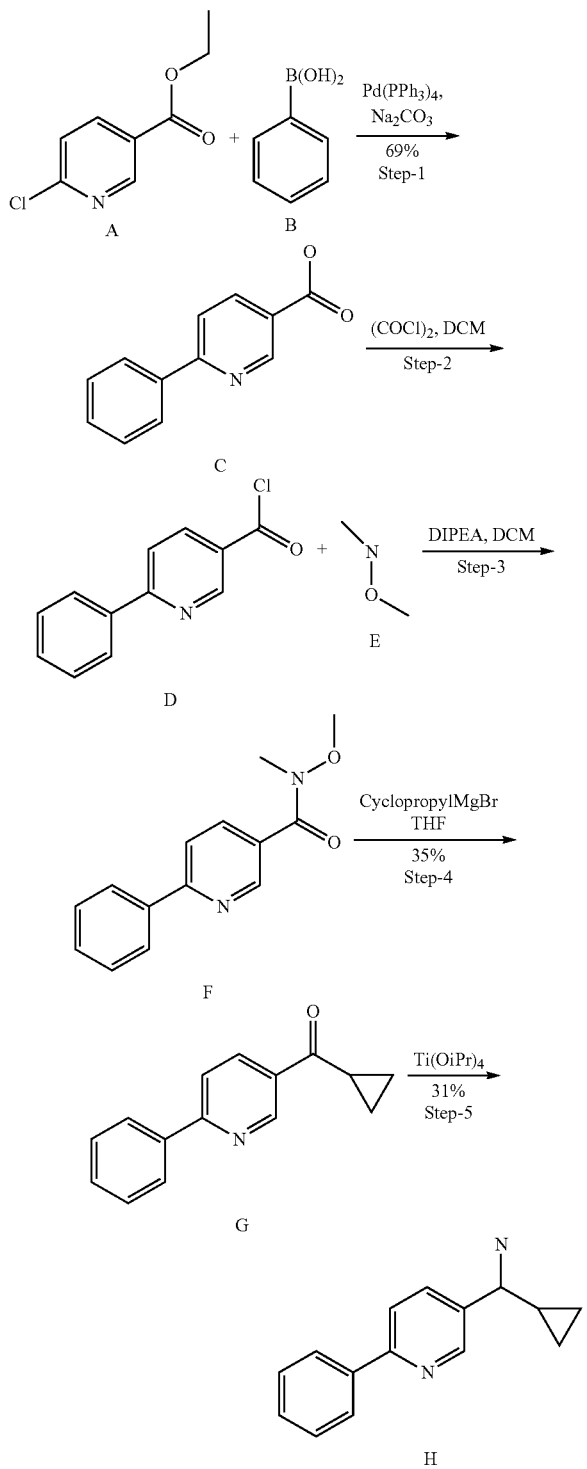

Step 1: Preparation of 6-phenyl-nicotinic acid (C)

To a stirred solution of compound A (3 g, 16.16 mmol, 1 eq) in a mixture of dioxane and water (150 mL, 4:1) mixture were added compound B (3 g, 24.2 mmol, 1.5 eq) and sodium carbonate (8.6 g, 80.8 mmol, 5 eq) and the mixture was degassed with argon for 30 minutes. Pd(Ph$_3$P)$_4$ (1.9 g, 1.62 mmol, 0.1 eq) was added to it and the resulting mixture was further degassed with argon for another 10 minutes and stirred at 110° C. for 18 h. The reaction mixture was filtered and the filtrate was concentrated in vacuo. The residue was diluted with water (30 mL) and washed with ethyl acetate (20 mL). The aq. part was acidified with saturated aq. citric acid solution to pH 5. The organic components were extracted with 10% MeOH/CH$_2$Cl$_2$ (100 mL) and the organic layer was concentrated in vacuo to obtain the compound C (2.2 g, 69%) as white solid which was used in the next step without further purification.

$^1$H NMR (400 MHz, DMSO-d$_6$) δ 13.4 (br s, 1H), 9.14 (d, J=2 Hz, 1H), 8.33-8.31 (m, 1H), 8.17-8.15 (m, 2H), 8.10 (d, J=8 Hz, 1H), 7.55-7.48 (m, 3H);

LCMS: m/z=200.1 [M+H], RT=3.21 minutes; (Program R1, Column Y).

Step 2: Preparation of 6-phenyl-nicotinoyl chloride (D)

To a stirred solution of compound C (2.2 g, 11.05 mmol, 1 eq) in dry CH$_2$Cl$_2$ (50 mL) was added oxalyl chloride (8.42 g, 66.33 mmol, 6 eq) drop wise at 0° C. and the resulting mixture was stirred for 4 h at 23° C. The reaction mixture was concentrated in vacuo under nitrogen atmosphere to obtain the compound D (2.4 g) as colorless liquid which was used in the next step without further purification.

Step 3: Preparation of N-methoxy-N-methyl-6-phenyl-nicotinamide (F)

To a stirred solution of compound D (2.4 g, 11.06 mmol, 1 eq) in dry CH$_2$Cl$_2$ (100 mL) were added compound E (N,O-dimethylhydroxylamine hydrochloride) (1.62 g, 16.6 mmol, 1.5 eq) and DIPEA (14.3 g, 110.6 mmol, 10 eq) drop wise at 0° C. and the resulting mixture was stirred for 18 h at 23° C. The reaction mixture was concentrated in vacuo and the residue was diluted with CH$_2$Cl$_2$ (200 ml). The organic layer was washed with water (50 ml) and concentrated in vacuo to obtain the compound F (3.1 g) which was used in the next step without further purification.

$^1$H NMR (400 MHz, DMSO-d$_6$) δ 8.885-8.882 (m, 1H), 8.15-8.13 (m, 2H), 8.11-8.09 (m, 1H), 8.07-8.05 (m, 1H), 7.54-7.48 (m, 3H), 3.60 (s, 3H), 3.31 (s, 3H);

LCMS: m/z=243.2 [M+H], RT=3.37 minutes; (Program R1, Column Y).

Step 4: Preparation of cyclopropyl-(6-phenyl-pyridin-3-yl)-methanone (G)

To a stirred solution of compound F (1 g, 4.13 mmol, 1 eq) in dry THF (20 mL) was added cyclopropyl magnesium bromide (0.5 M in THF, 12.5 mL, 6.2 mmol, 1.5 eq) drop wise at −40° C. and the resulting mixture was stirred for 18 h at 23° C. The reaction mixture was quenched with saturated aq. NH$_4$Cl solution and the organic components were extracted with ethyl acetate (100 ml). Ethyl acetate layer was concentrated in vacuo and the crude residue was purified by flash chromatography (Combiflash) using 100-200 mesh silica gel eluting with 50% ethylacetate/hexane to obtain the compound G (320 mg, 35%) as colorless sticky material.

$^1$H NMR (400 MHz, DMSO-d$_6$) δ 9.32-9.31 (m, 1H), 8.46-8.43 (m, 1H), 8.20-8.14 (m, 3H), 7.57-7.51 (m, 3H), 3.02-2.99 (m, 1H), 1.11-1.09 (m, 4H);

LCMS: m/z=223.7 [M+H], RT=3.85 minutes; (Program R1, Column Y).

Step 5: Preparation of cyclopropyl-C-(6-phenyl-pyridin-3-yl)-methylamine (H)

To a stirred solution of compound G (320 mg, 1.43 mmol, 1 eq) in methanolic ammonia (7 N, 10 mL) was added titanium isopropoxide (816 mg, 2.87 mmol, 2 eq) drop wise at 0° C. and the mixture was stirred for 8 h at 23° C. Sodium borohydride (82 mg, 2.15 mmol, 1.5 eq) was added to it in small portions at 0° C. and the resulting mixture was stirred for 18 h at 23° C. The reaction mixture was quenched with ice and concentrated in vacuo. The crude residue was purified by flash chromatography (Combiflash) using 100-200 mesh silica gel eluting with 10% methanol/dichloromethane to obtain the compound H (100 mg, 31%) as colorless sticky material $^1$H NMR (400 MHz, DMSO-$d_6$) δ 8.66 (s, 1H), 8.06 (d, J=8 Hz, 2H), 7.90 (s, 2H), 7.48 (t, J=8 Hz, 2H), 7.43-7.39 (m, 1H), 4.40 (br s, 1H), 1.06-0.98 (m, 1H), 0.52-0.46 (m, 1H), 0.41-0.40 (m, 3H);

LCMS: m/z=224.8 [M+H], RT=1.83 minutes; (Program R1, Column Y).

SCHEME-9: Synthesis of C-Cyclopropyl-C-(6-cyclopropylmethoxy-pyridin-3-yl)-methylamine

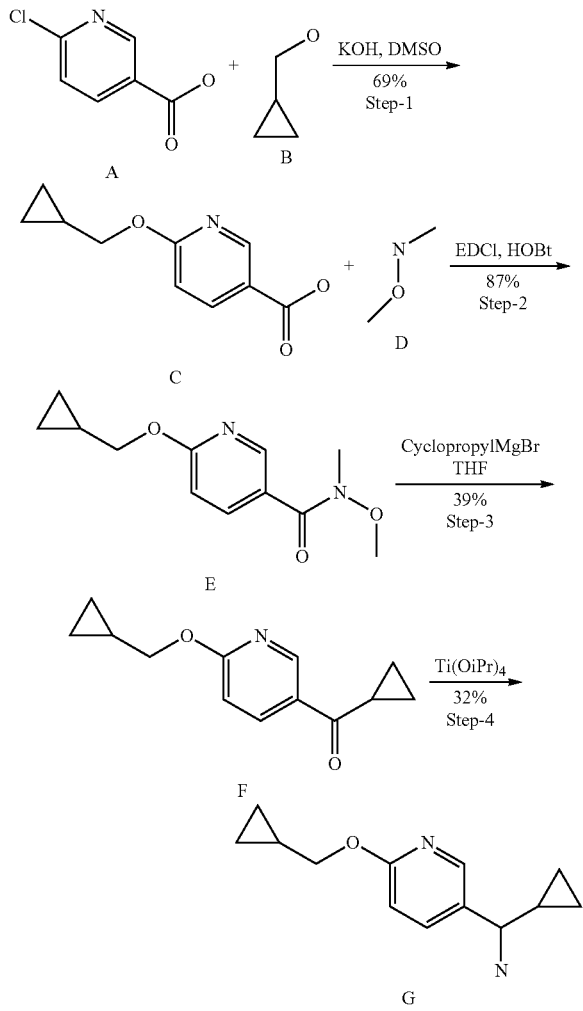

Step 1: Preparation of 6-cyclopropylmethoxy-nicotinic acid (C)

To a stirred solution of compound A (5 g, 31.7 mmol, 1 eq) in DMSO (100 mL) were added KOH (5.3 g, 95.2 mmol, 3 eq) and compound B (3.43 g, 47.6 mmol, 1.5 eq) at 23° C. and the resulting mixture was heated for 40 h at 100° C. The reaction mixture was cooled to RT, diluted with water (50 mL) and acidified with 6 N aq. HCl to pH 4. The organic components were extracted with ethyl acetate (100 mL) and the ethyl acetate layer was concentrated in vacuo to obtain the compound C (4.2 g, 69%) as off white solid.

$^1$H NMR (400 MHz, DMSO-$d_6$) δ 13.00 (s, 1H), 8.69 (d, J=4 Hz, 1H), 8.13-8.11 (m, 1H), 6.89 (d, J=8 Hz, 1H), 4.16 (d, J=8 Hz, 2H), 1.28-1.21 (m, 1H), 0.57-0.53 (m, 2H), 0.35-0.31 (m, 2H);

LCMS: m/z=194.0[M+H], RT=3.35 minutes; (Program R1, Column Y).

Step 2: Preparation of 6-cyclopropylmethoxy-N-methoxy-N-methyl-nicotinamide (E)

To a stirred solution of compound C (500 mg, 2.6 mmol, 1 eq) in $CH_2Cl_2$ (10 mL) were added compound D (380 mg, 3.89 mmol, 1.5 eq), HOBT (420 mg, 3.1 mmol, 1.2 eq) and EDCI (1 g, 5.18 mmol, 2 eq) respectively at 0° C. DIPEA (1.7 g, 12.9 mmol, 1.2 eq) was added to it at 0° C. and the resulting mixture was stirred for 18 h at 23° C. The reaction mixture was diluted with $CH_2Cl_2$ (50 ml) and the DCM layer was washed with water (20 ml). DCM was concentrated in vacuo and the crude material was purified by flash chromatography (Combiflash) using 100-200 mesh silica gel eluting with 50% ethyl acetate/hexane to obtain the compound E (530 mg, 87%) as off white solid $^1$H NMR (400 MHz, DMSO-$d_6$) δ 8.45 (d, J=4 Hz, 1H), 7.96-7.93 (m, 1H), 6.87 (d, J=8 Hz, 1H), 4.14 (d, J=8 Hz, 2H), 3.56 (s, 3H), 3.25 (s, 3H), 1.26-1.23 (m, 1H), 0.57-0.53 (m, 2H), 0.34-0.31 (m, 2H);

LCMS: m/z=237.2 [M+H], RT=3.42 minutes; (Program R1, Column Y).

Step 3: Preparation of cyclopropyl-(6-cyclopropyl-methoxy-pyridin-3-yl)-methanone (F)

To a stirred solution of compound E (530 mg, 2.2 mmol, 1 eq) in dry THF (20 mL) was added cyclopropyl magnesium bromide (0.5 M in THF, 6.8 mL, 3.37 mmol, 1.5 eq) drop wise at −78° C. and the resulting mixture was stirred for 18 h at 23° C. The reaction mixture was quenched with saturated aq. $NH_4Cl$ solution and the organic components were extracted with ethyl acetate (100 ml). The organic layer was concentrated in vacuo and the crude residue was purified by flash chromatography (Combiflash) using 100-200 mesh silica gel eluting with 40% ethyl acetate/hexane to obtain the compound F (190 mg, 39%) as colorless sticky material.

$^1$H NMR (400 MHz, DMSO-$d_6$) δ 8.93 (d, J=2 Hz, 1H), 8.25-8.22 (m, 1H), 6.93 (d, J=8 Hz, 1H), 4.20 (d, J=8 Hz, 2H), 2.91-2.85 (m, 1H), 1.29-1.23 (m, 1H), 1.03-1.01 (m, 4H), 0.58-0.54 (m, 2H), 0.36-0.35 (m, 2H);

LCMS: m/z=218.4 [M+H], RT=3.86 minutes; (Program R1, Column Y).

Step 4: Preparation of C-cyclopropyl-C-(6-cyclopropylmethoxy-pyridin-3-yl)-methylamine (G)

To a stirred solution of compound F (190 mg, 0.87 mmol, 1 eq) in methanolic ammonia (7 N, 15 mL) was added titanium isopropoxide (498 mg, 1.75 mmol, 2 eq) drop wise at 0° C. and the mixture was stirred for 18 h at 23° C. Sodium borohydride (50 mg, 1.31 mmol, 1.5 eq) was added to it in small portions at 0° C. and the resulting mixture was stirred for 18 h at 23° C. The reaction mixture was quenched with ice and concentrated in vacuo. The crude residue was purified by flash chromatography (Combiflash) using 100-200 mesh silica gel eluting with 10% methanol/dichloromethane to obtain the compound G (60 mg, 32%) as brown sticky material.

$^1$H NMR (400 MHz, DMSO-$d_6$) δ 8.07 (d, J=4 Hz, 1H), 7.75-7.72 (m, 1H), 6.74 (d, J=8 Hz, 1H), 4.41 (br s, 2H), 4.05 (d, J=7 Hz, 2H), 3.12 (d, J=8 Hz, 1H), 1.20-1.19 (m, 1H), 0.96-0.92 (m, 1H), 0.55-0.50 (m, 2H), 0.47-0.42 (m, 1H), 0.35-0.28 (m, 4H), 0.25-0.18 (m, 1H);

LCMS: m/z=219.2 [M+H], RT=2.27 minutes; (Program R1, Column Y).

SCHEME-10: Synthesis of 1-Benzo[b]thiophen-5-yl-ethylamine

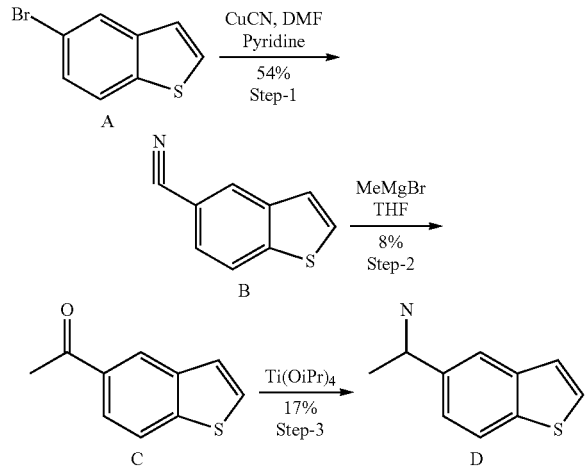

Step 1: Preparation of benzo[b]thiophene-5-carbonitrile (B)

To a stirred solution of compound A (500 mg, 2.35 mmol, 1 eq) in DMF (7 mL) in a sealed tube were added CuCN (273 mg, 3.05 mmol, 1.3 eq) and pyridine (0.25 mL) respectively. The resulting mixture was degassed with argon for 30 minutes and stirred for 10 h at 170° C. The reaction mixture was cooled to RT and quenched with a solution of ethylene diamine (0.25 mL) in water (6 mL) and the organic components were extracted with ethyl acetate (60 ml). The organic layer was concentrated in vacuo and the crude material was purified by flash chromatography (Combiflash) using 100-200 mesh silica gel eluting with 10% ethyl acetate/hexane to obtain the compound B (200 mg, 54%) as off white solid.

$^1$H NMR (400 MHz, DMSO-$d_6$) δ 8.43 (s, 1H), 8.26 (d, J=8 Hz, 1H), 7.99 (2, J=8 Hz, 1H), 7.73-7.71 (m, 1H), 7.58 (d, J=6 Hz, 1H).

Step 2: Preparation of 1-benzo[b]thiophen-5-yl-ethanone (C)

To a stirred solution of compound B (500 mg, 3.14 mmol, 1 eq) in dry THF (20 mL) was added methyl magnesium bromide (3 M in diethyl ether, 3.14 mL, 9.42 mmol, 3 eq) drop wise at −78° C. and the resulting mixture was stirred for 18 h at 23° C. The reaction mixture was quenched with saturated aq. NH$_4$Cl solution and the organic components were extracted with ethyl acetate (100 ml). The organic layer was concentrated in vacuo and the crude residue was purified by flash chromatography (Combiflash) using 100-200 mesh silica gel eluting with 40% ethyl acetate/hexane to obtain the compound F (45 mg, 8%) as colorless sticky material.

$^1$H NMR (400 MHz, DMSO-$d_6$) δ 8.55 (d, J=1 Hz, 1H), 8.13 (d, J=8 Hz, 1H), 7.92-7.88 (m, 2H), 7.62 (d, J=6 Hz, 1H), 2.65 (s, 3H).

Step 3: Preparation of 1-benzo[b]thiophen-5-yl-ethylamine (D)

To a stirred solution of compound C (300 mg, 1.70 mmol, 1 eq) in methanolic ammonia (7 N, 10 mL) was added titanium isopropoxide (970 mg, 3.41 mmol, 2 eq) drop wise at 0° C. and the mixture was stirred for 5 h at 23° C. Sodium borohydride (78 mg, 2.04 mmol, 1.2 eq) was added to it in small portions at 0° C. and the resulting mixture was stirred for 18 h at 23° C. The reaction mixture was quenched with ice and concentrated in vacuo. The crude residue was purified by flash chromatography (Combiflash) using 100-200 mesh silica gel eluting with 10% methanol/dichloromethane to obtain the compound G (50 mg, 17%) as brown sticky material.

$^1$H NMR (400 MHz, DMSO-$d_6$) δ 7.91 (d, J=8 Hz, 1H), 7.85 (s, 1H), 7.72 (d, J=8 Hz, 1H), 7.42-7.38 (m, 2H), 4.15-4.13 (m, 1H), 2.82 (br s, 2H), 1.31 (d, J=8 Hz, 3H);

LCMS: m/z=178.2 [M+H], RT=2.09 minutes; (Program R1, Column Y).

SCHEME-11: Synthesis of 1-(4-Ethoxy-phenyl)-ethylamine

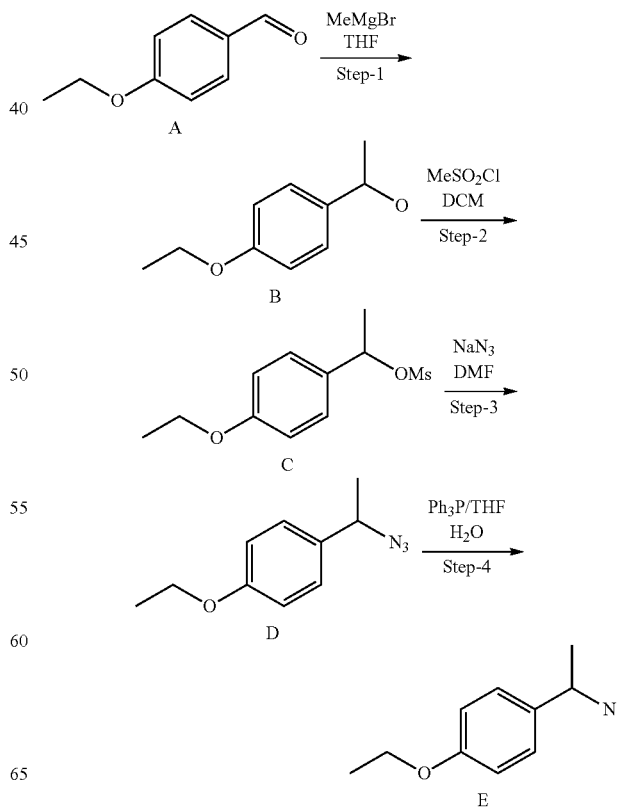

Step 1: Preparation of 1-(4-ethoxy-phenyl)-ethanol (B)

To a stirred solution of compound A (500 mg, 3.33 mmol, 1 eq) in dry THF (20 mL) was added methyl magnesium bromide (3 M in diethyl ether, 3.33 mL, 9.99 mmol, 3 eq) drop wise at −78° C. and the resulting mixture was stirred for 3 h at 23° C. The reaction mixture was quenched with saturated aq. NH$_4$Cl solution and the organic components were extracted with ethyl acetate (60 ml). Ethyl acetate layer was concentrated in vacuo and the crude residue was purified by flash chromatography (Combiflash) using 100-200 mesh silica gel eluting with 3% ethyl acetate/hexane to obtain the compound F (400 mg) as colorless sticky material.

$^1$H NMR (400 MHz, DMSO-d$_6$) δ 7.22 (d, J=8 Hz, 2H), 6.84 (d, J=8 Hz, 2H), 4.99 (d, J=4 Hz, 1H), 4.67-4.61 (m, 1H), 4.01-3.96 (m, 2H), 1.32-1.27 (m, 6H).

Step 2: Preparation of methanesulfonic acid 1-(4-ethoxy-phenyl)-ethyl ester (C)

To a stirred solution of compound B (400 mg, 2.4 mmol, 1 eq) in dry CH$_2$Cl$_2$ (15 mL) were added triethyl amine (0.5 mL, 3.61 mmol, 1.5 eq) followed by methane sulphonyl chloride (0.3 mL, 3.61 mmol, 1.5 eq) drop wise at 0° C. and the resulting mixture was stirred for 14 h at 23° C. The reaction mixture was quenched with water and the organic components were extracted with CH$_2$Cl$_2$ (50 ml). DCM layer was concentrated in vacuo to obtain the compound C (600 mg) as brownish sticky material which was used in the next step without further purification.

Step 3: Preparation of 1-(1-azido-ethyl)-4-ethoxy-benzene (D)

To a stirred solution of compound C (600 mg, 2.45 mmol, 1 eq) in dry DMF (7 mL) was added sodium azide (1.9 g, 28.7 mmol, 12 eq) portion wise at 0° C. and the resulting mixture was stirred for 14 h at 23° C. The reaction mixture was quenched with ice and the organic components were extracted with ethyl acetate (100 ml). Ethyl acetate was concentrated in vacuo to obtain the compound D (600 mg) as brownish sticky material which was used in the next step without further purification.

Step 4: Preparation of 1-(4-Ethoxy-phenyl)-ethylamine (E)

To a stirred solution of compound D (600 mg, 3.11 mmol, 1 eq) in a mixture of THF (20 mL) and H$_2$O (2 ml) was added triphenylphosphine (1.62 g, 6.22 mmol, 2 eq) and the resulting mixture was stirred at 70° C. for 18 h. The reaction mixture was concentrated in vacuo and the crude residue was purified by flash chromatography (Combiflash) using 100-200 mesh silica gel eluting with 10% methanol/dichloromethane to obtain the compound E (30 mg) as brown sticky material.

$^1$H NMR (400 MHz, DMSO-d$_6$) δ 7.35 (d, J=8 Hz, 2H), 6.93 (d, J=8 Hz, 2H), 4.26-4.21 (m, 1H), 4.04-3.99 (m, 2H), 1.40 (d, J=8 Hz, 3H), 1.35-1.29 (m, 3H).

SCHEME-12: Synthesis of C-[1-(4-Chloro-phenyl)-cyclobutyl]-methylamine

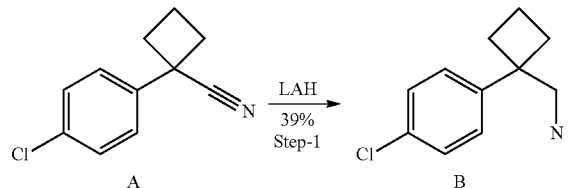

Step 1: Preparation of C-[1-(4-chloro-phenyl)-cyclobutyl]-methylamine (B)

To a stirred solution of compound A (200 mg, 1.04 mmol, 1 eq) in dry THF (8 mL) was added lithium aluminium hydride (1 M in THF, 2.1 mL, 2.09 mmol, 2 eq) drop wise at 0° C. and the resulting mixture was stirred for 1 h at 0° C. The reaction mixture was quenched with solid sodium sulfate decahydrate and filtered through Celite. The organic components were extracted with ethyl acetate (100 mL) and the organic layer was concentrated in vacuo to obtain the compound B (80 mg, 39%) as colorless sticky material which was used in the next step without further purification.

$^1$H NMR (400 MHz, DMSO-d$_6$) δ 7.33 (d, J=8 Hz, 2H), 7.09 (d, J=8 Hz, 2H), 2.73 (s, 2H), 2.18-2.11 (m, 4H), 2.00-1.93 (m, 1H), 1.78-1.74 (m, 1H);

LCMS: m/z=196.2 [M+H], RT=2.53 minutes; (Program R1, Column Y).

SCHEME-13: Synthesis of C-Quinolin-3-yl-methylamine

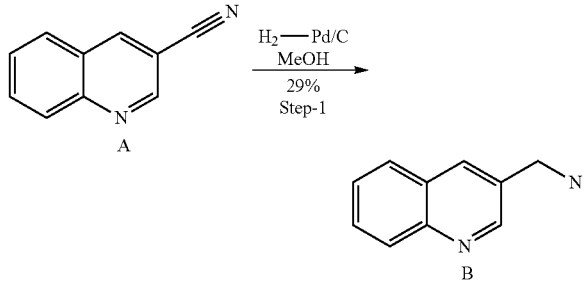

Step 1: Preparation of C-quinolin-3-yl-methylamine (B)

To a stirred solution of compound A (250 mg, 1.58 mmol, 1 eq) in MeOH (15 mL) was added Pd/C (10% Pd, 10 mg) and the resulting mixture was stirred for 18 h at 23° C. under hydrogen atmosphere. The reaction mixture was filtered through Celite and the filtrate was concentrated in vacuo. The crude residue was purified by flash chromatography (Combiflash) using 100-200 mesh silica gel eluting with 30% methanol/dichloromethane to obtain the compound B (75 mg, 29%) as colorless sticky material.

$^1$H NMR (400 MHz, DMSO-d$_6$) δ 8.88 (d, J=2 Hz, 1H), 8.22 (s, 1H), 7.99 (d, J=8 Hz, 1H), 7.93 (d, J=8 Hz, 1H), 7.71-7.68 (m, 1H), 7.58 (t, J=8 Hz, 1H), 3.94 (s, 2H);

LCMS: m/z=158.8 [M+H], RT=1.22 minutes; (Program P1, Column W).

SCHEME-14: Synthesis of 1-(6,7-Difluoro-quinolin-3-yl)-ethylamine

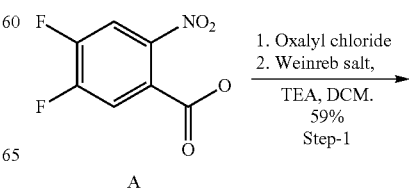

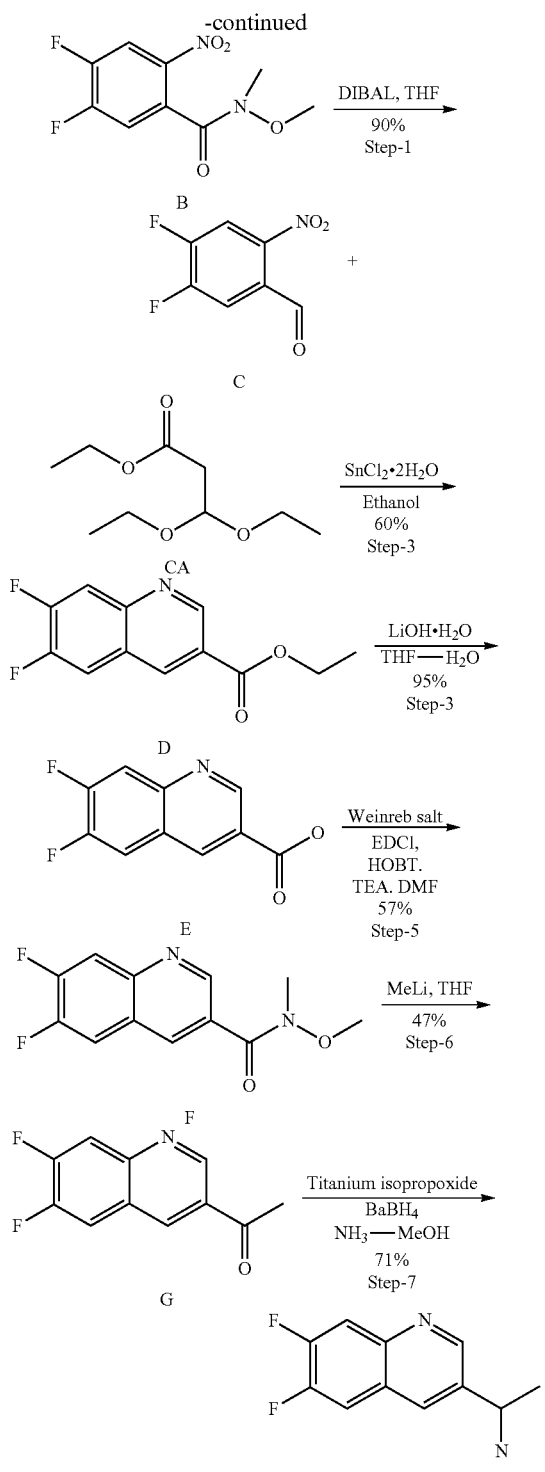

was dissolved in CH₂Cl₂ (50 mL). The solution was cooled to 0° C. and Weinreb amine salt (5.3 g, 54.1 mmol, 1.1 eq) and TEA (48 ml, 344.4 mmol, 7 eq) were added sequentially. The resulting mixture was stirred at 23° C. for 16 h. The reaction mixture was diluted in EtOAc (200 mL×3) and the organic layer was washed with saturated aq. NaHCO₃ solution, water and brine successively. Combined organic layer was dried over anhydrous Na₂SO₄, filtered and concentrated in vacuo. The crude material was purified by flash chromatography (230-400 silica gel) to obtain compound B (7.2 g, 59%) as a sticky material.

$^1$H NMR (DMSO-d₆) δ: 8.47-8.42 (dd, J=12 Hz, J=8 Hz, 1H), 7.99-7.95 (dd, J=12 Hz, J=8 Hz, 1H), 3.38 (s, 3H), 3.25 (s, 3H).

LCMS: m/z=247 [M+H], RT=3.06 minutes; (Program P1, Column y).

Step-2: Preparation of 4,5-difluoro-2-nitro-benzaldehyde

To a stirred solution of compound B (7.2 g, 29.2 mmol, 1 eq) in THF (60 ml) was added DIBAL (42 ml, 73.1 mol, 2.5 eq) at −78° C. and the resulting mixture was stirred at −20° C. for 4 h. The reaction mixture was quenched with saturated aq. NH₄Cl solution (20 ml) and diluted with EtOAc (450 ml) and water (250 ml). The organic layer was separated, washed with brine, dried over anhydrous Na₂SO₄ and concentrated in vacuo. The crude material was purified by flash chromatography (230-400 silica gel) to obtain compound C (5 g, 90%) as yellow solid.

$^1$H NMR (DMSO-d₆) δ: 10.17 (s, 1H), 8.49-8.44 (dd, J=12 Hz, J=8 Hz, 1H), 8.03-7.98 (dd, J=12 Hz, J=8 Hz, 1H);

LCMS: m/z=186 [M−H], RT=3.21 minutes; (Program P1, Column y).

Step-3: Preparation of 6,7-difluoro-quinoline-3-carboxylic acid ethyl ester

To a stirred solution of compound C (5 g, 26.7 mmol, 1 eq) in ethanol (120 ml) were added 3,3-diethoxy-propionic acid ethyl ester (13.1 ml, 66.8 mmol, 2.5 eq), SnCl₂.2H₂O (54 g, 240.5 mmol, 9 eq) at 23° C. and the resulting mixture was refluxed for 16 h. The reaction mixture was concentrated in vacuo, the residue was diluted with water (250 ml) and the pH was adjusted to ~7 with saturated aq. NaHCO₃ solution. The organic components were extracted with EtOAc (200 ml×2), combined ethyl acetate layer was washed with water, brine, dried over anhydrous Na₂SO₄, concentrated in vacuo. The crude material which was purified by flash chromatography (230-400 silica gel) with 25% EtOAc/hexane to obtain compound D (3.8 g, 60%) as light yellow solid.

$^1$H NMR (DMSO-d₆) δ: 9.29 (s, 1H), 9.00 (s, 1H), 8.34-8.29 (dd, J=12 Hz, J=8 Hz, 1H), 8.16-8.11 (dd, J=12 Hz, J=8 Hz, 1H), 4.41 (q, J=8 Hz, 1H), 1.38 (t, 3H).

LCMS: m/z=237.8 [M+H], RT=3.43 minutes; (Program P1, Column v).

Step-4: Preparation of 6,7-difluoro-quinoline-3-carboxylic acid

To a stirred solution of compound D (3.2 g, 13.5 mmol, 1 eq) in THF (10 ml) was added a solution of LiOH (1.7 gm) in water (10 ml) and the resulting mixture was stirred at 23° C. for 5 h. The reaction mixture was diluted with water (200 ml) and the pH was adjusted to 6 with saturated aq. citric acid solution. The organic components were extracted with EtOAc (300 ml) and ethyl acetate layer was washed with water and brine. Ethyl acetate layer was dried over anhydrous Na$_2$SO$_4$, filtered and concentrated in vacuo to obtain compound E (2.76 g, 95%) as white solid which was used in the next step without further purification.

$^1$H NMR (DMSO-d$_6$) δ: 13.60 (br s, 1H), 9.3 (s, 1H), 8.99 (s, 1H), 8.32-8.27 (dd, J=12 Hz, J=8 Hz, 1H), 8.15-8.10 (dd, J=12 Hz, J=8 Hz, 1H);

LCMS: m/z=210.2 [M+H], RT=1.83 minutes; (Program P1, Column y).

Step-5: Preparation of
7-fluoro-quinoline-3-carboxylic acid
methoxy-methyl-amide To a stirred solution of compound E (2.9 g, 13.8 mmol, 1 eq) in DMF (20 ml) were added EDCI.HCl (3.17 g, 16.5 mmol, 1.19 eq), HOBT (2.23 g, 16.5 mmol, 1.19 eq), and TEA (6 ml, 41.4 mmol, 3 eq) at 0° C. and the mixture was stirred for 10 minutes. Weinreb amine salt (1.48 g, 15.1 mmol, 1.09 eq) was added to it and the resulting mixture was stirred at 23° C. for 16 h. The reaction mixture was diluted with EtOAc (350 ml) and the organic layer was washed with saturated aq. NaHCO$_3$ solution (150 ml), water and brine. The organic layer was dried over anhydrous Na$_2$SO$_4$, filtered and concentrated in vacuo. The crude material was purified by Combiflash column chromatography, eluting with 25% EtOAc/hexane to obtain compound F (2 g, 57%) as white solid.

$^1$H NMR (DMSO-d$_6$) δ: 9.07 (s, 1H), 8.69 (s, 1H), 8.25-8.20 (dd, J=12 Hz, J=8 Hz, 1H), 8.13-8.08 (dd, J=12 Hz, J=8 Hz, 1H), 3.57 (s, 3H), 3.34 (s, 3H);

LCMS: m/z=253 [M+H], RT=2.82 minutes; (Program P1, Column v).

Step-6: Preparation of
1-(6,7-difluoro-quinolin-3-yl)-ethanone

To a stirred solution of compound F (0.9 g, 3.57 mmol, 1 eq) in dry THF (12 ml) was added MeLi (2.5 ml, 3.93 mmol, 1.1 eq) at −78° C. and the resulting mixture was stirred at −20° C. for 3 h. The reaction mixture was quenched with saturated aq. KHSO$_4$ solution (5 ml) at −20° C. and diluted with EtOAc (150 ml). The organic layer was washed with saturated aq. NaHCO$_3$ solution (100 ml), water and brine. The organic layer was dried over anhydrous Na$_2$SO$_4$, filtered and concentrated in vacuo. The crude material was purified by Combiflash column chromatography eluting with 19-25% EtOAc/hexane to obtain compound G (0.35 g, 47%) as an off-white solid.

$^1$H NMR (DMSO-d$_6$) δ: 9.34-9.33 (d, J=4 Hz, 1H), 9.04-9.03 (d, J=4 Hz, 1H), 8.29-8.24 (dd, J=12 Hz, J=8 Hz, 1H), 8.17-8.12 (dd, J=12 Hz, J=8 Hz, 1H), 2.72 (s, 1H);

LCMS: m/z=208 [M+H], RT=2.91 minutes; (Program P1, Column v).

Step-7: Preparation of
1-(6,7-difluoro-quinolin-3-yl)-ethylamine

To a stirred solution of compound G (0.7 g, 3.38 mmol, 1 eq) in methanolic ammonia (10 ml) was added titanium isopropoxide (2 ml, 6.8 mmol, and 2 eq) at 0° C. and the mixture was stirred at 23° C. for 16 h. NaBH$_4$ (192 mg, 5.07 mmol, 1.5 eq) was added to it at 0° C. and the resulting mixture was stirred at 23° C. for 16 h. The reaction mixture was quenched with ice-cold water (5 ml) and concentrated in vacuo. The solid residue was diluted with 10% MeOH/ CH$_2$Cl$_2$ (25 ml) and the mixture was stirred for 30 min at 23° C. The mixture was filtered and the filtrate was concentrated in vacuo. The crude material was purified by flash chromatography on neutral alumina column eluting with 7-10% MeOH/CH$_2$Cl$_2$ to obtain compound H (0.5 g, 71%) as a sticky solid.

$^1$H NMR (DMSO-d$_6$) δ: 8.95 (s, 1H), 8.28 (s, 1H), 8.05-7.96 (m, 2H), 4.21 (q, J=8 Hz, 1H), 2.06 (br s, 2H), 1.36-1.34 (d, J=8 Hz, 3H);

LCMS: m/z=208.8 [M+H], RT=2.16 minutes; (Program P1, Column v).

SCHEME-15: Synthesis of 1-Pyrazolo[1,5-a]pyridin-2-yl-ethylamine

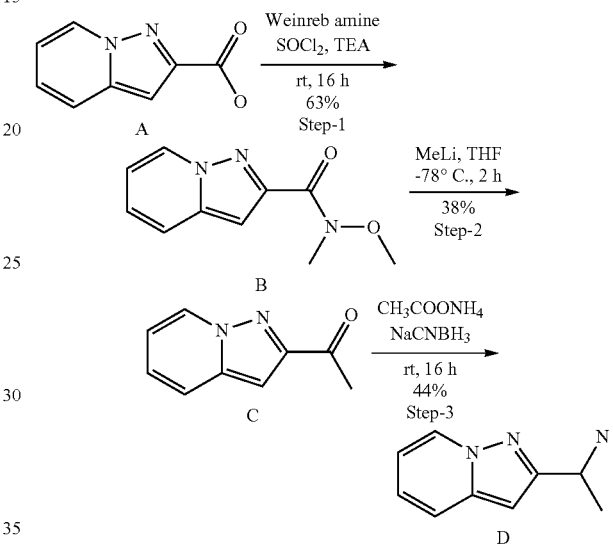

Step-1: Preparation of
pyrazolo[1,5-a]pyridine-2-carboxylic acid
methoxy-methyl-amide To a stirred solution of compound A (500 mg, 3.08 mmol, 1 eq) in CH$_2$Cl$_2$ (15 ml) was added thionyl chloride (0.665 ml, 9.25 mmol, 3 eq) and the mixture was refluxed for 3 h. The mixture was cooled to RT, concentrated in vacuo and the residue was dissolved in CH$_2$Cl$_2$ (20 ml). TEA (3 ml, 21.51 mmol, 7 eq) followed by Weinreb amine salt (450 mg, 4.62 mmol, and 1.5 eq) was added to it and the resulting mixture was stirred at 23° C. for 16 h. The reaction mixture was diluted with ethyl acetate (150 ml), the combined organic layer was washed with water and brine. The organic layer was dried over anhydrous sodium sulfate and concentrated in vacuo. The crude material was purified by column chromatography to obtain compound B (400 mg, 63%) as liquid compound.

$^1$H NMR (DMSO-d$_6$) δ 8.72-8.70 (d, J=8 Hz, 1H), 7.76-7.74 (d, J=9 Hz, 1H), 7.30-7.26 (m, 1H), 7.02-7.00 (t, J=7 Hz, 1H), 3.73 (s, 3H), 3.37 (s, 3H);

LCMS: m/z=206.0 [MPH], RT=2.27 minutes; (Program P1, Column v.

Step-2: Preparation of
1-pyrazolo[1,5-a]pyridin-2-yl-ethanone

To a solution of compound B (1 g, 4.88 mmol, 1 eq) in THF (20 ml) was added MeLi (3.5 ml, 5.36 mmol, 1.1 eq)

at −78° C. and the resulting mixture was stirred for 2 h at the same temperature. The reaction mixture was quenched with satd. aq. ammonium chloride solution (10 ml) and the organic components were extracted with ethyl acetate (200 ml). Combined organic layer was washed with water and brine, dried over sodium sulfate and concentrated in vacuo. The crude material was purified by column chromatography (eluting with 30% ethyl acetate/haxane) to obtain compound C (300 mg, 38%) as liquid.

$^1$H NMR (DMSO-$d_6$) δ 8.79-8.77 (d, J=7 Hz, 1H), 7.80-7.78 (d, J=9 Hz, 1H), 7.32-7.28 (t, J=7 Hz, 1H), 7.09-7.07 (d, J=7 Hz, 1H), 2.65-2.62 (s, 3H);

LCMS: m/z=206.0 [MPH], RT=2.27 minutes; (Program P1, Column v).

Step-3: Preparation of
1-pyrazolo[1,5-a]pyridin-2-yl-ethylamine

To a solution of compound C (270 mg, 1.69 mmol, 1 eq) in methanol (15 ml) were added ammonium acetate (1.3 g, 16.87 mmol, 10 eq), sodium cyanoborohydride (74 mg, 1.18 mmol, 0.7 eq) and molecular sieves (3 Å) and the resulting mixture was stirred at RT for 16 h. The reaction mixture was filtered and the filtrate was concentrated in vacuo. The residue was diluted with CH$_2$Cl$_2$, and extracted with 1N aq. HCl solution until acidic pH. The aqueous layer was basified with 5N aq. NaOH solution, and the organic components were extracted with 15% methanol/chloroform. The organic layer was concentrated in vacuo to obtain compound D (120 mg, 44%) as liquid.

$^1$H NMR (DMSO-$d_6$) δ 8.66-8.65 (m, 4H), 7.72-7.70 (d, J=9 Hz, 1H), 7.27-7.21 (m, 1H), 6.94-6.92 (t, J=8 Hz, 1H), 6.74 (s, 1H), 4.62-4.56 (m, 1H), 1.62-1.60 (d, J=7 Hz, 3H);

LCMS: m/z=162.2 [MPH], RT=1.27 minutes; (Program P1, Column y).

under nitrogen atmosphere. The reaction mixture was cooled to RT, diluted with water and the organic components were extracted with ethyl acetate. The organic layer was washed with aq. Na$_2$CO$_3$ solution (0.5M, 100 ml), brine, dried over anhyd. sodium sulphate and concentrated in vacuo. The crude material was purified by Combiflash eluting with 15%-20% EtOAc/hexane to obtain compound B (0.6 g, 75%).

$^1$H NMR (DMSO-$d_6$) δ 8.73-8.72 (m, 1H), 8.25-8.23 (m, 2H), 8.08-8.06 (m, 3H), 7.96-7.92 (m, 1H), 7.44-7.41 (m, 1H), 2.63 (s, 3H);

LCMS: m/z=198 [M+H], RT=3.01 min minutes; (Program P1, Column y).

Step-2: Preparation of
1-(4-Pyridin-2-yl-phenyl)-ethylamine

To a stirred solution of compound B (0.2 g, 1.01 mmol, 1 eq) in EtOH (2 ml) were added NaCNBH$_3$ (76 mg, 1.21 mmol, 1.2 eq) and NH$_4$OAc (1.16 g, 15.15 mmol, 15 eq) and the resulting mixture was heated under microwave at 130° C. for 2 min. The reaction mixture was cooled to RT and concentrated in vacuo. The residue was diluted with water and the aq. Layer was washed with ethyl acetate. The aqueous layer was basified with aq. NaOH solution (2N, 50 ml) and the organic components were extracted with ethyl acetate. The combined organic layer was dried over anhydrous sodium sulfate and concentrated in vacuo. The crude material was purified by column chromatography (neutral alumina) eluting with 1-2% methanol/CH$_2$Cl$_2$ to obtain compound C (0.09 g, 56%) as solid.

$^1$H NMR (DMSO-$d_6$) δ 8.65-8.64 (d, J=4 Hz, 1H), 8.02-8.00 (d, J=8 Hz, 2H), 7.93-7.91 (m, 1H), 7.86-7.83 (m, 1H), 7.48-7.49 (d, J=8 Hz, 2H), 7.33-7.30 (m, 1H), 4.06-4.01 (m, 1H), 1.88 (s, 2H), 1.35-1.31 (s, 3H);

LCMS: m/z=199.1 [M+H], RT=1.66 minutes; (Program P1, Column v).

SCHEME-16:

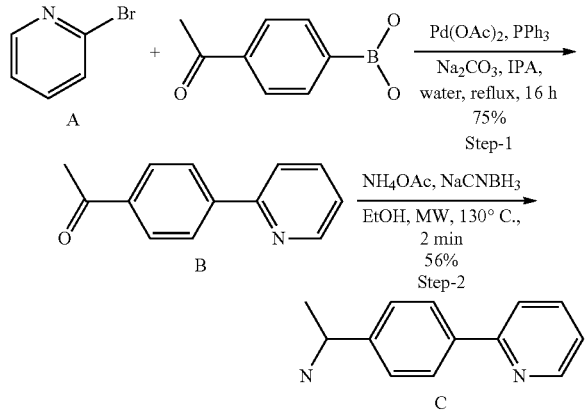

Step-1: Preparation of
1-(4-pyridin-2-yl-phenyl)-ethanone

To a stirred solution of compound A (0.58 g, 3.87 mmol, 1 mmol) in IPA (10 ml) was added 4-acetyl-phenyl-boronic acid (0.8 g, 4.87 mmol, 1.25 eq) and the mixture was stirred at 23° C. for 15 minutes. Pd(OAc)$_2$ (45 mg, 0.2 mmol, 0.05 eq), PPh$_3$ (11 mg, 0.04 mmol, 0.01 eq), 2M aqueous Na$_2$CO$_3$ (3.2 ml, 6.4 mmol, 1.65 eq) and distilled water (2 ml) were added to it and the resulting mixture was refluxed for 16 h SCHEME-17: Synthesis of 1-Quinolin-3-yl-ethylamine

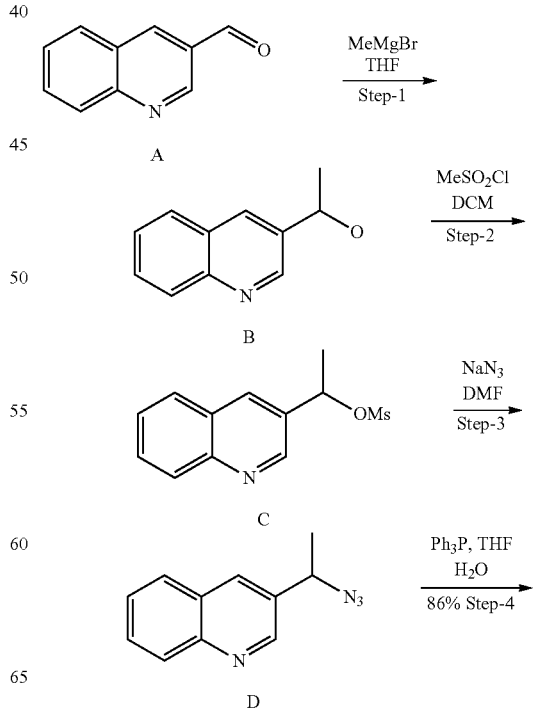

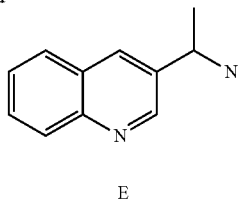

E

Step 1: Preparation of 1-quinolin-3-yl-ethanol (B)

To a stirred solution of compound A (20 g, 127.4 mmol, 1 eq) in dry THF (200 mL) was added methyl magnesium bromide (3 M in diethyl ether, 85 mL, 254.8 mmol, 2 eq) drop wise at −78° C. and the resulting mixture was stirred for 18 h at 23° C. The reaction mixture was quenched with saturated aq. $NH_4Cl$ solution and the organic components were extracted with ethyl acetate (800 ml). The organic layer was concentrated in vacuo to obtain the compound B (20.7 g) as colorless sticky material which was used in the next step without further purification.

$^1$H NMR (400 MHz, DMSO-$d_6$) δ 8.91 (m, 1H), 8.24 (s, 1H), 7.98 (t, J=8 Hz, 2H), 7.71 (t, J=8 Hz, 1H), 7.588 (t, J=8 Hz, 1H), 5.47 (d, J=4 Hz, 1H), 5.00-4.94 (m, 1H), 1.46 (d, J=7 Hz, 3H);

LCMS: m/z=174.4 [M+H], RT=1.24 minutes; (Program R1, Column Y).

Step 2: Preparation of 1-quinolin-3-yl-ethanol (C)

To a stirred solution of compound B (19.7 g, 113.9 mmol, 1 eq) in dry $CH_2Cl_2$ (200 mL) was added triethyl amine (24 mL, 170.8 mmol, 1.5 eq) and methane sulphonyl chloride (13.5 mL, 170.8 mmol, 1.5 eq) drop wise at 0° C. and the resulting mixture was stirred for 14 h at 23° C. The reaction mixture was quenched with water and the organic components were extracted with $CH_2Cl_2$ (500 ml). DCM layer was concentrated in vacuo to obtain the compound C (28 g) as brownish sticky material which was used in the next step without further purification.

$^1$H NMR (400 MHz, DMSO-$d_6$) δ 9.47 (m, 1H), 9.30 (s, 1H), 8.40-8.35 (m, 2H), 8.13 (t, J=8 Hz, 1H); 7.95 (t, J=8 Hz, 1H), 5.79-5.74 (m, 1H), 2.44 (s, 3H), 1.98 (d, J=8 Hz, 3H);

Step 3: Preparation of 3-(1-azido-ethyl)-quinoline (D)

To a stirred solution of compound C (28 g, 111.5 mmol, 1 eq) in dry DMF (150 mL) was added sodium azide (73 g, 1.11 mol, 10 eq) in small portions at 0° C. and the resulting mixture was stirred for 14 h at 23° C. The reaction mixture was quenched with ice and the organic components were extracted with ethyl acetate (500 ml). The organic layer was concentrated in vacuo to obtain the compound D (32 g) as brownish sticky material which was used in the next step without further purification.

Step 4: Preparation of 1-quinolin-3-yl-ethylamine (E)

To a stirred solution of compound D (20 g, 100 mmol, 1 eq) in a mixture of THF (300 mL) and $H_2O$ (30 ml) was added triphenylphosphine (40 g, 150 mmol, 1.5 eq) and the resulting mixture was stirred at 70° C. for 18 h. The reaction mixture was cooled to RT, and concentrated in vacuo. The crude material was purified by flash chromatography (Combiflash) using 100-200 mesh silica gel eluting with 10% methanol/dichloromethane to obtain the compound E (15 g, 86%) as brownish sticky material.

$^1$H NMR (400 MHz, DMSO-$d_6$) δ 8.94 (m, 1H), 8.24 (m, 1H), 7.98 (d, J=8 Hz, 1H), 7.93 (d, J=8 Hz, 1H), 7.71-7.67 (m, 1H), 7.59-7.55 (m, 1H), 4.25-4.20 (m, 1H), 2.16 (br s, 2H), 1.37 (d, J=8 Hz, 3H);

LCMS: m/z=173.0 [M+H], RT=1.74 minutes; (Program P1, Column Y).

SCHEME-18: Synthesis of C-Cyclopropyl-C-quinolin-3-yl-methylamine

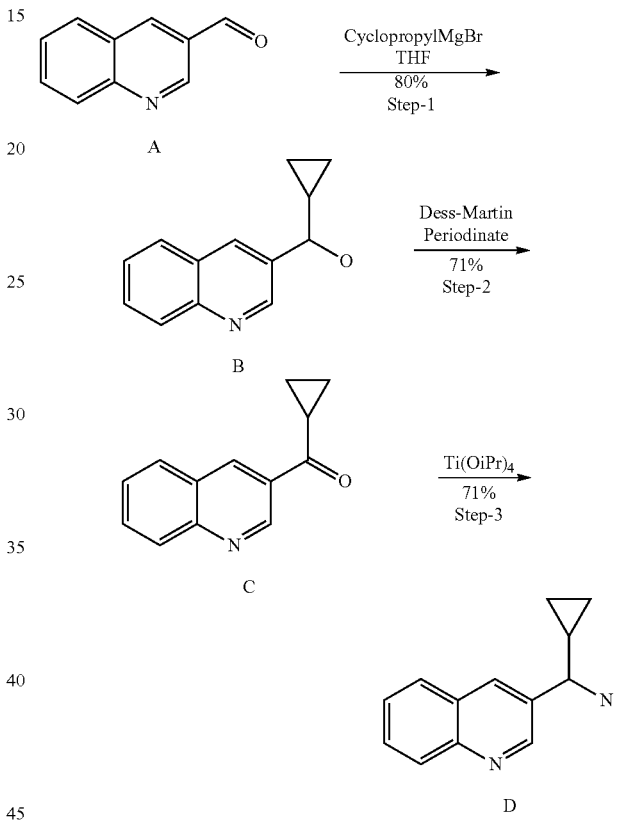

Step 1: Preparation of cyclopropyl-quinolin-3-yl-methanol (B)

To a stirred solution of compound A (8 g, 0.05 mol, 1 eq) in dry THF (200 mL) was added cyclopropyl magnesium bromide (0.5 M in THF, 203 mL, 0.10 mol, 2 eq) drop wise at −40° C. and the resulting mixture was stirred for 18 h at 23° C. The reaction mixture was quenched with saturated aq. $NH_4Cl$ solution and the organic components were extracted with ethyl acetate (500 ml). The organic layer was concentrated in vacuo to obtain the compound B (10 g, 80%) as colorless sticky material which was used in the next step without further purification.

$^1$H NMR (400 MHz, DMSO-$d_6$) δ 8.95 (s, 1H), 8.27 (s, 1H), 8.01-7.97 (m, 2H), 7.74-7.70 (m, 1H), 7.61-7.57 (m, 1H), 5.50 (s, 1H), 4.25-4.22 (m, 1H), 1.23-1.12 (m, 1H), 0.56-0.46 (m, 4H);

LCMS: m/z=199.8 [M+H], RT=2.75 minutes; (Program P1, Column Y).

Step 2: Preparation of cyclopropyl-quinolin-3-yl-methanone (C)

To a stirred solution of compound B (8 g, 0.05 mol, 1 eq) in CH$_2$Cl$_2$ (100 mL) was added Dess-Martin Periodinane at 0° C. and the resulting mixture was stirred at 23° C. for 16 h. The reaction mixture was filtered through Celite, filtrate was neutralized with aq. NaHCO$_3$ solution and the organic parts were extracted with CH$_2$Cl$_2$ (500 ml). DCM layer was concentrated in vacuo and the crude residue was purified by flash chromatography (Combiflash) using 100-200 mesh silica gel eluting with 20% ethyl acetate/hexane to obtain the compound C (7 g, 71%) as off white solid.

$^1$H NMR (400 MHz, DMSO-d$_6$) δ 9.38 (s, 1H), 9.19 (s, 1H), 8.20 (d, J=8 Hz, 1H), 8.11 (d, J=8 Hz, 1H), 1.95-1.91 (m, 1H), 7.76-7.72 (m, 1H), 3.14-3.07 (m, 1H), 1.21-1.14 (m, 4H);

LCMS: m/z=198.4 [M+H], RT=3.68 minutes; (Program R1, Column W).

Step 3: Preparation of C-cyclopropyl-C-quinolin-3-yl-methylamine (D)

To a stirred solution of compound C (4.5 g, 20 mmol, 1 eq) in methanolic ammonia (7 N, 100 mL) was added titanium isopropoxide (13.5 mL, 50 mmol, 2.5 eq) drop wise at 0° C. and the mixture was stirred for 24 h at 23° C. Sodium borohydride (1.3 g, 30 mmol, 1.5 eq) was added to it in small portions at 0° C. and the resulting mixture was stirred for 18 h at 23° C. The reaction mixture was quenched with ice and concentrated in vacuo. The solid was diluted with 10% MeOH/CH$_2$Cl$_2$, the mixture was stirred for 20 min., filtered, the filtrate was concentrated in vacuo. The crude residue was purified by flash chromatography using neutral alumina eluting with 6% methanol/dichloromethane to obtain the compound D (2.8 g, 71%) as brownish sticky material.

$^1$H NMR (400 MHz, DMSO-d$_6$) δ 8.98 (s, 1H), 8.28 (br s, 1H), 8.00-7.94 (m, 2H), 7.72-7.68 (m, 1H), 7.60-7.56 (m, 1H), 3.41 (d, J=8 Hz, 1H), 2.20 (br s, 2H), 1.23-1.04 (m, 1H), 0.55-0.49 (m, 4H);

LCMS: m/z=198.8 [M+H], RT=1.88 minutes; (Program P1, Column W).

Synthesis of Other Amine Intermediates:

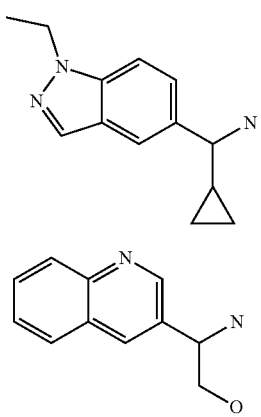

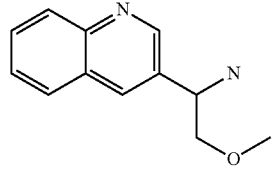

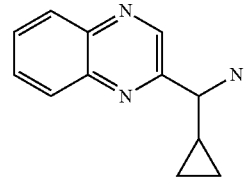

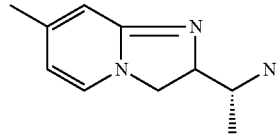

The amines (I-V) were synthesized with a combination of above-mentioned protocols, using commercially available appropriate precursors, as would be apparent to one of ordinary skill in the art.

Synthesis Schemes for Compounds of Formula (I):

The compounds of formula (I) can be synthesized according to the schemes shown in the Examples below. It will be apparent and understood by one of ordinary skill in the art that the chemical structures represented below that contain heteroatoms may, in certain circumstances, have one or more bound hydrogens that are not shown.

Example 1

The following Scheme 19 is a representative synthesis of—1-{4-[2-Isopropyl-7-((R)-1-quinolin-3-yl-ethylamino)-2H-pyrazolo[4,3-d]pyrimidin-5-yl]-piperazin-1-yl}-ethanone:

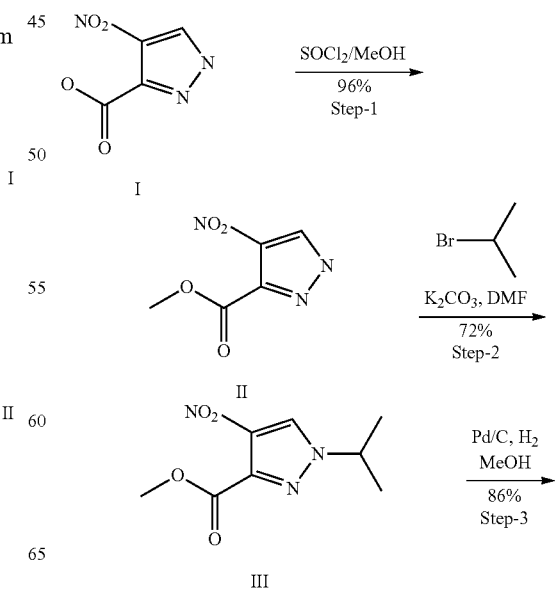

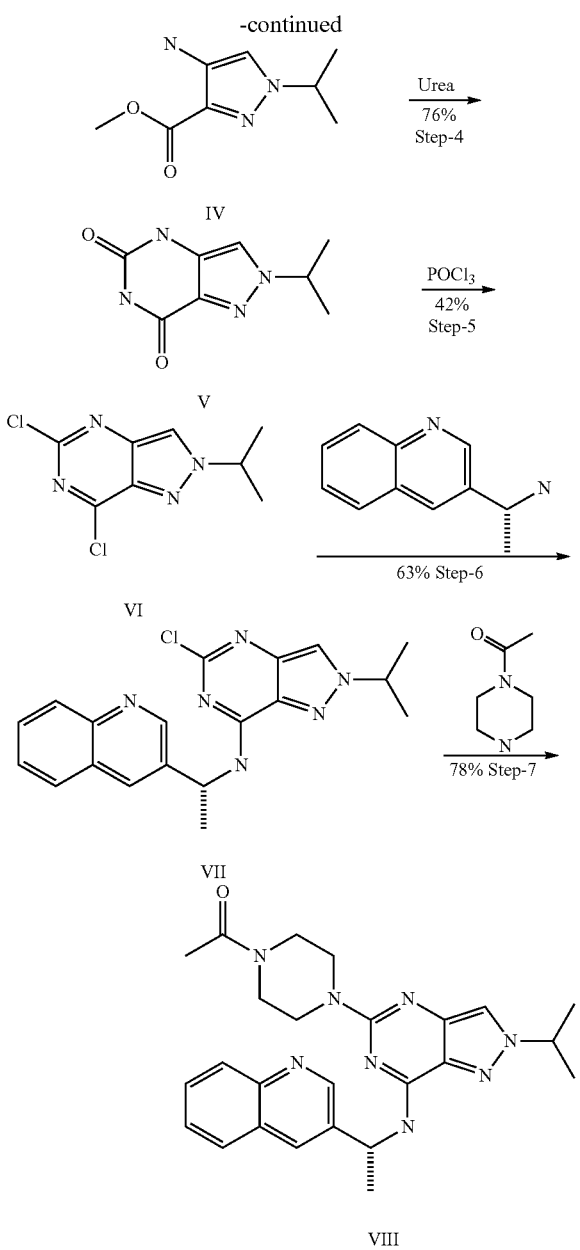

4-Nitro-1H-pyrazole-3-carboxylic acid methyl ester (II)

To a stirred solution of compound I (10 g, 64 mmol, 1 eq) in methanol (100 ml) was added SOCl$_2$ (5.2 ml, 67 mmol, 1.05 eq) drop wise at ice-cold condition and the resulting mixture was stirred at 23° C. for 16 h. The reaction mixture was concentrated in vacuo, the residue was diluted with water (25 ml) and the organic components were extracted with ethyl acetate (200 ml). The ethyl acetate layer was removed in vacuo to obtain the desired compound II (10.5 g, 96%) as off white solid which was used in the next step without further purification.

$^1$H NMR (400 MHz, DMSO-d$_6$) δ 14.41 (br s, 1H), 8.97 (s, 1H), 3.88 (s, 3H);

LCMS: m/z=172.0 [M+H], RT=2.12 minutes; (Program Q1, Column X).

1-Isopropyl-4-nitro-1H-pyrazole-3-carboxylic acid methyl ester (III)

To a solution of compound II (2 g, 11 mmol, 1 eq) in DMF (10 mL) were added K$_2$CO$_3$ (2 g, 14 mmol, 1.3 eq) and 2-bromo propane (2.06 mL, 22 mmol, 2 eq) drop wise at 0° C. and the resulting mixture was stirred for 18 h at 23° C. The reaction mixture was diluted with water (50 ml), the organic components were extracted with ethyl acetate (100 ml), ethyl acetate layer was concentrated in vacuo. The crude residue was purified by flash chromatography (Combiflash) using 100-200 mesh silica gel and eluting with 24% ethylacetate/hexane to obtain compound III (1.7 g, 72%) as pale yellow sticky material $^1$H NMR (400 MHz, DMSO-d$_6$) δ 8.16 (s, 1H), 4.58-4.55 (m, 1H), 3.98 (s, 3H), 1.57-1.52 (m, 6H);

LCMS: m/z=214.0 [M+H], RT=3.03 minutes; (Program Q1, Column X).

4-Amino-1-isopropyl-1H-pyrazole-3-carboxylic acid methyl ester (IV)

To a solution of compound III (200 mg, 0.94 mol, 1 eq) in methanol (10 mL) was added Pd/C (10% Pd, 10 mole %) and the resulting mixture was stirred at 23° C. under hydrogen atmosphere for 14 h. The reaction mixture was filtered through Celite and the filtrate was concentrated in vacuo to get compound IV (150 mg, 86%) as brown solid which was used in the next step without further purification.

$^1$H NMR (400 MHz, DMSO-d$_6$) δ 7.18 (s, 1H), 4.65 (br s, 2H), 4.42-4.36 (m, 1H), 3.74 (s, 3H), 1.39-1.35 (m, 6H);

LCMS: m/z=184.2 [M+H], RT=1.20 minutes; (Program Q1, Column Y).

2-Isopropyl-2,4-dihydro-pyrazolo[4,3-d]pyrimidine-5,7-dione (V)

To compound IV (700 mg, 3.78 mol, 1 eq) was added urea (1.14 g, 18.9 mmol, 5 eq) and the mixture was heated in a sealed tube at 160° C. for 16 h. The reaction mixture cooled to RT and diluted with water (50 mL), filtered to obtain compound V (600 mg, 76%) as an off-white solid which was used in the next step without further purification.

$^1$H NMR (400 MHz, DMSO-d$_6$) δ 10.84 (s, 1H), 10.74 (s, 1H), 7.68 (s, 1H), 4.65-4.58 (m, 1H), 1.43 (d, J=7 Hz, 6H).

5,7-Dichloro-2-isopropyl-2H-pyrazolo[4,3-d]pyrimidine (VI)

To compound V (500 mg, 2.58 mmol, 1 eq) were added POCl$_3$ (20 mL) and diethyl aniline (1.1 mL, 6.70 mmol, 2.6 eq) drop wise under ice-cold condition and the resulting mixture was stirred for 10 h at 80° C. The reaction mixture was cooled to RT, concentrated in vacuo and the residue was quenched with ice. pH of the solution was adjusted to ~7 by aq. ammonia (3-4 mL) and the organic components were extracted with ethyl acetate (100 ml) and ethyl acetate layer was concentrated in vacuo. The crude material was purified by flash chromatography (Combiflash) using 100-200 mesh silica gel eluting with 3% ethyl acetate/hexane to obtain compound VI (250 mg, 42%) as yellow solid.

$^1$H NMR (400 MHz, DMSO-d$_6$) δ 8.17 (s, 1H), 4.94-4.87 (m, 1H), 1.69 (d, J=7 Hz, 6H);

LCMS: m/z=231.2 [M+H], RT=3.19 minutes; (Program R1, Column Y).

(5-Chloro-2-isopropyl-2H-pyrazolo[4,3-d]pyrimidin-7-yl)-((R)-1-quinolin-3-ylethyl) amine (VII)

To a solution of compound VI (60 mg, 0.26 mmol, 1 eq) in tert-butyl alcohol (3 mL) were added (R)-1-quinolin-3- yl-ethylamine (54 mg, 0.31 mmol, 1.2 eq) and DIPEA (0.10 mL, 0.52 mmol, 2 eq) and the resulting mixture was stirred at 23° C. for 24 h. The reaction mixture was concentrated in vacuo and the residue was diluted with water (10 mL). The organic components were extracted with $CH_2Cl_2$ (30 mL), DCM layer was dried over anhydrous sodium sulfate and concentrated in vacuo. The crude material was purified by flash chromatography (Combiflash) using 100-200 mesh silica gel eluting with 65% ethyl acetate/hexane to obtain compound VII (60 mg, 63%) as off white foamy solid.

$^1$H NMR (400 MHz, DMSO-$d_6$) δ 9.27 (d, J=8 Hz, 1H), 9.04 (d, J=2 Hz, 1H), 8.40 (s, 1H), 8.33-8.32 (m, 1H), 8.00-7.96 (m, 2H), 7.75-7.70 (m, 1H), 7.61-7.58 (m, 1H), 5.69-5.65 (m, 1H), 4.82-4.77 (m, 1H), 1.72-1.67 (m, 3H), 1.56-1.54 (m, 6H);

LCMS: m/z=367.4 [M+H], RT=2.91 minutes; (Program R1, Column Y).

1-{4-[2-Isopropyl-7-((R)-1-quinolin-3-yl-ethyl-amino)-2H-pyrazolo[4,3-d]pyrimidin-5-yl]-piperazin-1-yl}-ethanone (VIII)

To a solution of VII (50 mg, 0.14 mmol, 1 eq) in n-butyl alcohol (3 mL) were added N-acetyl piperazine (35 mg, 0.27 mmol, 2 eq) and DIPEA (0.12 mL, 0.68 mmol, 5 eq) and the resulting mixture was refluxed for 48 h. The reaction mixture was cooled to RT, concentrated in vacuo and the residue was diluted with water (30 mL). The organic components were extracted with $CH_2Cl_2$ (40 mL), DCM layer was dried over anhyd. sodium sulfate and concentrated in vacuo. The crude material was finally purified by flash chromatography (Combiflash) using 100-200 mesh silica gel eluting with 4% MeOH/$CH_2Cl_2$ to obtain compound VIII (50 mg, 78%) as off white solid.

$^1$H NMR (400 MHz, DMSO-$d_6$) δ 9.05 (d, J=2 Hz, 1H), 8.49 (d, J=7 Hz, 1H), 8.33-8.33 (m, 1H), 7.96 (t, J=8 Hz, 2H), 7.91 (s, 1H), 7.71-7.67 (m, 1H), 7.59-7.56 (m, 1H), 5.53 (t, J=7 Hz, 1H), 4.69-4.66 (m, 1H), 3.59-3.25 (m, 8H), 1.97 (s, 3H), 1.69 (d, J=8 Hz, 3H), 1.68-1.52 (m, 6H);

LCMS: m/z=459.4 [M+H], RT=2.29 minutes; (Program R1, Column Y).

Examples 2-8

The 7 compounds of formula (I) identified in Table 1 were synthesized using Scheme 19.

TABLE 1

| Example No. | Molecular Structure | LCMS |
|---|---|---|
| 2 | 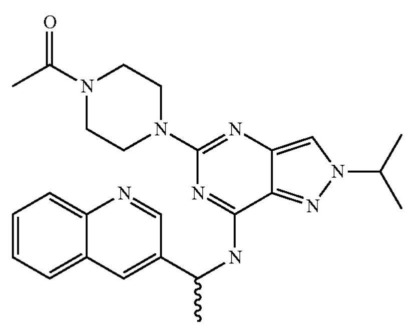 [SMILES: CC(=O)N1CCN(c2nc(NC(C)c3cnc4ccccc4c3)c3nn(C(C)C)cc3n2)CC1] | LCMS: m/z = 459.4 [M + H], RT = 2.09 minutes; (Program R1, Column X). |
| 3 | 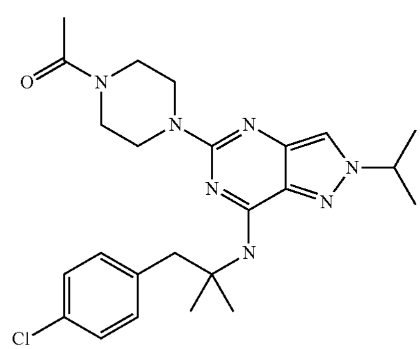 [SMILES: CC(=O)N1CCN(c2nc(NC(C)(C)Cc3ccc(Cl)cc3)c3nn(C(C)C)cc3n2)CC1] | LCMS: m/z = 470.4 [M + H], RT = 2.90 minutes; (Program R1, Column Y). |
| 4 | 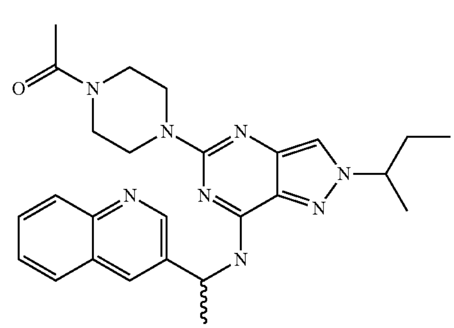 [SMILES: CCC(C)n1cc2nc(N3CCN(C(C)=O)CC3)nc(NC(C)c3cnc4ccccc4c3)c2n1] | LCMS: m/z = 473.4 [M + H], RT = 2.50 minutes; (Program R1, Column Y). |

TABLE 1-continued

| Example No. | Molecular Structure | LCMS |
|---|---|---|
| 5 | 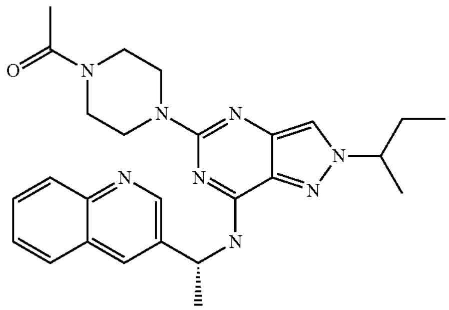 | LCMS: m/z = 473.0 [M + H], RT = 2.50 minutes; (Program R1, Column Y). |
| 6 | 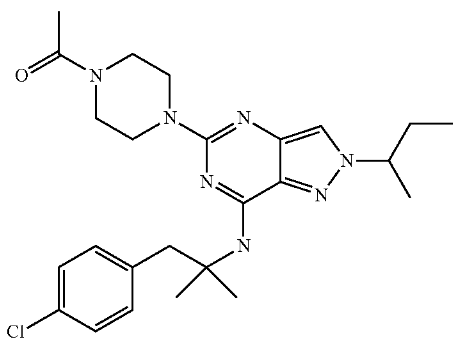 [SMILES: CCC(C)n1cc2nc(N3CCN(C(C)=O)CC3)nc(NC(C)(C)Cc3ccc(Cl)cc3)c2n1] | LCMS: m/z = 483.8 [M + H], RT = 2.99 minutes; (Program R1, Column Y). |
| 7 | 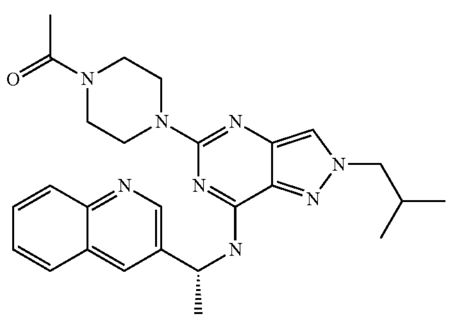 [SMILES: CC(=O)N1CCN(c2nc(N[C@H](C)c3cnc4ccccc4c3)c3nn(CC(C)C)cc3n2)CC1] | LCMS: m/z = 472.8 [M + H], RT = 2.48 minutes; (Program R1, Column Y). |
| 8 | 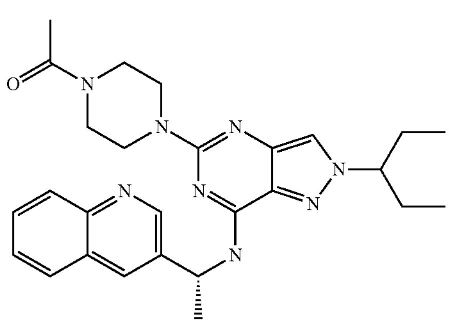 [SMILES: CCC(CC)n1cc2nc(N3CCN(C(C)=O)CC3)nc(N[C@H](C)c3cnc4ccccc4c3)c2n1] | LCMS: m/z = 487.4 [M + H], RT = 2.67 minutes; (Program R1, Column Y). |

Example 9—Scheme 20: Synthesis of 1-{4-[2-Phenyl-7-((R)-1-quinolin-3-yl-ethylamino)-2H-pyrazolo[4,3-d]pyrimidin-5-yl]-piperazin-1-yl}ethanone

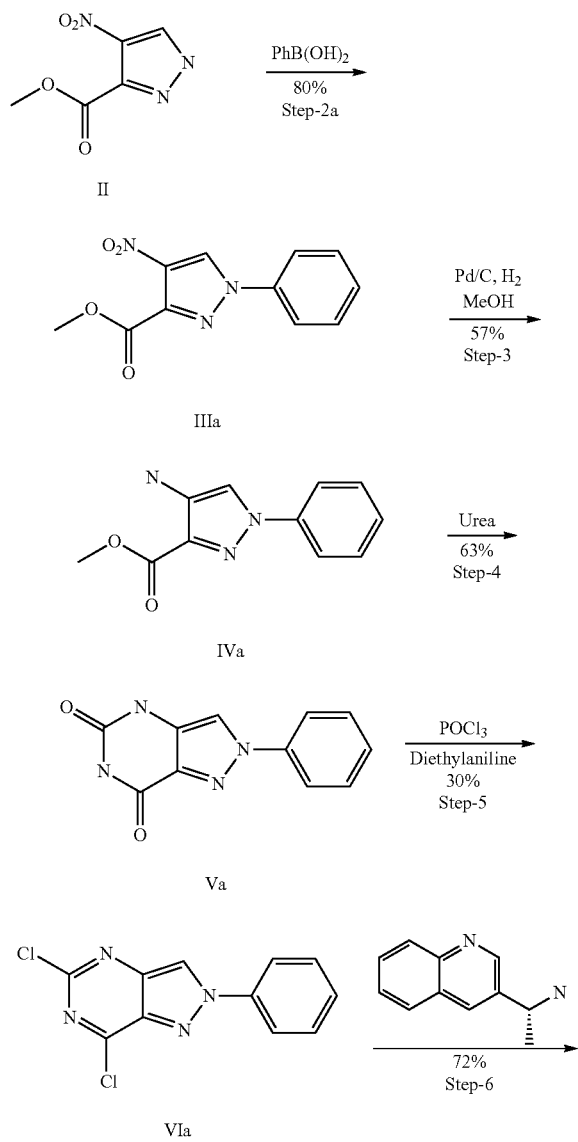

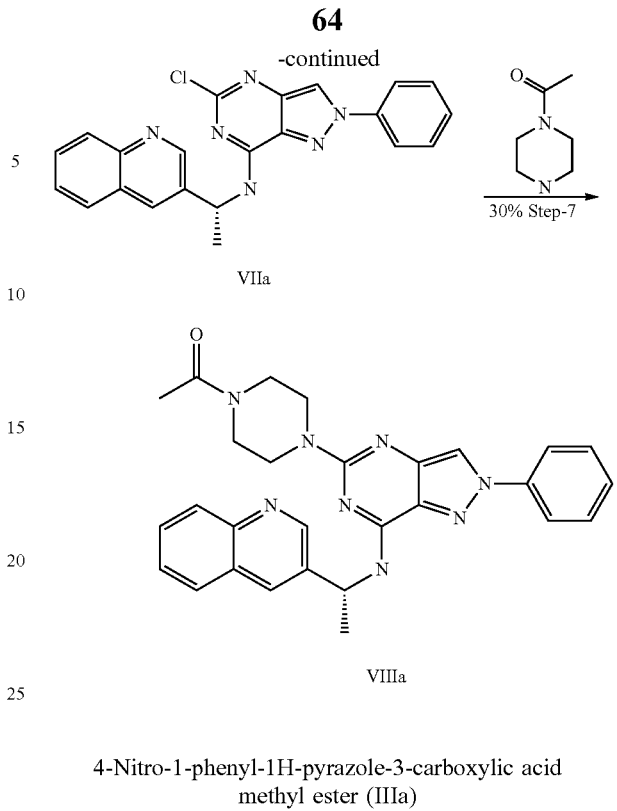

4-Nitro-1-phenyl-1H-pyrazole-3-carboxylic acid methyl ester (IIIa)

To a solution of compound II (200 mg, 1.17 mmol, 1 eq) in dry $CH_2Cl_2$ (15 mL) were added phenyl boronic acid (285 mg, 2.34 mmol, 2 eq), pyridine (0.2 mL, 2.34 mmol, 2 eq) and $Cu(OAc)_2.H_2O$ (350 mg, 1.75 mmol, 1.5 eq) and the resulting mixture was refluxed for 14 h. The reaction mixture was filtered through Celite, solids were washed with $CH_2Cl_2$ (100 ml) and the combined filtrate was concentrated in vacuo. The crude residue was purified by flash chromatography (Combiflash) using 100-200 mesh silica gel eluting with 24% ethyl acetate/hexane to obtain compound Ma (230 g, 80%) as colorless sticky material.

$^1$H NMR (400 MHz, DMSO-$d_6$) δ 9.73 (s, 1H), 7.94 (d, J=8 Hz, 2H), 7.62-7.58 (m, 2H), 7.52-7.50 (m, 1H), 3.95 (s, 3H);

LCMS: m/z=248.0 [M+H], RT=3.32 minutes; (Program R1, Column Y).

Steps 3 to 7 were carried out according to the process described in Scheme 19 to obtain the compound of Example 9 (shown in Table 2 below) as an off white solid.

TABLE 2

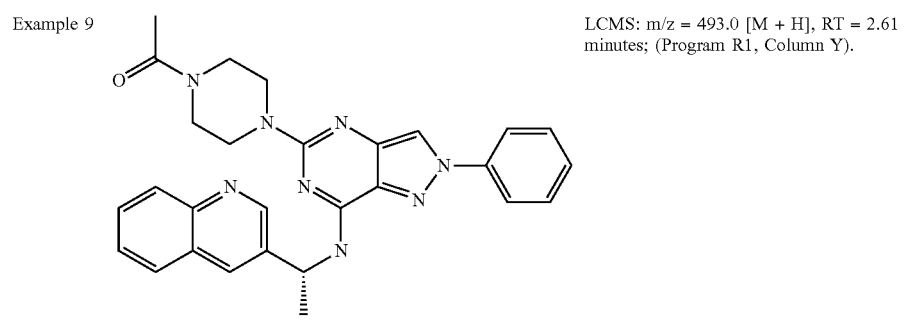

Example 9 — LCMS: m/z = 493.0 [M + H], RT = 2.61 minutes; (Program R1, Column Y).

Example 10—Scheme 21 Below is a Representative Synthesis of—4-{1-sec-Butyl-7-[((R)-cyclopropyl-quinolin-3-yl-methyl)-amino]-1H-pyrazolo[4,3-d]pyrimidin-5-yl}-piperazine-1-carboxylic acid amide)

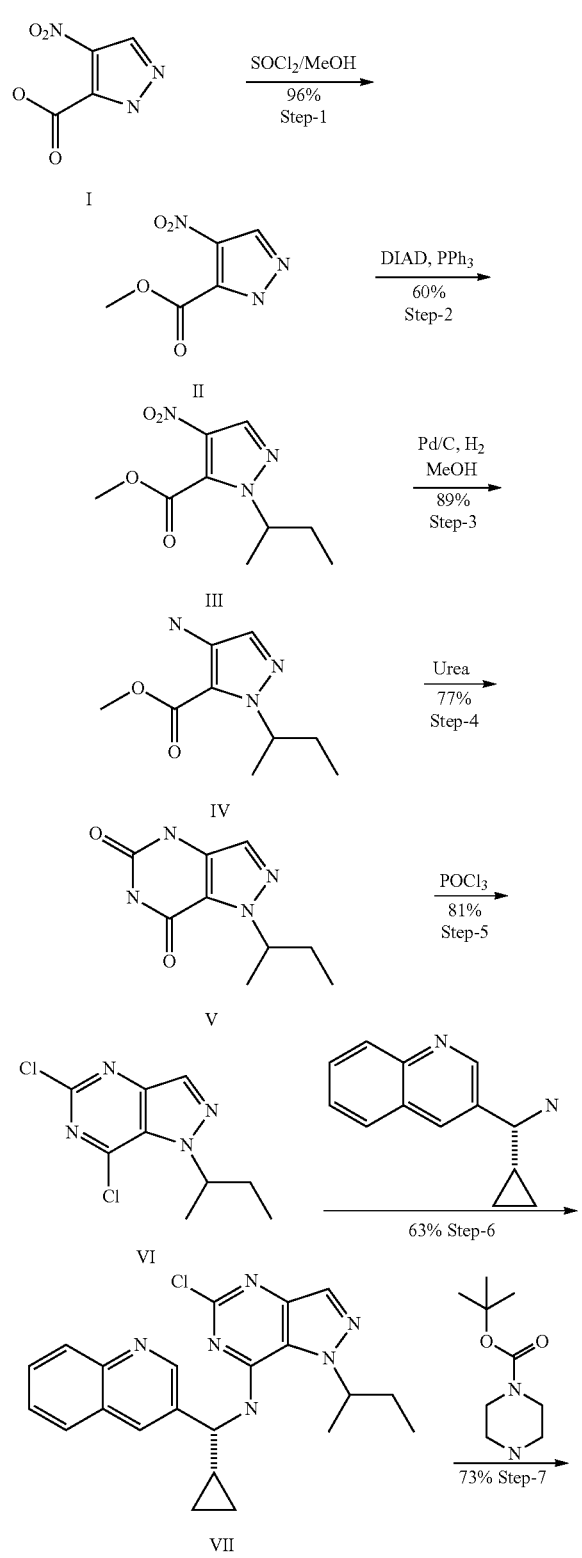

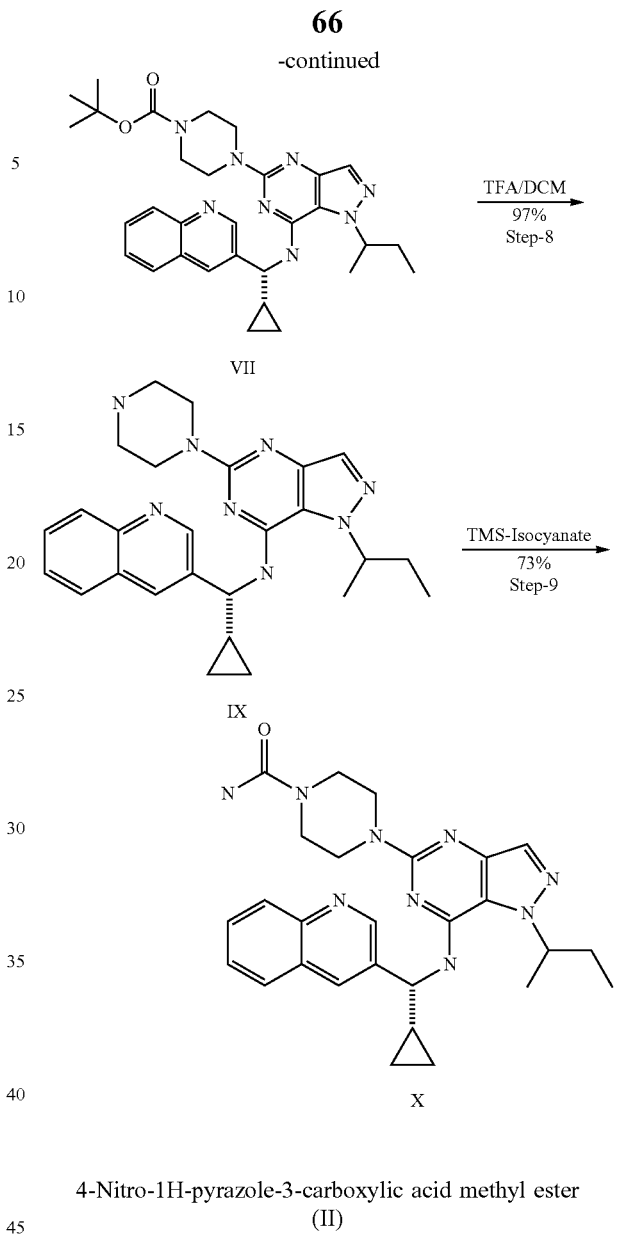

4-Nitro-1H-pyrazole-3-carboxylic acid methyl ester (II)

To a stirred solution of compound I (10 g, 64 mmol, 1 eq) in methanol (100 ml) was added $SOCl_2$ (5.2 ml, 67 mmol, 1.05 eq) drop wise at ice-cold condition and the resulting mixture was stirred for 16 h at 23° C. The reaction mixture was concentrated in vacuo and the residue was diluted with water (25 ml). The organic components were extracted with ethyl acetate (200 ml), ethyl acetate layer was concentrated in vacuo to obtain the desired compound II (10.5 g, 96%) as off white solid material which was used in the next step without further purification.

$^1$H NMR (400 MHz, DMSO-$d_6$) δ 14.41 (br s, 1H), 8.97 (s, 1H), 3.88 (s, 3H);

LCMS: m/z=172.0 [M+H], RT=2.12 minutes; (Program Q1, Column X).

2-sec-Butyl-4-nitro-2H-pyrazole-3-carboxylic acid methyl ester (III)

To a solution of compound II (5 g, 0.03 mol, 1 eq) in dry THF (100 mL) were added butan-2-ol (4.3 g, 58 mmol, 2 eq) and triphenyl phosphine (15.3 g, 58 mmol, 2 eq) under ice-cold condition. DIAD (12 mL, 58 mmol, 2 eq) was added to it drop wise at 0° C. and the resulting mixture was stirred for 3 h at the same temperature. The reaction mixture was concentrated in vacuo, the residue was diluted with water (100 ml) and the organic components were extracted with ethyl acetate (250 ml). Ethyl acetate layer was concentrated in vacuo and the crude residue was purified by flash chromatography (Combiflash) using 100-200 mesh silica gel eluting with 5% ethyl acetate/hexane to obtain compound III (4 g, 60%) as pale yellow sticky material.

$^1$H NMR (400 MHz, DMSO-d$_6$) δ 8.43 (s, 1H), 4.44-4.39 (m, 1H), 3.32 (s, 3H), 1.90-1.74 (m, 2H), 4.44-4.43 (m, 3H), 0.52-0.32 (m, 3H);

LCMS: m/z=228.2 [M+H], RT=5.10 minutes; (Program R2, Column W).

4-Amino-2-sec-butyl-2H-pyrazole-3-carboxylic acid methyl ester (IV)

To a solution of compound III (4.5 g, 20 mmol, 1 eq) in methanol (150 mL) was added Pd/C (10% Pd, 10 mole %) and the resulting mixture was stirred at 23° C. under hydrogen atmosphere for 14 h. The reaction mixture was filtered through Celite and the filtrate was concentrated in vacuo to get compound IV (2 g, 89%) light brown sticky material which was used in the next step without further purification.

$^1$H NMR (400 MHz, DMSO-d$_6$) δ 7.08 (s, 1H), 5.07-5.02 (m, 1H), 4.99-4.92 (m, 2H), 3.79 (s, 3H), 1.83-1.74 (m, 1H), 1.68-1.60 (m, 1H), 1.29 (d, J=7 Hz, 3H), 0.70-0.66 (m, 3H)

LCMS: m/z=198.1 [M+H], RT=2.96 minutes; (Program R1, Column W).

1-sec-Butyl-1,4-dihydro-pyrazolo[4,3-d]pyrimidine-5,7-dione (V)

To compound IV (1 g, 5 mmol, 1 eq) urea (1.5 g, 25 mmol, 5 eq) was added and the mixture was heated in a selared tube at 160° C. for 16 h. The reaction mixture was cooled to RT, diluted with water (60 mL) and filtered to obtain compound V (800 mg, 77%) as off-white solid which was used in the next step without further purification.

$^1$H NMR (400 MHz, DMSO-d$_6$) δ 11.07-11.00 (m, 2H), 7.39 (s, 1H), 5.04-4.99 (m, 1H), 1.89-1.80 (m, 1H), 1.78-1.73 (m, 1H), 1.40 (d, J=7 Hz, 3H), 0.68 (t, J=7 Hz, 3H);

LCMS: m/z=207.1 [M+H], RT=2.36 minutes; (Program R1, Column W).

1-sec-Butyl-5,7-dichloro-1H-pyrazolo[4,3-d]pyrimidine (VI)

To compound V (1 g, 4.81 mmol, 1 eq) were added POCl$_3$ (70 mL) and diethyl aniline (2 mL, 12.5 mmol, 2.6 eq) drop wise under ice-cold condition and the resulting mixture was stirred for 10 h at 80° C. The reaction mixture was cooled to RT, concentrated in vacuo, and the residue was quenched with ice. pH of the solution was adjusted to ~7 by aq. ammonia (3-4 mL) and the organic components were extracted with ethyl acetate (200 ml). Ethyl acetate layer was concentrated in vacuo, and the crude material was purified by flash chromatography (Combiflash) using 100-200 mesh silica gel eluting with 2.5% ethyl acetate/hexane to obtain compound VI (950 mg, 81%) as yellow solid.

$^1$H NMR (CDCl$_3$) δ 8.23 (s, 1H), 5.29-5.24 (m, 1H), 2.15-2.08 (m, 1H), 1.94-1.87 (m, 1H), 1.59 (d, J=7 Hz, 3H), 8.04 (t, J=7 Hz, 3H);

LCMS: m/z=245.1[M+H], RT=4.03 minutes; (Program R1, Column w).

(1-sec-Butyl-5-chloro-1H-pyrazolo[4,3-d]pyrimidin-7-yl)-((R)-cyclopropyl-quinolin-3-yl-methyl)-amine (VII)

To a solution of compound VI (190 mg, 0.78 mmol, 1 eq) in tert-butyl alcohol (5 mL) were added C—((R)—C-cyclopropyl-C-quinolin-3-yl)-methylamine (154 mg, 0.78 mmol, 1 eq) and DIPEA (0.40 mL, 2.33 mmol, 3 eq) and the resulting mixture was stirred at 23° C. for 24 h. The reaction mixture was concentrated in vacuo, the residue was diluted with water (30 mL) and the organic components were extracted with CH$_2$Cl$_2$ (100 mL). DCM layer was dried over anhyd. sodium sulfate and concentrated in vacuo. The crude material which was purified by flash chromatography (Combiflash) using 100-200 mesh silica gel eluting with 61% ethyl acetate/hexane to obtain compound VII (200 mg, 63%) off white foamy solid.

$^1$H NMR (400 MHz, DMSO-d$_6$) δ 9.12-9.10 (m, 1H), 8.46-8.45 (m, 1H), 8.22-8.19 (m, 1H), 8.07-8.06 (m, 1H), 8.00-7.96 (m, 2H), 7.76-7.72 (m, 1H), 7.63-7.59 (m, 1H), 5.19-5.16 (m, 1H), 4.87-4.77 (m, 1H), 1.90-1.77 (m, 3H), 1.59-1.52 (m, 3H), 0.75-0.63 (m, 7H);

LCMS: m/z=407.2 [M+H], RT=4.12 minutes; (Program R1, Column W).

4-{1-sec-Butyl-7-[((R)-cyclopropyl-quinolin-3-yl-methyl)-amino]-1H-pyrazolo[4,3-d]pyrimidin-5-yl}-piperazine-1-carboxylic acid tert-butyl ester (VIII)

To a solution of VII (200 mg, 0.49 mmol, 1 eq) in n-butyl alcohol (5 mL) were added N—BOC piperazine (183 mg, 0.99 mmol, 2 eq) and DIPEA (0.3 mL, 1.48 mmol, 3 eq) and the mixture was refluxed for 48 h. The reaction mixture was cooled to RT, concentrated in vacuo, the residue was diluted with water (30 mL). The organic components were extracted with CH$_2$Cl$_2$ (100 mL), DCM layer was dried over anhyd. sodium sulfate and concentrated in vacuo. The crude material was purified by flash chromatography (Combiflash) using 100-200 mesh silica gel eluting with 3.5% MeOH/CH$_2$Cl$_2$ to obtain compound VIII (200 mg, 73%) as light brown solid.

$^1$H NMR (400 MHz, DMSO-d$_6$) δ 9.11-9.09 (m, 1H), 8.43-8.42 (m, 1H), 8.00-7.93 (m, 2H), 7.73-7.69 (m, 2H), 7.60-7.55 (m, 2H), 5.16-4.97 (m, 1H), 4.75-4.55 (m, 1H), 3.51-3.32 (m, 4H), 3.20-3.01 (m, 4H), 1.90-1.81 (m, 3H), 1.58-1.50 (m, 3H), 1.39-1.38 (m, 9H), 1.25-1.23 (m, 3H), 0.77-0.61 (m, 4H);

LCMS: m/z=557.5 [M+H], RT=3.44 minutes; (Program R1, Column Y).

(1-sec-Butyl-5-piperazin-1-yl-1H-pyrazolo[4,3-d]pyrimidin-7-yl)-((R)-cyclopropyl-quinolin-3-yl-methyl)-amine (IX)

To a solution of compound VIII (200 mg, 0.36 mmol, 1 eq) in CH$_2$Cl$_2$ (5 mL) was added TFA (1 mL, 3.60 mmol, 10 eq) in ice-cold condition and the resulting mixture was stirred at 23° C. for 3 h. The reaction mixture was concentrated in vacuo, the residue was diluted with toluene (3 mL) and further concentrated. The residue was then diluted with aq. NaHCO$_3$ (3-4 mL) and the organic components were extracted with 5% MeOH/CH$_2$Cl$_2$ (100 ml). Organic layer was concentrated in vacuo to obtain compound IX (160 mg, 97%) off white solid which was used in the next step without further purification.

$^1$H NMR (400 MHz, DMSO-d$_6$) δ 9.09-9.07 (m, 1H), 8.40-8.39 (m, 1H), 8.00-7.97 (m, 1H), 7.95-7.91 (m, 1H), 7.73-7.69 (m, 1H), 7.67-7.66 (m, 1H), 7.60-7.57 (m, 1H), 7.52-7.50 (m, 1H), 5.07-4.98 (m, 1H), 4.75-4.55 (m, 1H), 3.38-3.29 (m, 8H), 1.96-1.59 (m, 3H), 1.57-1.49 (m, 3H), 1.33-1.23 (m, 3H), 0.78-0.57 (m, 5H);

LCMS: m/z=457.4 [M+H], RT=2.77 minutes; (Program R1, Column Y).

4-{1-sec-Butyl-7-[((R)-cyclopropyl-quinolin-3-yl-methyl)-amino]-1H-pyrazolo[4,3-d]pyrimidin-5-yl}-piperazine-1-carboxylic acid amide (X)

To a solution of compound IX (50 mg, 0.11 mmol, 1 eq) in THF (3 mL) was added TMS-isocyanate (0.03 mL, 0.22 mmol, 2 eq) at 23° C. and the resulting mixture was stirred for 14 h. The reaction mixture was diluted with aq. NaHCO$_3$ (10 mL) and the organic components were extracted with ethyl acetate (70 mL). Organic layer was dried over anhydrous sodium sulfate and concentrated in vacuo. The crude material was purified by flash chromatography (Combiflash) using 100-200 mesh silica gel eluting with 12% MeOH/CH$_2$Cl$_2$ to obtain compound X (40 mg, 73%) as off white solid.

$^1$H NMR (400 MHz, DMSO-d$_6$) δ 9.11-9.08 (m, 1H), 8.42-8.40 (m, 1H), 8.00-7.93 (m, 2H), 7.73-7.69 (m, 2H), 7.61-7.54 (m, 2H), 5.95-5.94 (m, 2H), 5.09-5.07 (m, 1H), 4.79-4.62 (m, 1H), 4.44-3.14 (m, 8H), 1.85-1.74 (m, 3H), 1.57-1.50 (m, 3H), 1.25-1.24 (m, 3H), 0.84-0.70 (m, 4H);

LCMS: m/z=500.4 [M+H], RT=2.94 minutes; (Program R1, Column Y).

Examples 11-88

The 77 compounds shown in Table 3 below were synthesized using Scheme-21.

TABLE 3

| Example No. | Molecular Structure | LCMS |
|---|---|---|
| 11 | 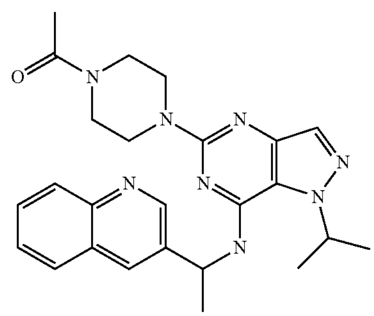 [SMILES: CC(=O)N1CCN(c2nc(NC(C)c3cnc4ccccc4c3)c3c(cnn3C(C)C)n2)CC1] | LCMS: m/z = 459.4 [M + H], RT = 2.32 minutes; (Program R1, Column Y). |
| 12 | 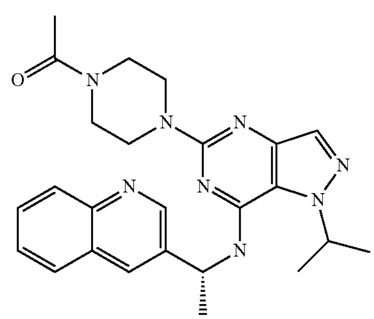 [SMILES: CC(=O)N1CCN(c2nc(N[C@H](C)c3cnc4ccccc4c3)c3c(cnn3C(C)C)n2)CC1] | LCMS: m/z = 459.4 [M + H], RT = 2.75 minutes; (Program P1, Column Y). |
| 13 | 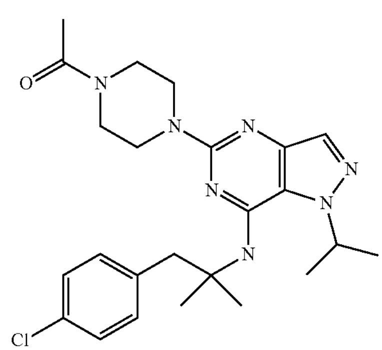 [SMILES: CC(=O)N1CCN(c2nc(NC(C)(C)Cc3ccc(Cl)cc3)c3c(cnn3C(C)C)n2)CC1] | LCMS: m/z = 470.2 [M + H], RT = 2.94 minutes; (Program R1, Column Y). |

TABLE 3-continued

| Example No. | Molecular Structure | LCMS |
|---|---|---|
| 14 | 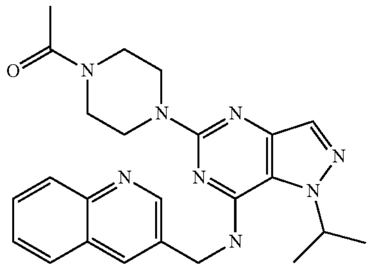 [SMILES: CC(=O)N1CCN(c2nc(NCc3cnc4ccccc4c3)c3c(cnn3C(C)C)n2)CC1] | LCMS: m/z = 445.2 [M + H], RT = 2.05 minutes; (Program R1, Column Y). |
| 15 | 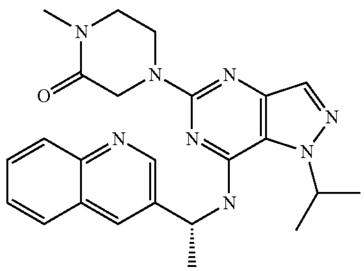 [SMILES: CC(C)n1ncc2nc(N3CCN(C)C(=O)C3)nc(N[C@H](C)c3cnc4ccccc4c3)c21] | LCMS: m/z = 445.2 [M + H], RT = 2.32 minutes; (Program R1, Column Y). |
| 16 | 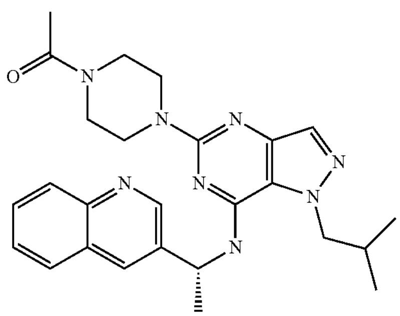 [SMILES: CC(=O)N1CCN(c2nc(N[C@H](C)c3cnc4ccccc4c3)c3c(cnn3CC(C)C)n2)CC1] | LCMS: m/z = 473.0 [M + H], RT = 2.53 minutes; (Program R1, Column Y). |
| 17 | 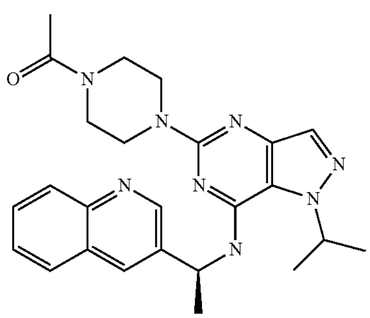 [SMILES: CC(=O)N1CCN(c2nc(N[C@@H](C)c3cnc4ccccc4c3)c3c(cnn3C(C)C)n2)CC1] | LCMS: m/z = 459.2 [M + H], RT = 2.36 minutes; (Program R1, Column Y). |
| 18 | 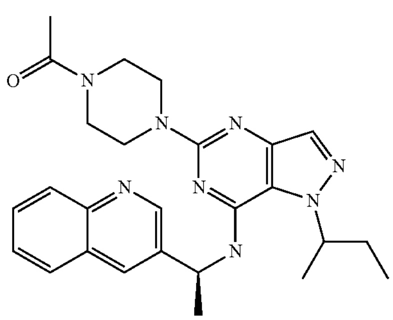 [SMILES: CCC(C)n1ncc2nc(N3CCN(C(C)=O)CC3)nc(N[C@@H](C)c3cnc4ccccc4c3)c21] | LCMS: m/z = 473.0 [M + H], RT = 2.57 minutes; (Program R1, Column Y). |

TABLE 3-continued

| Example No. | Molecular Structure | LCMS |
|---|---|---|
| 19 | 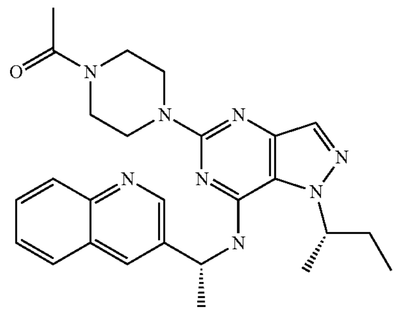 [SMILES: CC[C@H](C)n1ncc2nc(N3CCN(C(C)=O)CC3)nc(N[C@H](C)c3cnc4ccccc4c3)c21] | LCMS: m/z = 473.4 [M + H], RT = 2.62 minutes; (Program R1, Column Y). |
| 20 | 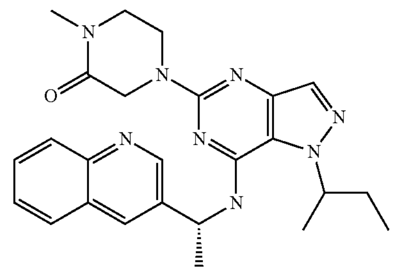 [SMILES: CCC(C)n1ncc2nc(N3CCN(C)C(=O)C3)nc(N[C@H](C)c3cnc4ccccc4c3)c21] | LCMS: m/z = 459.4 [M + H], RT = 2.56 minutes; (Program R1, Column Y). |
| 21 | 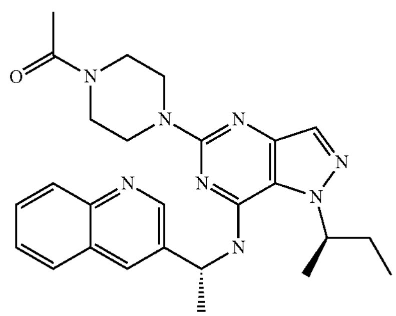 [SMILES: CC[C@@H](C)n1ncc2nc(N3CCN(C(C)=O)CC3)nc(N[C@H](C)c3cnc4ccccc4c3)c21] | LCMS: m/z = 473.2 [M + H], RT = 2.92 minutes; (Program P1, Column W). |
| 22 | 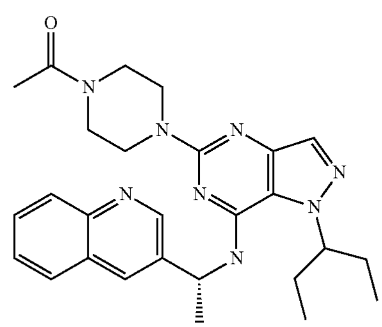 [SMILES: CCC(CC)n1ncc2nc(N3CCN(C(C)=O)CC3)nc(N[C@H](C)c3cnc4ccccc4c3)c21] | LCMS: m/z = 487.6 [M + H], RT = 2.71 minutes; (Program R1, Column Y). |
| 23 | 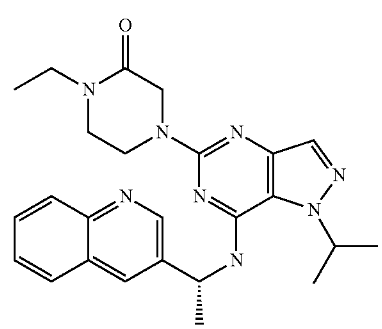 [SMILES: CCN1CCN(c2nc(N[C@H](C)c3cnc4ccccc4c3)c3c(cnn3C(C)C)n2)CC1=O] | LCMS: m/z = 459.4 [M + H], RT = 2.54 minutes; (Program R1, Column Y). |

TABLE 3-continued
| Example No. | Molecular Structure | LCMS |
|---|---|---|
| 24 | 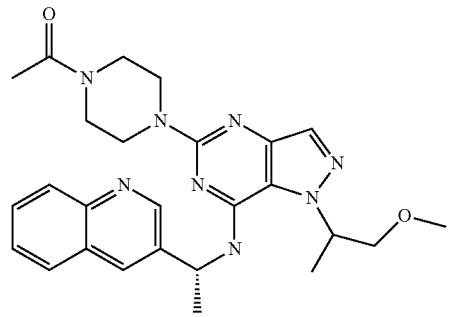 [SMILES: COCC(C)n1ncc2nc(N3CCN(C(C)=O)CC3)nc(N[C@H](C)c3cnc4ccccc4c3)c21] | LCMS: m/z = 489.2 [M + H], RT = 2.48 minutes; (Program R1, Column Y). |
| 25 | 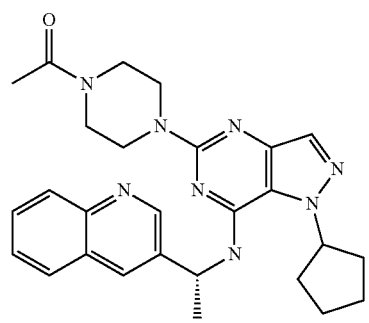 [SMILES: CC(=O)N1CCN(c2nc(N[C@H](C)c3cnc4ccccc4c3)c3c(cnn3C3CCCC3)n2)CC1] | LCMS: m/z = 485.2 [M + H], RT = 2.70 minutes; (Program R1, Column Y). |
| 26 | 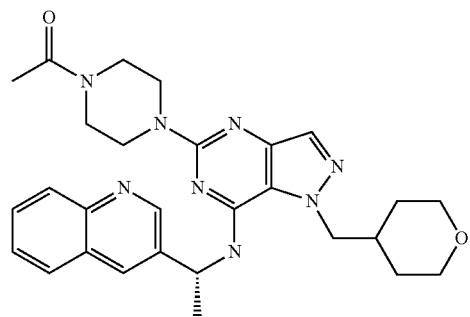 [SMILES: CC(=O)N1CCN(c2nc(N[C@H](C)c3cnc4ccccc4c3)c3c(cnn3CC3CCOCC3)n2)CC1] | LCMS: m/z = 515.2 [M + H], RT = 2.27 minutes; (Program R1, Column Y). |
| 27 | 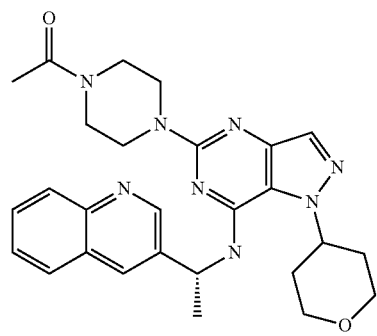 [SMILES: CC(=O)N1CCN(c2nc(N[C@H](C)c3cnc4ccccc4c3)c3c(cnn3C3CCOCC3)n2)CC1] | LCMS: m/z = 501.4 [M + H], RT = 2.38 minutes; (Program R1, Column Y). |

TABLE 3-continued
| Example No. | Molecular Structure | LCMS |
|---|---|---|
| 28 | 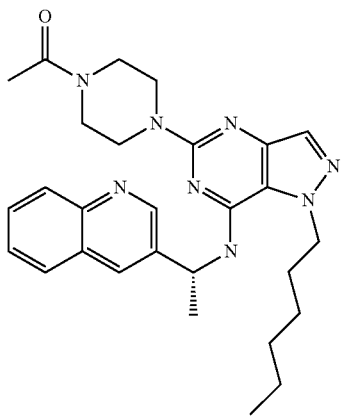 [SMILES: CCCCCCn1ncc2nc(N3CCN(C(C)=O)CC3)nc(N[C@H](C)c3cnc4ccccc4c3)c21] | LCMS: m/z = 501.4 [M + H], RT = 3.08 minutes; (Program R1, Column Y). |
| 29 | 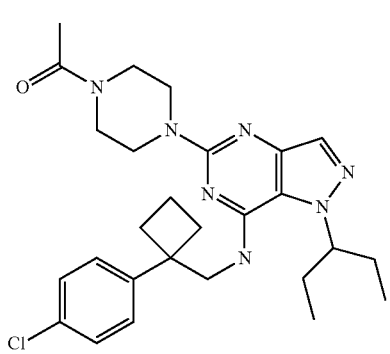 [SMILES: CCC(CC)n1ncc2nc(N3CCN(C(C)=O)CC3)nc(NCC3(c4ccc(Cl)cc4)CCC3)c21] | LCMS: m/z = 510.0 [M + H], RT = 3.65 minutes; (Program P1, Column Y). |
| 30 | 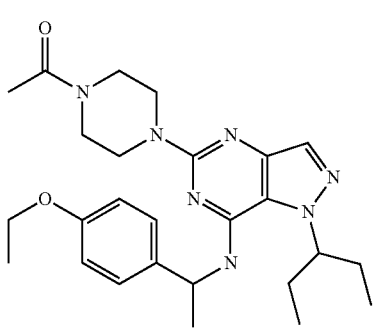 [SMILES: CCOc1ccc(C(C)Nc2nc(N3CCN(C(C)=O)CC3)nc3cnn(C(CC)CC)c23)cc1] | LCMS: m/z = 480.2 [M + H], RT = 3.32 minutes; (Program P1, Column Y). |
| 31 | 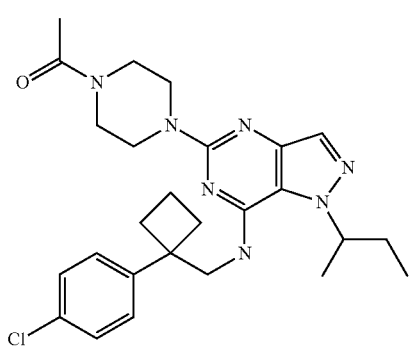 [SMILES: CCC(C)n1ncc2nc(N3CCN(C(C)=O)CC3)nc(NCC3(c4ccc(Cl)cc4)CCC3)c21] | LCMS: m/z = 496.0 [M + H], RT = 3.57 minutes; (Program P1, Column Y). |

TABLE 3-continued

| Example No. | Molecular Structure | LCMS |
|---|---|---|
| 32 | 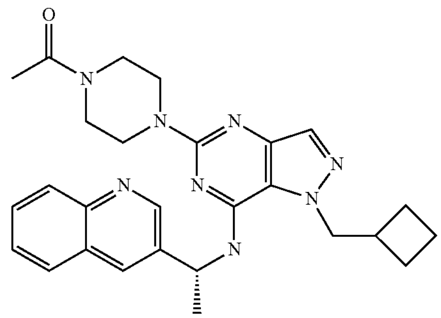 [SMILES: CC(=O)N1CCN(c2nc(N[C@H](C)c3cnc4ccccc4c3)c3c(cnn3CC3CCC3)n2)CC1] | LCMS: m/z = 485.2 [M + H], RT = 2.72 minutes; (Program R1, Column Y). |
| 33 | 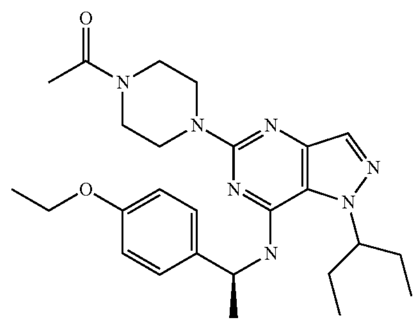 [SMILES: CCOc1ccc([C@H](C)Nc2nc(N3CCN(C(C)=O)CC3)nc3cnn(C(CC)CC)c23)cc1] | LCMS: m/z = 480.2 [M + H], RT = 3.32 minutes; (Program P1, Column Y). |
| 34 | 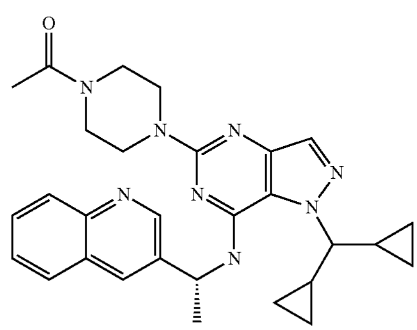 [SMILES: CC(=O)N1CCN(c2nc(N[C@H](C)c3cnc4ccccc4c3)c3c(cnn3C(C3CC3)C3CC3)n2)CC1] | LCMS: m/z = 511.4 [M + H], RT = 2.66 minutes; (Program R1, Column Y). |
| 35 | 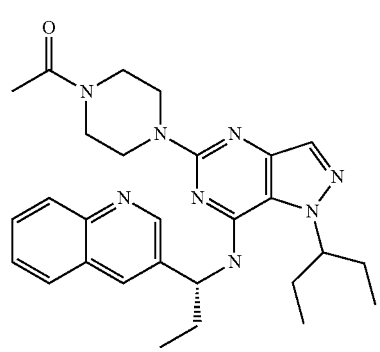 [SMILES: CCC(CC)n1ncc2nc(N3CCN(C(C)=O)CC3)nc(N[C@H](CC)c3cnc4ccccc4c3)c21] | LCMS: m/z = 500.8 [M + H], RT = 3.09 minutes; (Program R1, Column Y). |

TABLE 3-continued

| Example No. | Molecular Structure | LCMS |
|---|---|---|
| 36 | 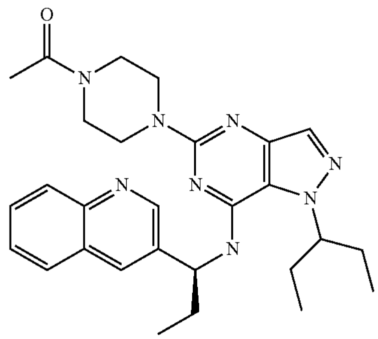 [SMILES: CCC(CC)n1ncc2nc(N3CCN(C(C)=O)CC3)nc(N[C@@H](CC)c3cnc4ccccc4c3)c21] | LCMS: m/z = 500.8 [M + H], RT = 3.10 minutes; (Program R1, Column Y). |
| 37 | 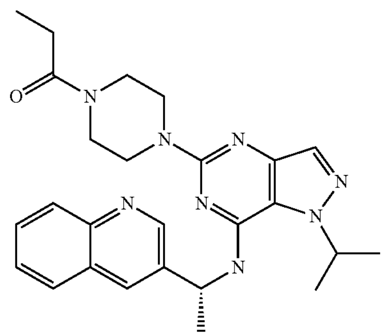 [SMILES: CCC(=O)N1CCN(c2nc(N[C@H](C)c3cnc4ccccc4c3)c3c(cnn3C(C)C)n2)CC1] | LCMS: m/z = 473.0 [M + H], RT = 2.86 minutes; (Program R1, Column Y). |
| 38 | 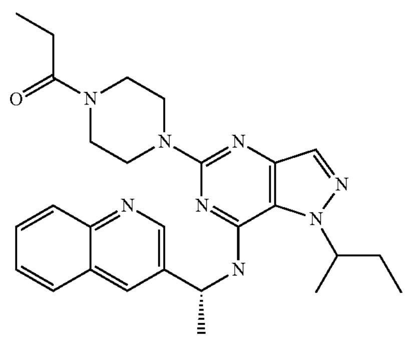 [SMILES: CCC(=O)N1CCN(c2nc(N[C@H](C)c3cnc4ccccc4c3)c3c(cnn3C(C)CC)n2)CC1] | LCMS: m/z = 486.2 [M + H], RT = 3.76 minutes; (Program R1, Column Y). |
| 39 | 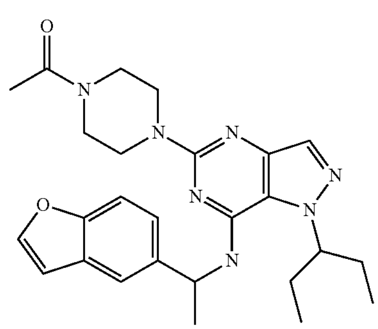 | LCMS: m/z = 475.9 [M + H], RT = 3.19 minutes; (Program R1, Column Y). |

TABLE 3-continued

| Example No. | Molecular Structure | LCMS |
|---|---|---|
| 40 | 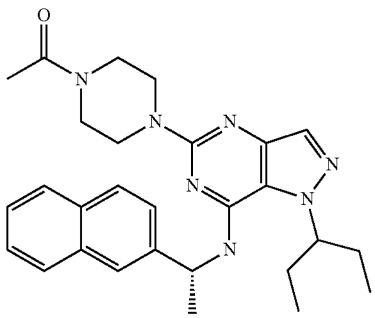 [SMILES: CCC(CC)n1ncc2nc(N3CCN(C(C)=O)CC3)nc(N[C@H](C)c3ccc4ccccc4c3)c21] | LCMS: m/z = 485.8 [M + H], RT = 3.35 minutes; (Program R1, Column Y). |
| 41 | 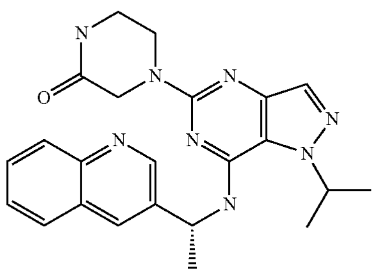 [SMILES: CC(C)n1ncc2nc(N3CCNC(=O)C3)nc(N[C@H](C)c3cnc4ccccc4c3)c21] | LCMS: m/z = 430.7 [M + H], RT = 2.40 minutes; (Program R1, Column Y). |
| 42 | 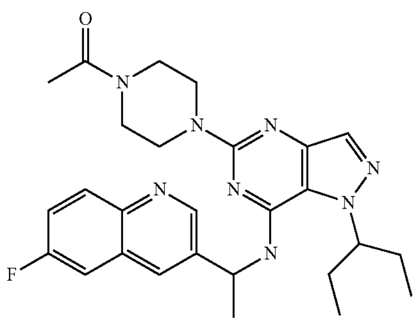 [SMILES: CCC(CC)n1ncc2nc(N3CCN(C(C)=O)CC3)nc(NC(C)c3cnc4ccc(F)cc4c3)c21] | LCMS: m/z = 504.8 [M + H], RT = 3.12 minutes; (Program R1, Column Y). |
| 43 | 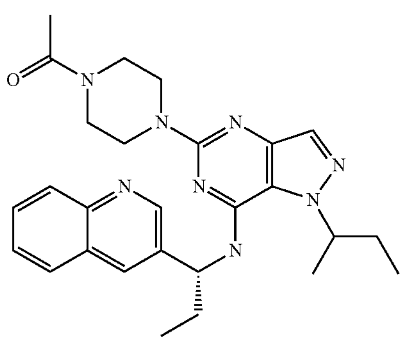 [SMILES: CCC(C)n1ncc2nc(N3CCN(C(C)=O)CC3)nc(N[C@H](CC)c3cnc4ccccc4c3)c21] | LCMS: m/z = 486.7 [M + H], RT = 3.03 minutes; (Program R1, Column Y). |
| 44 | 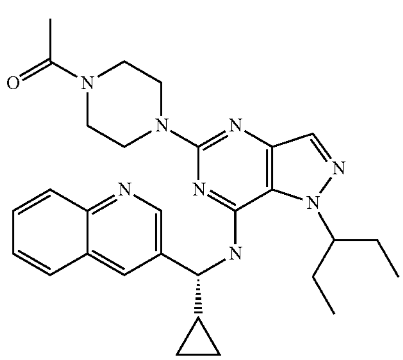 [SMILES: CCC(CC)n1ncc2nc(N3CCN(C(C)=O)CC3)nc(N[C@@H](c3cnc4ccccc4c3)C3CC3)c21] | LCMS: m/z = 513.2 [M + H], RT = 3.08 minutes; (Program R1, Column Y). |

TABLE 3-continued

| Example No. | Molecular Structure | LCMS |
|---|---|---|
| 45 | 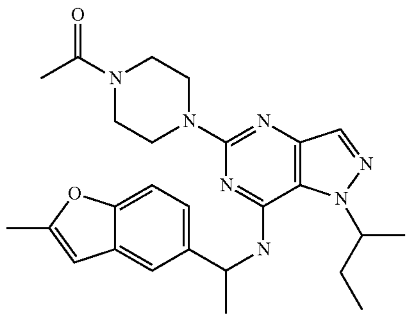 [SMILES: CCC(C)n1ncc2nc(N3CCN(C(C)=O)CC3)nc(NC(C)c3ccc4oc(C)cc4c3)c21] | LCMS: m/z = 476.5 [M + H], RT = 3.25 minutes; (Program R1, Column Y). |
| 46 | 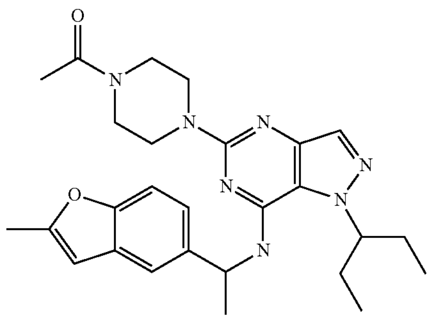 [SMILES: CCC(CC)n1ncc2nc(N3CCN(C(C)=O)CC3)nc(NC(C)c3ccc4oc(C)cc4c3)c21] | LCMS: m/z = 490.0 [M + H], RT = 3.29 minutes; (Program R1, Column Y). |
| 47 | 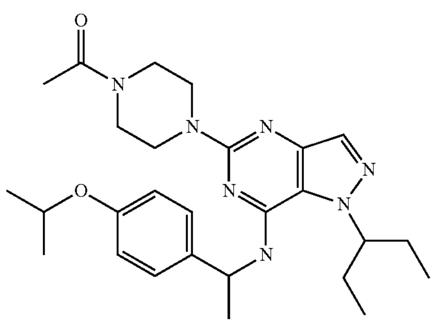 [SMILES: CCC(CC)n1ncc2nc(N3CCN(C(C)=O)CC3)nc(NC(C)c3ccc(OC(C)C)cc3)c21] | LCMS: m/z = 494.0 [M + H], RT = 3.22 minutes; (Program R1, Column Y). |
| 48 | 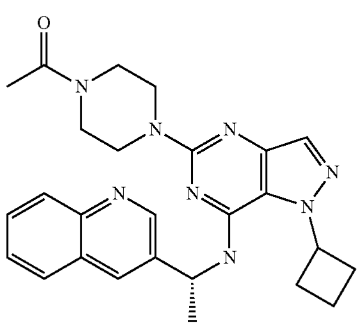 [SMILES: CC(=O)N1CCN(c2nc(N[C@H](C)c3cnc4ccccc4c3)c3c(cnn3C3CCC3)n2)CC1] | LCMS: m/z = 471.0 [M + H], RT = 2.79 minutes; (Program R1, Column Y). |
| 49 | 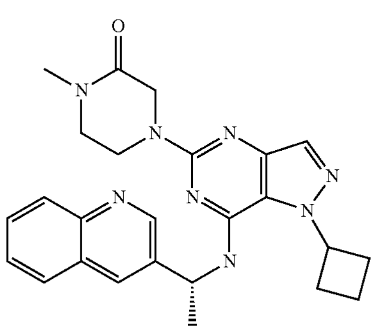 [SMILES: C[C@@H](Nc1nc(N2CCN(C)C(=O)C2)nc2cnn(C3CCC3)c12)c1cnc2ccccc2c1] | LCMS: m/z = 457.4 [M + H], RT = 2.83 minutes; (Program R1, Column Y). |

TABLE 3-continued

| Example No. | Molecular Structure | LCMS |
|---|---|---|
| 50 | 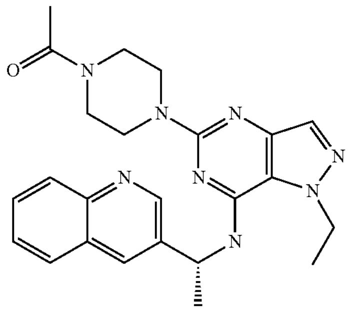 [SMILES: CCn1ncc2nc(N3CCN(C(C)=O)CC3)nc(N[C@H](C)c3cnc4ccccc4c3)c21] | LCMS: m/z = 445.6 [M + H], RT = 2.72 minutes; (Program P1, Column Y). |
| 51 | 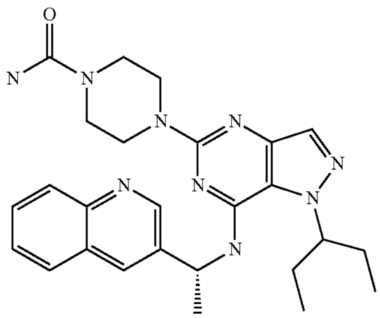 [SMILES: CCC(CC)n1ncc2nc(N3CCN(C(N)=O)CC3)nc(N[C@H](C)c3cnc4ccccc4c3)c21] | LCMS: m/z = 488.2 [M + H], RT = 2.87 minutes; (Program R1, Column Y). |
| 52 | 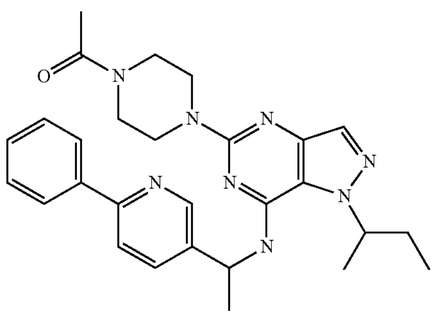 [SMILES: CCC(C)n1ncc2nc(N3CCN(C(C)=O)CC3)nc(NC(C)c3ccc(-c4ccccc4)nc3)c21] | LCMS: m/z = 499.2 [M + H], RT = 3.15 minutes; (Program R1, Column Y). |
| 53 | 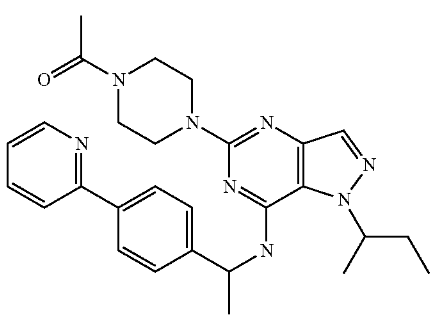 [SMILES: CCC(C)n1ncc2nc(N3CCN(C(C)=O)CC3)nc(NC(C)c3ccc(-c4ccccn4)cc3)c21] | LCMS: m/z = 499.1 [M + H], RT = 2.92 minutes; (Program R1, Column Y). |
| 54 | 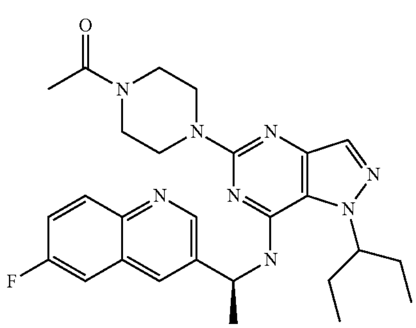 [SMILES: CCC(CC)n1ncc2nc(N3CCN(C(C)=O)CC3)nc(N[C@@H](C)c3cnc4ccc(F)cc4c3)c21] | LCMS: m/z = 505.2 [M + H], RT = 3.09 minutes; (Program R1, Column Y). |

TABLE 3-continued

| Example No. | Molecular Structure | LCMS |
|---|---|---|
| 55 | 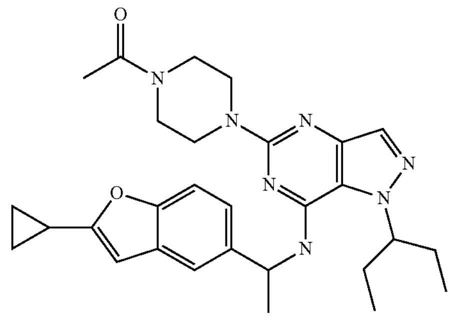 [SMILES: CCC(CC)n1ncc2nc(N3CCN(C(C)=O)CC3)nc(NC(C)c3ccc4oc(C5CC5)cc4c3)c21] | LCMS: m/z = 516.0 [M + H], RT = 3.37 minutes; (Program R1, Column Y). |
| 56 | 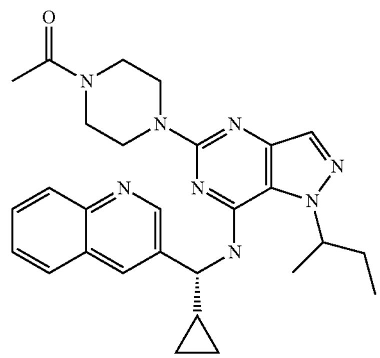 [SMILES: CCC(C)n1ncc2nc(N3CCN(C(C)=O)CC3)nc(N[C@@H](c3cnc4ccccc4c3)C3CC3)c21] | LCMS: m/z = 499.2 [M + H], RT = 3.02 minutes; (Program R1, Column Y). |
| 57 | 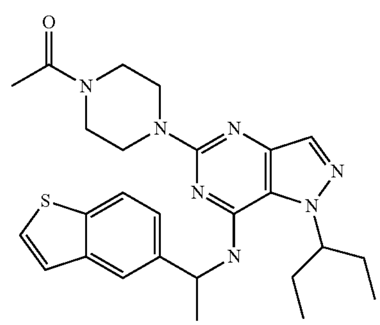 [SMILES: CCC(CC)n1ncc2nc(N3CCN(C(C)=O)CC3)nc(NC(C)c3ccc4sccc4c3)c21] | LCMS: m/z = 492.2 [M + H], RT = 3.27 minutes; (Program R1, Column Y). |
| 58 | 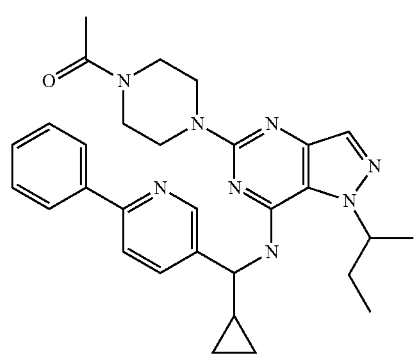 [SMILES: CCC(C)n1ncc2nc(N3CCN(C(C)=O)CC3)nc(NC(c3ccc(-c4ccccc4)nc3)C3CC3)c21] | LCMS: m/z = 525.4 [M + H], RT = 3.23 minutes; (Program R1, Column Y). |

TABLE 3-continued
| Example No. | Molecular Structure | LCMS |
|---|---|---|
| 59 | 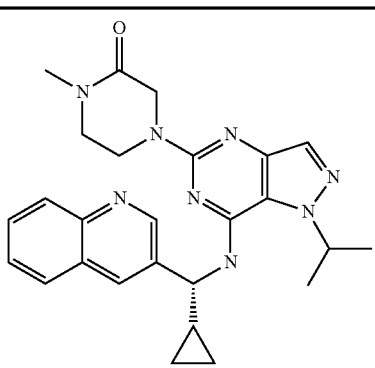 | LCMS: m/z = 471.2 [M + H], RT = 2.90 minutes; (Program R1, Column Y). |
| 60 | 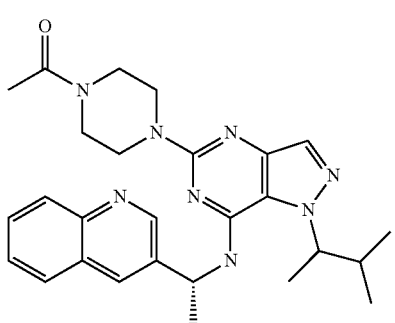 | LCMS: m/z = 487.2 [M + H], RT = 3.00 minutes; (Program R1, Column Y). |
| 61 | 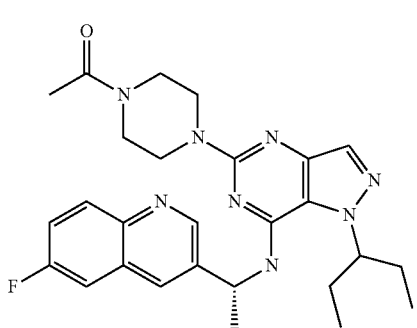 | LCMS: m/z = 505.2 [M + H], RT = 3.09 minutes; (Program R1, Column Y). |
| 62 | 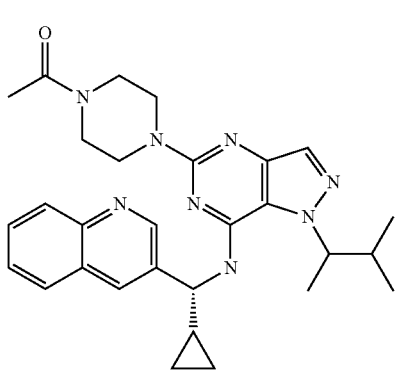 [SMILES: CC(=O)N1CCN(c2nc(N[C@@H](c3cnc4ccccc4c3)C3CC3)c3c(cnn3C(C)C(C)C)n2)CC1] | LCMS: m/z = 513.3 [M + H], RT = 3.12 minutes; (Program R1, Column Y). |

TABLE 3-continued

| Example No. | Molecular Structure | LCMS |
|---|---|---|
| 63 | 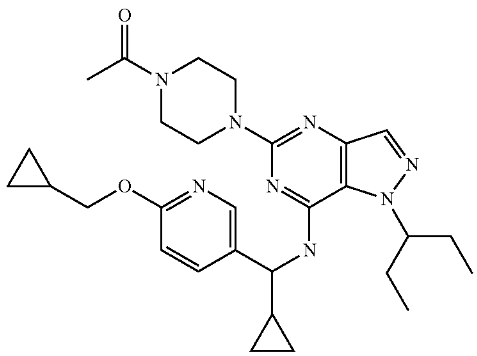 [SMILES: CCC(CC)n1ncc2nc(N3CCN(C(C)=O)CC3)nc(NC(c3ccc(OCC4CC4)nc3)C3CC3)c21] | LCMS: m/z = 533.5 [M + H], RT = 3.33 minutes; (Program R1, Column Y). |
| 64 | 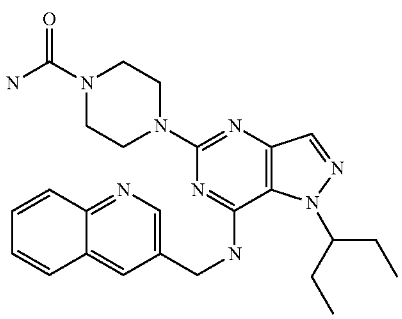 [SMILES: CCC(CC)n1ncc2nc(N3CCN(C(N)=O)CC3)nc(NCc3cnc4ccccc4c3)c21] | LCMS: m/z = 474.2 [M + H], RT = 2.30 minutes; (Program R1, Column W). |
| 65 | 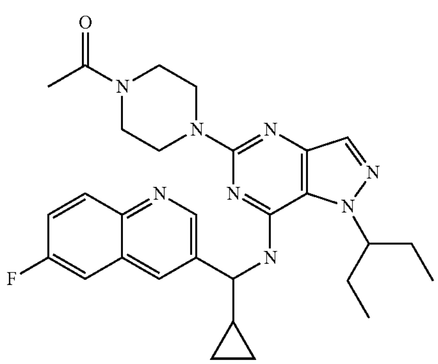 [SMILES: CCC(CC)n1ncc2nc(N3CCN(C(C)=O)CC3)nc(NC(c3cnc4ccc(F)cc4c3)C3CC3)c21] | LCMS: m/z = 531.3 [M + H], RT = 2.86 minutes; (Program R1, Column W). |
| 66 | 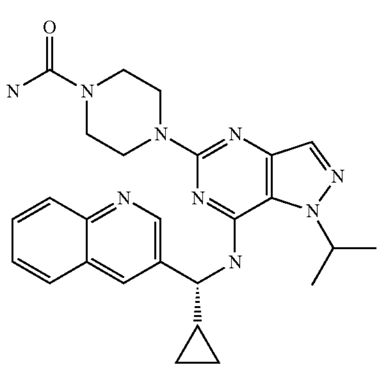 [SMILES: CC(C)n1ncc2nc(N3CCN(C(N)=O)CC3)nc(N[C@@H](c3cnc4ccccc4c3)C3CC3)c21] | LCMS: m/z = 486.2 [M + H], RT = 2.31 minutes; (Program R1, Column W). |

TABLE 3-continued
| Example No. | Molecular Structure | LCMS |
|---|---|---|
| 67 | 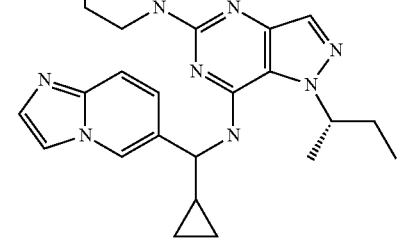 | LCMS: m/z = 489.3 [M + H], RT = 1.72 minutes; (Program R1, Column W). |
| 68 | 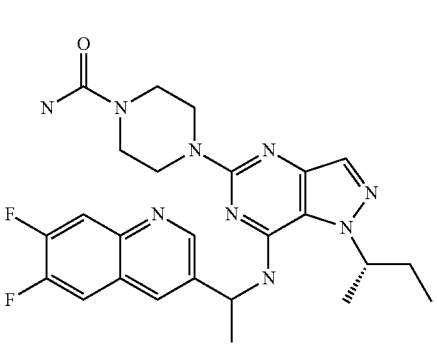 [SMILES: CC[C@H](C)n1ncc2nc(N3CCN(C(N)=O)CC3)nc(NC(C)c3cnc4cc(F)c(F)cc4c3)c21] | LCMS: m/z = 510.3 [M + H], RT = 2.71 minutes; (Program R1, Column W). |
| 69 | 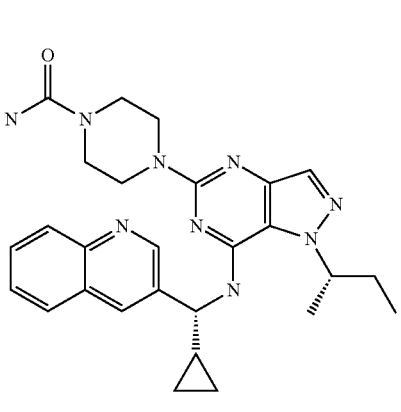 | LCMS: m/z = 500.4 [M + H], RT = 2.57 minutes; (Program R1, Column W). |
| 70 | 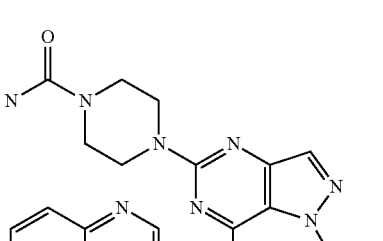 | LCMS: m/z = 500.4 [M + H], RT = 2.57 minutes; (Program R1, Column W). |

TABLE 3-continued

| Example No. | Molecular Structure | LCMS |
|---|---|---|
| 71 | 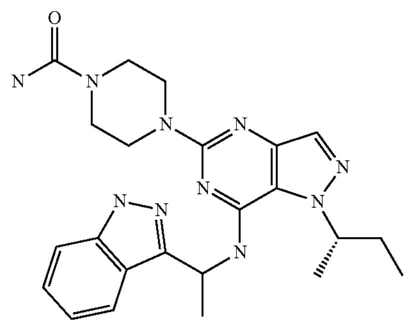 [SMILES: CC[C@H](C)n1ncc2nc(N3CCN(C(N)=O)CC3)nc(NC(C)c3n[nH]c4ccccc34)c21] | LCMS: m/z = 463.2 [M + H], RT = 5.25 minutes; (Program R1, Column W). |
| 72 | 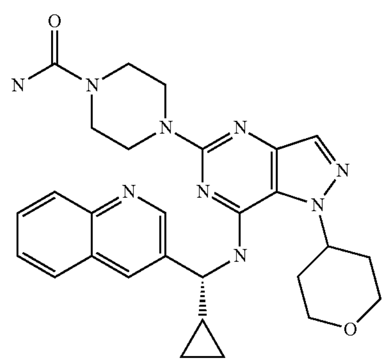 [SMILES: NC(=O)N1CCN(c2nc(N[C@@H](c3cnc4ccccc4c3)C3CC3)c3c(cnn3C3CCOCC3)n2)CC1] | LCMS: m/z = 528.3 [M + H], RT = 2.25 minutes; (Program R1, Column W). |
| 73 | 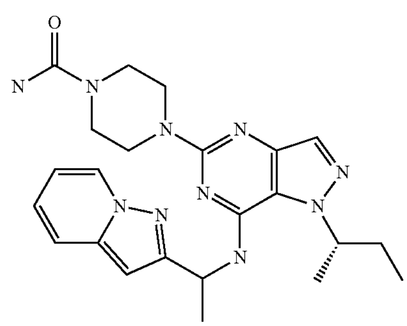 [SMILES: CC[C@H](C)n1ncc2nc(N3CCN(C(N)=O)CC3)nc(NC(C)c3cc4ccccn4n3)c21] | LCMS: m/z = 463.0 [M + H], RT = 2.86 minutes; (Program P1, Column Y). |
| 74 | 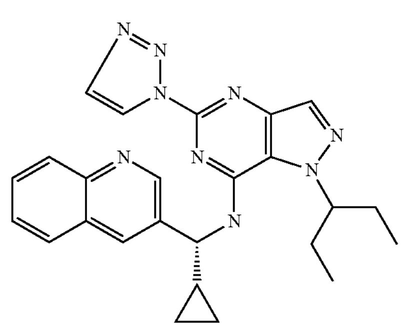 [SMILES: CCC(CC)n1ncc2nc(-n3ccnn3)nc(N[C@@H](c3cnc4ccccc4c3)C3CC3)c21] | LCMS: m/z = 454.6 [M + H], RT = 3.46 minutes; (Program R1, Column W). |

TABLE 3-continued

| Example No. Molecular Structure | LCMS |
|---|---|
| 75 | LCMS: m/z = 499.3 [M + H], RT = 2.55 minutes; (Program R1, Column W). |
| 76 | LCMS: m/z = 483.4 [M + H], RT = 3.10 minutes; (Program R1, Column W). |
| 77 | LCMS: m/z = 440.4 [M + H], RT = 3.36 minutes; (Program R1, Column W). |
| 78 | LCMS: m/z = 441.4 [M + H], RT = 3.32 minutes; (Program R1, Column W). |

TABLE 3-continued

| Example No. | Molecular Structure | LCMS |
|---|---|---|
| 79 | 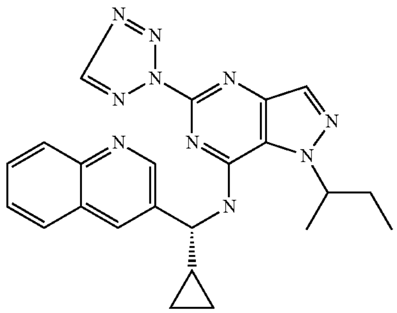 [SMILES: CCC(C)n1ncc2nc(-n3ncnn3)nc(N[C@@H](c3cnc4ccccc4c3)C3CC3)c21] | LCMS: m/z = 441.4 [M + H], RT = 3.43 minutes; (Program R1, Column W). |
| 80 | 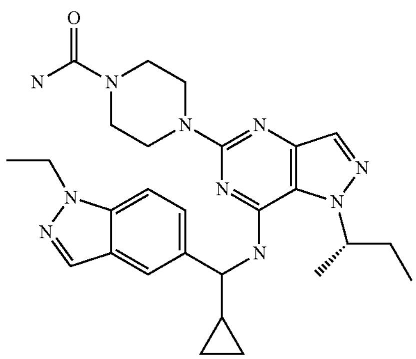 [SMILES: CC[C@H](C)n1ncc2nc(N3CCN(C(N)=O)CC3)nc(NC(c3ccc4c(cnn4CC)c3)C3CC3)c21] | LCMS: m/z = 517.0 [M + H], RT = 3.26 minutes; (Program R1, Column W). |
| 81 | 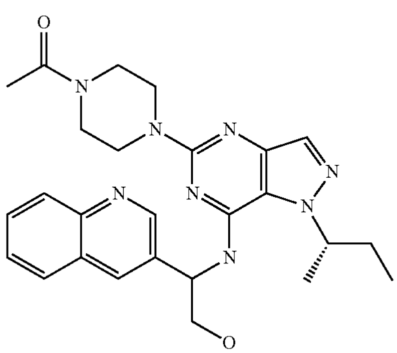 [SMILES: CC[C@H](C)n1ncc2nc(N3CCN(C(C)=O)CC3)nc(NC(CO)c3cnc4ccccc4c3)c21] | LCMS: m/z = 489.3 [M + H], RT = 6.09 minutes; (Program P2, Column V). |
| 82 | 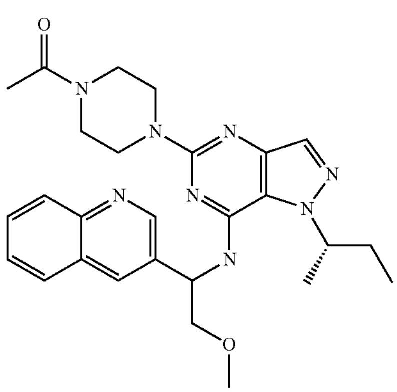 [SMILES: CC[C@H](C)n1ncc2nc(N3CCN(C(C)=O)CC3)nc(NC(COC)c3cnc4ccccc4c3)c21] | LCMS: m/z = 503.2 [M + H], RT = 3.28 minutes; (Program R1, Column W). |

TABLE 3-continued
| Example No. | Molecular Structure | LCMS |
|---|---|---|
| 83 | 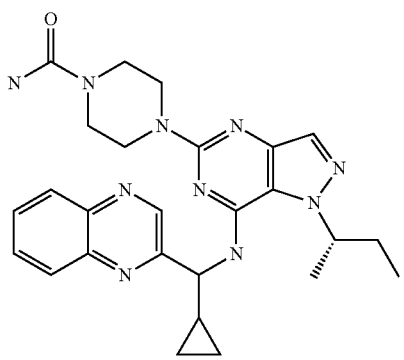 [SMILES: CC[C@H](C)n1ncc2nc(N3CCN(C(N)=O)CC3)nc(NC(c3cnc4ccccc4n3)C3CC3)c21] | LCMS: m/z = 501.4 [M + H], RT = 3.40 minutes; (Program R1, Column W). |
| 84 | 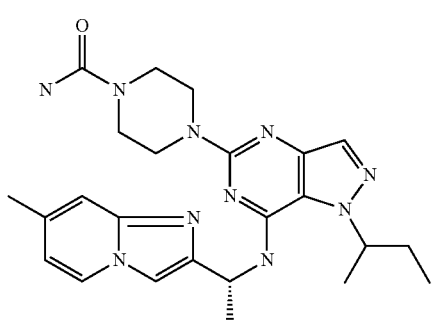 | LCMS: m/z = 477.4 [M + H], RT = 2.08 minutes; (Program R1, Column W). |
| 85 | 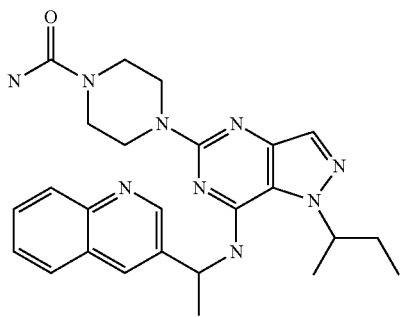 [SMILES: CCC(C)n1ncc2nc(N3CCN(C(N)=O)CC3)nc(NC(C)c3cnc4ccccc4c3)c21] | LCMS: m/z = 474.2 [M + H], RT = 2.92 minutes; (Program R1, Column W). |
| 86 | 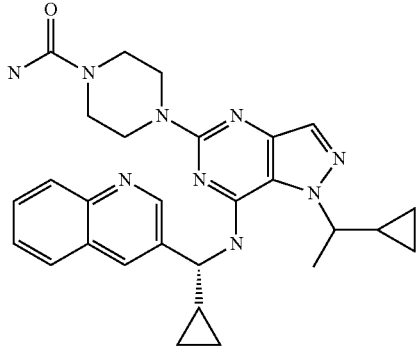 [SMILES: CC(C1CC1)n1ncc2nc(N3CCN(C(N)=O)CC3)nc(N[C@@H](c3cnc4ccccc4c3)C3CC3)c21] | LCMS: m/z = 512.2 [M + H], RT = 3.16 minutes; (Program R1, Column W). |

| Example No. | Molecular Structure | LCMS |
|---|---|---|
| 87 | 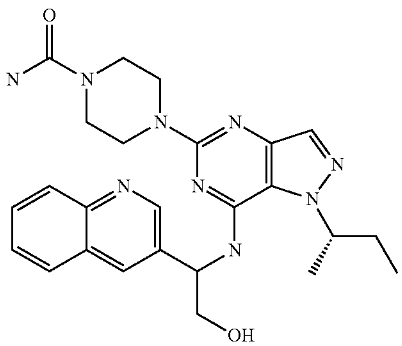 [SMILES: CC[C@H](C)n1ncc2nc(N3CCN(C(N)=O)CC3)nc(NC(CO)c3cnc4ccccc4c3)c21] | LCMS: m/z = 490.2 [M + H], RT = 2.79, 2.88 minutes; (Program R1, Column W). |
| 88 | 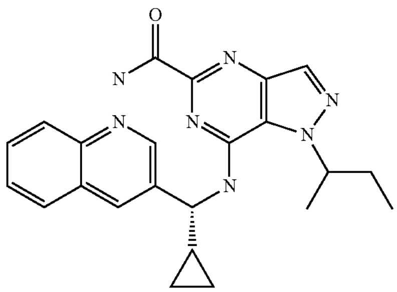 [SMILES: CCC(C)n1ncc2nc(C(N)=O)nc(N[C@@H](c3cnc4ccccc4c3)C3CC3)c21] | LCMS: m/z = 416.2 [M + H], RT = 2.93 minutes; (Program R1, Column W). |

Examples 78 and 79 are isomers, and were obtained from S$_N$Ar reaction of compound VII and tetrazole. Preparative HPLC was carried out with water/acetonitrile using 0.1% formic acid buffer to isolate the isomers. As the actual structure of a given isomer could not be determined, structures were assigned arbitrarily where Example 78 represented the peak eluting first with shorter retention time and Example 79 eluting afterwards with higher retention time.

Example 88 was synthesized by similar S$_N$Ar strategy by refluxing with NaCN and DABCO in DMSO/water (1:1), that resulted in this compound, which is a partially hydrolyzed —CONH$_2$ analog instead of the anticipated —CN compound.

Examples 89-93—Scheme 22 below is a representative synthesis of 1-{4-[1-sec-Butyl-74(R)-1-quinolin-3-yl-ethylamino)-1H-pyrazolo[4,3-d]pyrimidin-5-yl]-piperazin-1-yl}-ethanone, 1-{4-[3-Bromo-1-sec-butyl-7-((R)-1-quinolin-3-yl-ethylamino)-1H-pyrazolo[4,3-d]pyrimidin-5-yl]-piperazin-1-yl}-ethanone, 5-(4-Acetyl-piperazin-1-yl)-1-sec-butyl-7-((R)-1-quinolin-3-yl-ethylamino)-1H-pyrazolo[4,3-d]pyrimidine-3-carbonitrile, 1-{4-[1-sec-Butyl-3-methyl-7-((R)-1-quinolin-3-yl-ethylamino)-1H-pyrazolo[4,3-d]pyrimidin-5-yl]-piperazin-1-yl}-ethanone and 1-{4-[1-sec-Butyl-3-cyclopropyl-7-((R)-1-quinolin-3-yl-ethylamino)-1H-pyrazolo[4,3-d]pyrimidin-5-yl]-piperazin-1-yl}-ethanone Intermediate VIIa was synthesized in a similar manner to that of VII.

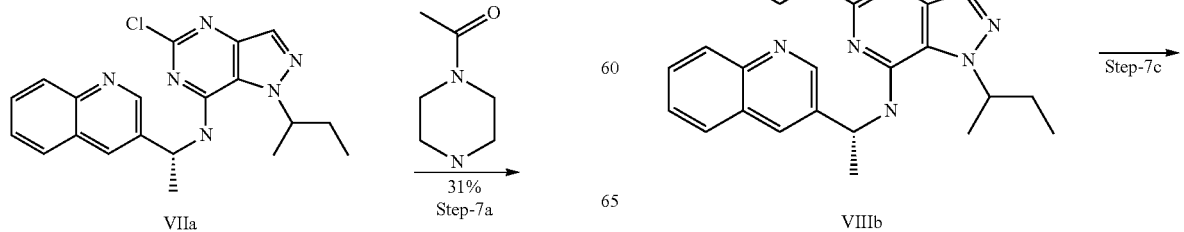

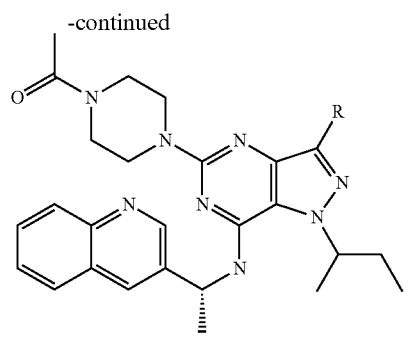

VIIIc, R = cyano (20%)
VIIId, R = methyl (59%)
VIIIe, R = cyclopropyl (14%)

Example 89: 1-{4-[1-sec-Butyl-7-((R)-1-quinolin-3-yl-ethylamino)-1H-pyrazolo[4,3-d]pyrimidin-5-yl]-piperazin-1-yl}-ethanone (VIIIa)

To a solution of VIIa (100 mg, 0.26 mmol, 1 eq) in n-butyl alcohol (5 mL) were added N-acetyl piperazine (41 mg, 0.32 mmol, 1.23 eq) and DIPEA (0.14 mL, 0.79 mmol, 3 eq) and the resulting mixture was refluxed for 48 h. The reaction mixture was cooled to RT, concentrated in vacuo, the residue was diluted with water (20 mL). The organic components were extracted with $CH_2Cl_2$ (50 mL), DCM layer was dried over anhydrous sodium sulfate and concentrated in vacuo. The crude material was purified by flash chromatography (Combiflash) using 100-200 mesh silica gel eluting with 3% MeOH/$CH_2Cl_2$ to obtain compound VIIIa (40 mg, 31%) as off white solid.

$^1$H NMR (400 MHz, DMSO-$d_6$) δ 9.06-9.04 (m, 1H), 8.35 (br s, 1H), 8.00-7.93 (m, 2H), 7.72-7.69 (m, 2H), 7.61-7.57 (m, 1H), 7.40-7.34 (m, 1H), 5.64-5.58 (m, 1H), 5.04-5.00 (m, 1H), 3.54-3.19 (m, 8H), 1.98-1.94 (m, 3H), 1.88-1.85 (m, 1H), 1.79-1.74 (m, 4H), 1.54-1.49 (m, 3H), 0.75-0.66 (m, 3H);

LCMS: m/z=473.0 [M+H], RT=2.51 minutes; (Program R1, Column Y).

Example 90: 1-{4-[3-Bromo-1-sec-butyl-7-((R)-1-quinolin-3-yl-ethylamino)-1H-pyrazolo[4,3-d]pyrimidin-5-yl]-piperazin-1-yl}-ethanone (VIIIb)

To a solution of compound VIIIa (30 mg, 0.06 mmol, 1 eq) in dry THF (5 mL) was added NBS (12 mg, 0.06 mmol, 1 eq) at 0° C. and the resulting mixture was stirred for 20 minutes at 23° C. The reaction mixture was diluted with aq. $NaHCO_3$ (5 mL) and the organic components were extracted with $CH_2Cl_2$ (20 mL), organic layer was dried over anhyd. sodium sulfate and concentrated in vacuo. The crude material was purified by flash chromatography (Combiflash) using 100-200 mesh silica gel eluting with 3% MeOH/$CH_2Cl_2$ to obtain compound VIIIb (29 mg, 88%) as white solid.

$^1$H NMR (400 MHz, DMSO-$d_6$) δ 9.06-9.03 (m, 1H), 8.35 (s, 1H), 8.00-7.94 (m, 2H), 7.73-7.69 (m, 1H), 7.61-7.53 (m, 2H), 5.63-5.61 (m, 1H), 5.15-4.95 (m, 1H), 3.57-3.30 (m, 8H), 1.96 (d, J=7 Hz, 3H), 1.77-1.73 (m, 5H), 1.53-1.49 (m, 3H), 0.76-0.68 (m, 3H);

LCMS: m/z=551.0 [M+], 553.0 [M+2], RT=3.09 minutes; (Program R1, Column Y).

Example 91: 5-(4-Acetyl-piperazin-1-yl)-1-sec-butyl-7-((R)-1-quinolin-3-yl-ethylamino)-1H-pyrazolo[4,3-d]pyrimidine-3-carbonitrile (VIIIc)

To a solution of compound VIIIb (25 mg, 0.05 mmol, 1 eq) in dry DMF (2 mL) was added CuCN (19 mg, 0.23 mmol, 5 eq) and the resulting mixture was heated in a sealed tube at 200° C. for 12 h. The reaction mixture was cooled to RT, filtered through Celite and solids were washed with ethyl acetate (50 mL). Combined filtrate was diluted with water (20 ml) and the organic components were extracted with ethyl acetate (20 mL). The organic layer was dried over anhyd. sodium sulfate and concentrated in vacuo. The crude material was purified by flash chromatography (Combiflash) using 100-200 mesh silica gel eluting with 3% MeOH/$CH_2Cl_2$ to obtain compound VIIIc (5 mg 20%) as off white solid.

LCMS: m/z=498.0 [M+H], RT=3.16 minutes; (Program R1, Column Y).

Example 92: 1-{4-[1-sec-Butyl-3-methyl-7-((R)-1-quinolin-3-yl-ethylamino)-1H-pyrazolo[4,3-d]pyrimidin-5-yl]-piperazin-1-yl}-ethanone (VIIId)

To a solution of compound VIIIb (40 mg, 0.07 mmol, 1 eq) in a mixture of dioxane and water (3:2 mL) were added trimethyl boraxane (0.03 mL, 0.22 mmol, 3 eq), $K_2CO_3$ (30 mg, 0.22 mmol, 3 eq) and the mixture was degassed with Argon for 30 min. Pd(PPh$_3$)$_4$ was added to it and the resulting mixture was further degassed with Argon for another 15 min and heated at 90° C. for 12 h. The reaction mixture was cooled to RT, filtered through Celite and solids were washed with ethyl acetate (20 mL). The filtrate was diluted with water (20 ml) and the organic components were extracted with ethyl acetate (50 mL), ethyl acetate layer was dried over anhydrous sodium sulfate and concentrated in vacuo. The crude material was purified by Prep TLC using 2.5% MeOH/$CH_2Cl_2$ to obtain compound VIIId (20 mg, 59%) as off white solid.

$^1$H NMR (400 MHz, DMSO-$d_6$) δ 9.05-9.03 (m, 1H), 8.33 (s, 1H), 8.00-7.92 (m, 2H), 7.70 (t, J=7 Hz, 1H), 7.60-7.58 (m, 1H), 7.34-7.28 (m, 1H), 5.64-5.58 (m, 1H), 5.00-4.93 (m, 1H), 3.54-3.20 (m, 8H), 2.26 (s, 3H), 1.99-1.95 (m, 3H), 1.9-1.72 (m, 5H), 1.50-1.47 (m, 3H), 0.74-0.65 (m, 3H);

LCMS: m/z=487.2 [M+H], RT=2.65 minutes; (Program R1, Column Y).

Example 93: 1-{4-[1-sec-Butyl-3-cyclopropyl-7-((R)-1-quinolin-3-yl-ethylamino)-1H-pyrazolo[4,3-d]pyrimidin-5-yl]-piperazin-1-yl}-ethanone To a solution of compound VIIIb (40 mg, 0.07 mmol, 1 eq) in a mixture of dioxane and water (3:2 mL) were added cyclopropyl boronic acid (13 mg, 0.15 mmol, 2.1 eq), $Na_2CO_3$ (23 mg, 0.22 mmol, 3.1 eq), tricyclohexyl phosphine (2 mg, 0.01 mmol, 0.1 eq) and the mixture was degassed with Argon for 15 min. Pd(OAc)$_2$ (1 mg, 0.004 mmol, 0.05 eq) was added to it and the resulting mixture was further degassed with Argon for another 30 min and heated at 90° C. for 14 h. The reaction mixture was cooled to RT, filtered through Celite and solids were washed with ethyl acetate (20 mL). The filtrate was diluted with water and the organic components were extracted with ethyl acetate (50 mL), ethyl acetate layer was dried over anhydrous sodium sulfate and concentrated in vacuo. The crude material was purified by Prep TLC using 2.5% MeOH/$CH_2Cl_2$ to obtain compound VIIIe (5 mg, 14%) as off white solid.

LCMS: m/z=513.4 [M+H], RT=3.04 minutes; (Program R1, Column Y).

Examples 94-107

The 14 compounds shown in Table 4 below were synthesized using Scheme-22. The compound of Example 95 was obtained as a side product during the synthesis of the compound of Example 103, due to the partial hydrolysis of the —CN group.

TABLE 4

| Example No. | Molecular Structure | LCMS |
|---|---|---|
| 94 | 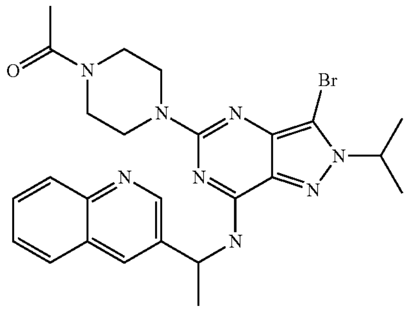 [SMILES: CC(=O)N1CCN(c2nc(NC(C)c3cnc4ccccc4c3)c3nn(C(C)C)c(Br)c3n2)CC1] | LCMS: m/z = 537.2 [M+], 539.2 [M + 2], RT = 2.90 minutes; (Program R1, Column Y). |
| 95 | 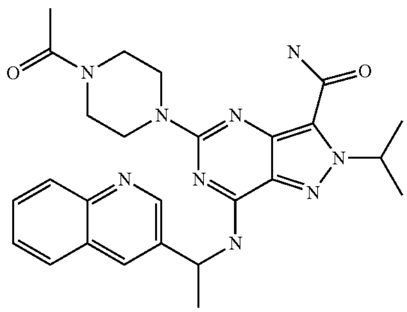 [SMILES: CC(=O)N1CCN(c2nc(NC(C)c3cnc4ccccc4c3)c3nn(C(C)C)c(C(N)=O)c3n2)CC1] | LCMS: m/z = 502.4 [M + H], RT = 2.72 minutes; (Program R1, Column Y). |
| 96 | 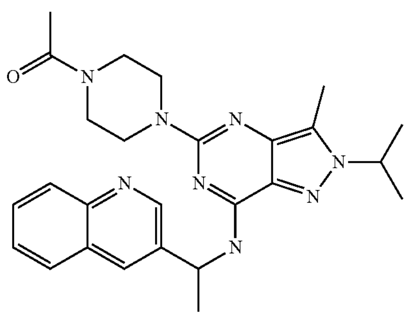 [SMILES: CC(=O)N1CCN(c2nc(NC(C)c3cnc4ccccc4c3)c3nn(C(C)C)c(C)c3n2)CC1] | LCMS: m/z = 473.4 [M + H], RT = 2.47 minutes; (Program R1, Column Y). |
| 97 | 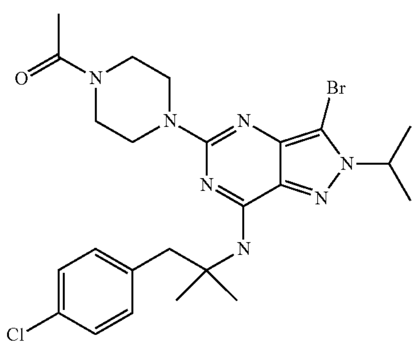 [SMILES: CC(=O)N1CCN(c2nc(NC(C)(C)Cc3ccc(Cl)cc3)c3nn(C(C)C)c(Br)c3n2)CC1] | LCMS: m/z = 548.4 [M+], 550.4 [M + 2], RT = 3.66 minutes; (Program R1, Column Y). |
| 98 | 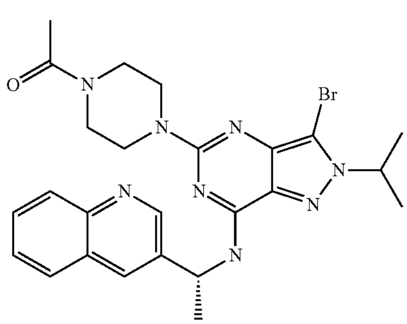 [SMILES: CC(=O)N1CCN(c2nc(N[C@H](C)c3cnc4ccccc4c3)c3nn(C(C)C)c(Br)c3n2)CC1] | LCMS: m/z = 536.8 [M+], 538.8 [M + 2], RT = 2.56 minutes; (Program R1, Column Y). |

TABLE 4-continued

| Example No. | Molecular Structure | LCMS |
|---|---|---|
| 99 | 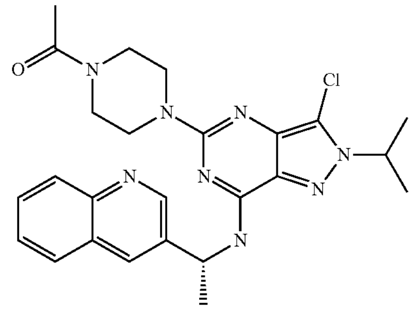 [SMILES: CC(=O)N1CCN(c2nc(N[C@H](C)c3cnc4ccccc4c3)c3nn(C(C)C)c(Cl)c3n2)CC1] | LCMS: m/z = 493.4 [M + H], RT = 3.07 minutes; (Program P1, Column W). |
| 100 | 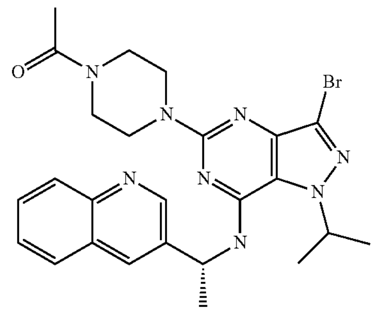 [SMILES: CC(=O)N1CCN(c2nc(N[C@H](C)c3cnc4ccccc4c3)c3c(n2)c(Br)nn3C(C)C)CC1] | LCMS: m/z = 536.8 [M+], 539.0 [M + 2], RT = 2.92 minutes; (Program R1, Column Y). |
| 101 | 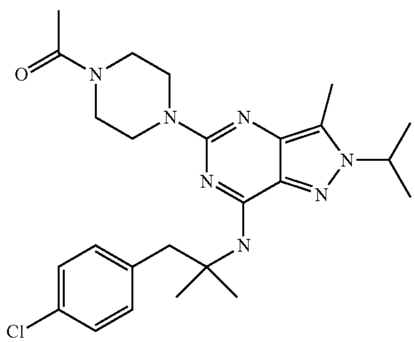 [SMILES: CC(=O)N1CCN(c2nc(NC(C)(C)Cc3ccc(Cl)cc3)c3nn(C(C)C)c(C)c3n2)CC1] | LCMS: m/z = 483.8 [M + H], RT = 2.97 minutes; (Program R1, Column Y). |
| 102 | 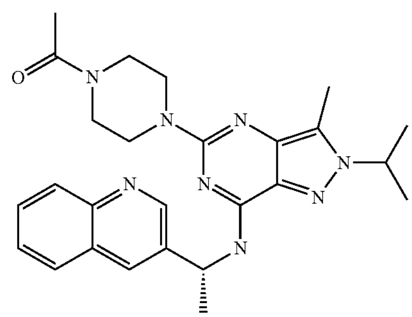 [SMILES: CC(=O)N1CCN(c2nc(N[C@H](C)c3cnc4ccccc4c3)c3nn(C(C)C)c(C)c3n2)CC1] | LCMS: m/z = 473.2 [M + H], RT = 2.45 minutes; (Program R1, Column Y). |
| 103 | 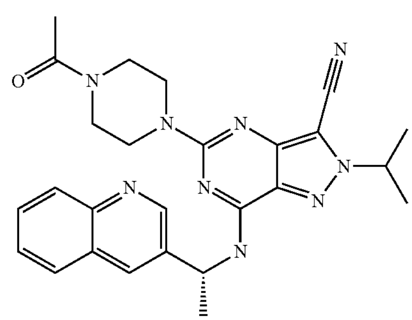 [SMILES: CC(=O)N1CCN(c2nc(N[C@H](C)c3cnc4ccccc4c3)c3nn(C(C)C)c(C#N)c3n2)CC1] | LCMS: m/z = 483.8 [M + H], RT = 2.74 minutes; (Program R1, Column Y). |

TABLE 4-continued
| Example No. | Molecular Structure | LCMS |
|---|---|---|
| 104 | 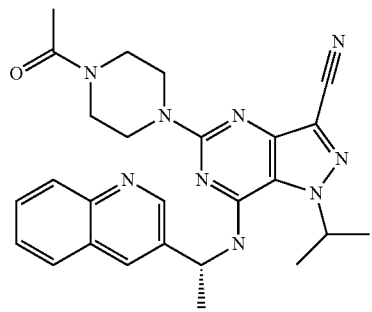 [SMILES: CC(=O)N1CCN(c2nc(N[C@H](C)c3cnc4ccccc4c3)c3c(n2)c(C#N)nn3C(C)C)CC1] | LCMS: m/z = 483.8 [M + H], RT = 2.02 minutes; (Program R1, Column Y). |
| 105 | 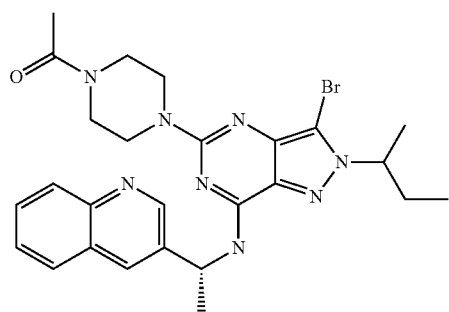 [SMILES: CCC(C)n1nc2c(N[C@H](C)c3cnc4ccccc4c3)nc(N3CCN(C(C)=O)CC3)nc2c1Br] | LCMS: m/z = 550.8 [M+], 552.8 [M + 2], RT = 2.73 minutes; (Program R1, Column Y). |
| 106 | 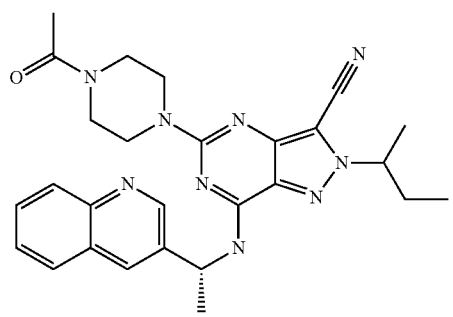 [SMILES: CCC(C)n1nc2c(N[C@H](C)c3cnc4ccccc4c3)nc(N3CCN(C(C)=O)CC3)nc2c1C#N] | LCMS: m/z = 498.2 [M + H], RT = 2.89 minutes; (Program R1, Column Y). |
| 107 | 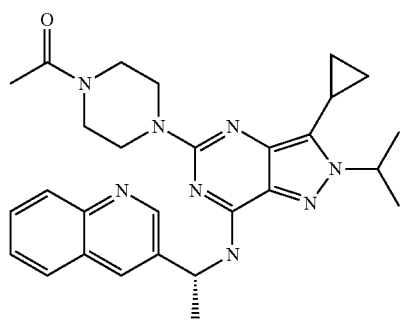 [SMILES: CC(=O)N1CCN(c2nc(N[C@H](C)c3cnc4ccccc4c3)c3nn(C(C)C)c(C4CC4)c3n2)CC1] | LCMS: m/z = 499.2 [M + H], RT = 2.26 minutes; (Program R1, Column V). |

Example 108: Scheme 23 is a Representative Synthesis of 4-{1-sec-Butyl-7-[((R)-cyclopropyl-quinolin-3-yl-methyl)-amino]-1H-pyrazolo[4,3-d]pyrimidin-5-yl}-piperazine-1-sulfonic acid amide) (Xa)

Example 109: Scheme 24 Below is a Representative Synthesis of 4-{1-sec-Butyl-7-[((R)-cyclopropyl-quinolin-3-yl-methyl)-amino]-1H-pyrazolo[4,3-d]pyrimidin-5-yl}-piperazine-1-sulfonic acid amide) (Xa')

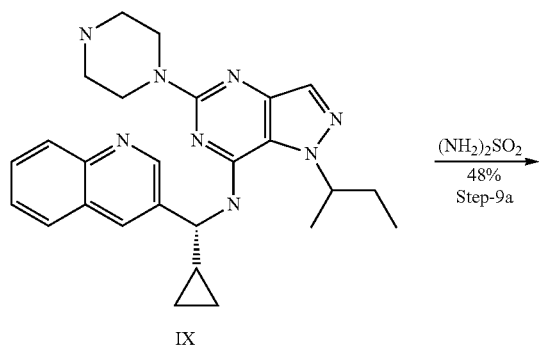

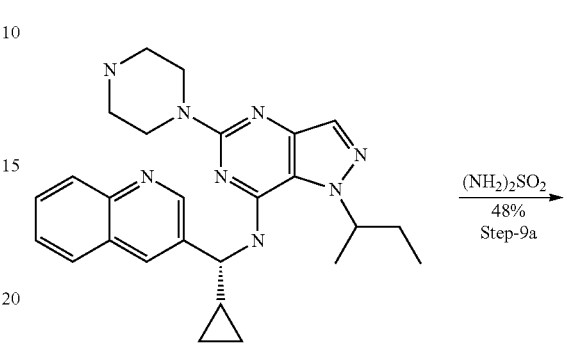

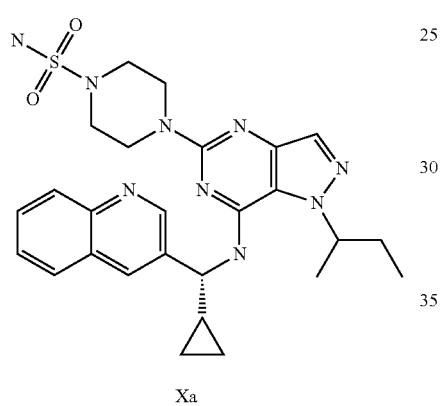

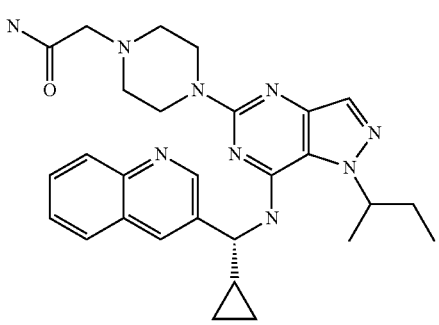

To the solution of compound IX (30 mg, 0.07 mmol, 1 eq) in dioxane (5 mL) was added $(NH_2)_2SO_2$ (25 mg, 0.26 mmol, 3.7 eq) and heated to 100° C. for 14 h. The reaction mixture was cooled to room temperature, quenched by addition of aqueous HCl (1N, 2-3 mL) and concentrated in vacuo. Organic components were extracted with 5% methanol/$CH_2Cl_2$ (50 mL) and the organic layer was dried over anhydrous sodium sulfate and concentrated in vacuo. The crude material was purified by flash chromatography (Combiflash) using 100-200 mesh silica gel eluting with 9% methanol/$CH_2Cl_2$ to obtain compound Xa (18 mg, 48%) as off white solid.

$^1$H NMR (400 MHz, DMSO-$d_6$) δ 9.12-9.10 (m, 1H), 8.45-8.43 (m, 1H), 8.01-7.93 (m, 2H), 7.74-7.70 (m, 2H), 7.61-7.42 (m, 2H), 6.71 (d, J=6 Hz, 2H), 5.19-4.99 (m, 1H), 4.73-4.66 (m, 1H), 3.64-3.40 (m, 4H), 2.95-2.76 (m, 4H), 1.91-1.68 (m, 3H), 1.68-1.51 (m, 3H), 1.35-1.33 (m, 3H), 1.22-0.83 (m, 4H);

LCMS: m/z=536.4 [M+H], RT=2.75 minutes; (Program R1, Column W).

To the solution of compound IX (30 mg, 0.07 mmol, 1 eq) in DMF (3 mL) were added bromoacetamide (18 mg, 0.13 mmol, 2 eq), $K_2CO_3$ (27 mg, 0.20 mmol, 3 eq) and the resulting mixture was heated to 60° C. for 3 h. The reaction mixture was cooled to room temperature, diluted with water and the organic components were extracted with $CH_2Cl_2$ (50 mL). DCM layer was then dried over anhydrous sodium sulfate and concentrated in vacuo. The crude material was purified by flash chromatography (Combiflash) using 100-200 mesh silica gel eluting with 7% methanol/$CH_2Cl_2$ to obtain compound Xa' (25 mg, 75%) as off white solid.

$^1$H NMR (400 MHz, DMSO-$d_6$) δ 9.06-9.04 (m, 1H), 8.37-8.36 (m, 1H), 7.97-7.95 (m, 1H), 7.91-7.88 (m, 1H), 7.68-7.64 (m, 2H), 7.57-7.51 (m, 2H), 7.15-7.07 (2, m H), 5.15-4.91 (m, 1H), 4.75-4.51 (m, 1H), 3.56-3.31 (m, 4H), 2.72-2.63 (m, 2H), 2.22-2.17 (m, 4H), 1.78-1.59 (m, 3H), 1.54-1.47 (m, 3H), 0.82-0.49 (m, 7H);

LCMS: m/z=514.2 [M+H], RT=2.37 minutes; (Program R1, Column X).

Example 110: Scheme 25 Below is a Representative Synthesis of—4-(1-sec-butyl-7-{[(R)-cyclopropyl(quinolin-3-yl)methyl]amino}-1H-pyrazolo[4,3-d]pyrimidin-5-yl)-N'-cyanopiperazine-1-carboximidamide) (XI)

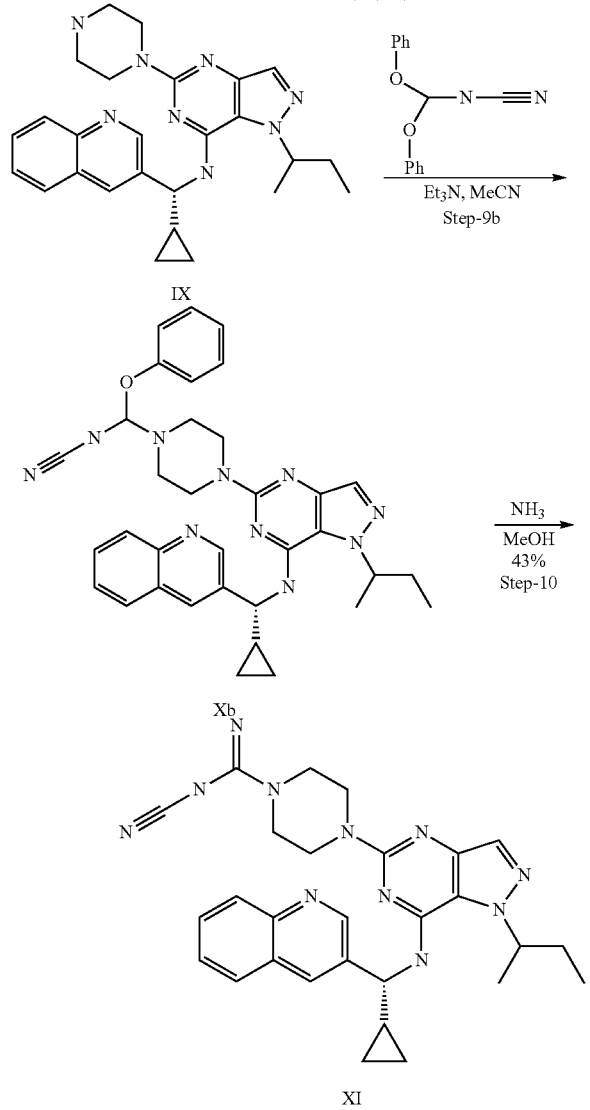

(4-{1-sec-Butyl-7-[((R)-cyclopropyl-quinolin-3-yl-methyl)-amino]-1H-pyrazolo[4,3-d]pyrimidin-5-yl}-piperazin-1-yl)-phenoxy-methyl-cyanamide (Xb)

To a solution of compound IX (50 mg, 0.11 mmol, 1 eq) in MeCN (5 mL) were added diphenylcyanocarbonimidate (32 mg, 0.13 mmol, 1.2 eq) and triethylamine (0.02 mL, 0.13 mmol, 1.2 eq) and the resulting mixture was stirred at 60° C. for 14 h. The reaction mixture was cooled to RT, concentrated in vacuo to obtain compound Xb as light brown sticky solid which was used in the next step without further purification.

LCMS: m/z=601.3 [M+H], RT=3.08 minutes; (Program R1, Column W).

4-(1-sec-butyl-7-{[(R)-cyclopropyl(quinolin-3-yl)methyl]amino}-1H-pyrazolo[4,3-d]pyrimidin-5-yl)-N'-cyanopiperazine-1-carboximidamide (XI)

To a solution of compound Xb (65 mg, 0.11 mmol, 1 eq) in methanol (3 mL) was added $NH_4OH$ (0.4 mL) and the resulting mixture was refluxed for 5 h. The reaction mixture was cooled to RT, concentrated in vacuo. The crude material was purified by flash chromatography (Combiflash) using 100-200 mesh silica gel eluting with 5% methanol/$CH_2Cl_2$ to obtain compound XI (25 mg, 43% for 2 steps) off white solid.

$^1H$ NMR (400 MHz, DMSO-$d_6$) δ 9.11-9.10 (m, 1H), 9.09-8.40 (m, 1H), 8.00-7.93 (m, 2H), 7.73-7.70 (m, 1H), 7.63-7.58 (m, 3H), 7.13-7.12 (m, 2H), 5.11-5.08 (m, 1H), 4.76-4.64 (m, 1H), 3.50-3.33 (m, 8H), 1.91-1.66 (m, 3H), 1.56-1.50 (m, 3H), 0.77-0.50 (m, 7H);

LCMS: m/z=524.6 [M+H], RT=2.72 minutes; (Program R1, Column W).

Example 111: Scheme 25 was Also Used to Synthesize 4-(1-sec-butyl-7-{[(R)-methyl(quinolin-3-yl)methyl]amino}-1H-pyrazolo[4,3-d]pyrimidin-5-yl)-N'-cyanopiperazine-1-carboximidamide (See Table 5 Below)

TABLE 5

| Example No. | Molecular Structure | LCMS |
|---|---|---|
| 111 | 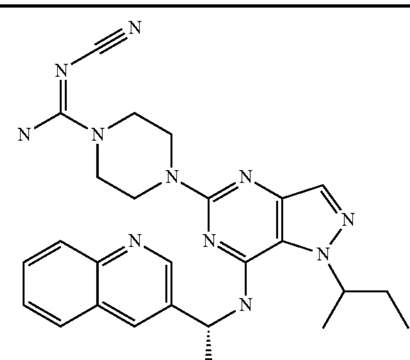 | LCMS: m/z = 498.0 [M + H], RT = 2.47 minutes; (Program R1, Column W). |

Example 112: Scheme 26 Below is a Representative Synthesis of—4-{1-sec-Butyl-7-[((R)-cyclopropyl-quinolin-3-yl-methyl)-amino]-1H-pyrazolo[4,3-d]pyrimidin-5-yl}-piperazine-1-carboxamidine) (XII)

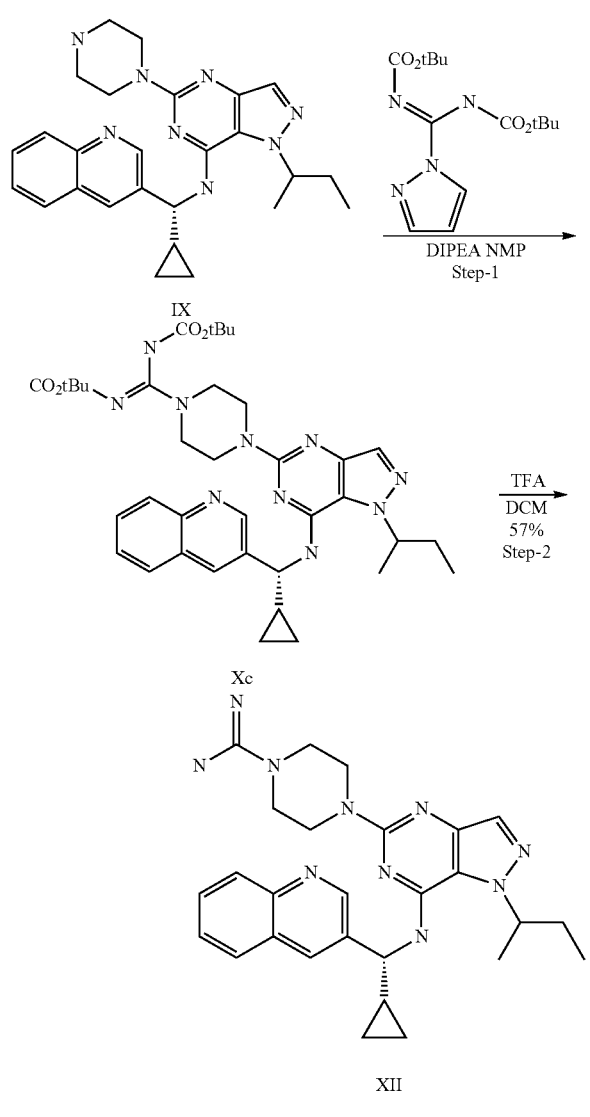

[[(E)-tert-Butoxycarbonylimino]-(4-{1-sec-butyl-7-[((R)-cyclopropyl-quinolin-3-yl-methyl)-amino]-1H-pyrazolo[4,3-d]pyrimidin-5-yl}-piperazin-1-yl)-methyl]-carbamic acid tert-butyl ester (Xc)

To the solution of IX (50 mg, 0.11 mmol, 1 eq) in NMP (5 mL) were added (tert-butoxycarbonylimino-pyrazol-1-yl-methyl)-carbamic acid tert-butyl ester (34 mg, 0.11 mmol, 1 eq) and DIPEA (0.04 mL, 0.22 mmol, 2 eq) and the resulting mixture was stirred at 23° C. for 16 h. The reaction mixture was diluted with water (10 mL) and the organic components were extracted with $CH_2Cl_2$ (50 mL). The organic layer was dried over anhyd. sodium sulfate and concentrated in vacuo. The crude residue was purified by flash chromatography (Combiflash) using 100-200 mesh silica gel eluting with 2% $MeOH/CH_2Cl_2$ to obtain compound Xc (100 mg) as brown solid.

LCMS: m/z=699.6 [M+H], RT=3.22 minutes; (Program R1, Column W).

4-{1-sec-Butyl-7-[((R)-cyclopropyl-quinolin-3-yl-methyl)-amino]-1H-pyrazolo[4,3-d]pyrimidin-5-yl}-piperazine-1-carboxamidine (XII)

To a solution of compound Xc (100 mg, 0.14 mmol, 1 eq) in $CH_2Cl_2$ (10 mL) was added TFA (0.11 mL, 1.43 mmol, 10 eq) under ice-cold condition and the resulting mixture was stirred at 23° C. for 5 h. The reaction mixture was concentrated in vacuo. The residue was diluted with toluene (3 mL) and further concentrated in vacuo. The residue was diluted with aq. $NaHCO_3$ solution [5 mL] and the organic components were extracted with 5% $MeOH/CH_2Cl_2$ (50 ml). The organic layer was concentrated in vacuo to obtain compound XII (40 mg, 57%) as yellow solid (XII).

$^1$H NMR (400 MHz, DMSO-$d_6$) δ 9.10-9.08 (m, 1H), 8.42-8.40 (m, 1H), 8.01-7.93 (m, 2H), 7.74-7.71 (m, 2H), 7.65-7.60 (m, 2H), 7.40-7.20 (m, 3H), 5.09-5.08 (m, 1H), 4.80-4.73 (m, 1H), 3.60-3.32 (m, 8H), 1.90-1.60 (m, 3H), 1.57-1.50 (m, 3H), 0.77-0.57 (m, 7H);

LCMS: m/z=499.3 [M+H], RT=2.10 minutes; (Program R1, Column W).

Example 113

Scheme 27 below is a representative synthesis of 2-{4-[1-sec-Butyl-7-((R)-1-quinolin-3-yl-ethylamino)-1H-pyrazolo[4,3-d]pyrimidin-5-yl]-pyrazol-1-yl}-ethanol.

Intermediate VIIa was synthesized in a similar manner to that of VII.

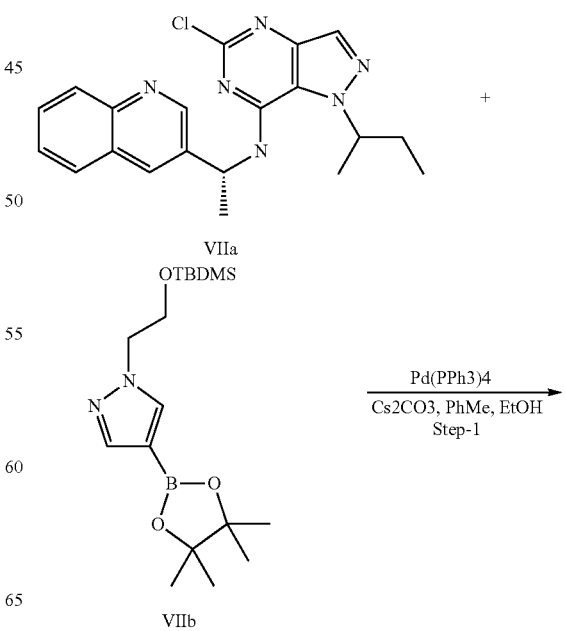

121
-continued

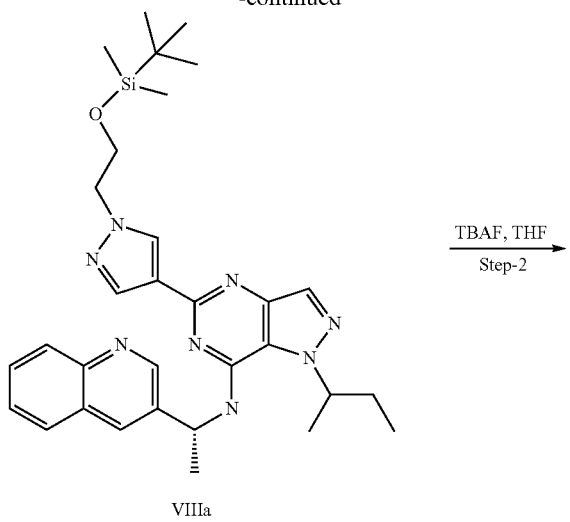

VIIIa

TBAF, THF
Step-2
→

122

(1-sec-Butyl-5-{1-[2-(tert-butyl-dimethyl-silany-loxy)-ethyl]-1H-pyrazol-4-yl}-1H-pyrazolo[4,3-d]pyrimidin-7-yl)-((R)-1-quinolin-3-yl-ethyl)-amine (VIIIa)

To a stirred and degassed [with Ar] solution of VIIa, as prepared in Scheme 22 (200 mg, 0.53 mmol, 1 eq) in a mixture of toluene (14 ml) and EtOH (6 ml) was added $Cs_2CO_3$ (513 mg, 1.58 mmol, 3 eq), compound VIIb (278 mg, 0.79 mmol, 1.5 eq) and the mixture was again degassed with Ar for 15 min. To the reaction mixture was added $Pd(PPh_3)_4$ (32 mg, 0.05 mmol, 0.1 eq) and the resulting mixture was stirred at 90° C., under Ar atmosphere for 16 h. The reaction mixture was cooled to RT, filtered through Celite and the filtrate was concentrated under reduced pressure to obtain crude product VIIIa (300 mg) as off white solid. This was used for the next step without further purification.

2-{4-[1-sec-Butyl-7-((R)-1-quinolin-3-yl-ethyl-amino)-1H-pyrazolo[4,3-d]pyrimidin-5-yl]-pyrazol-1-yl}-ethanol To a stirred solution of VIIIa (300 mg, 0.53 mmol, 1 eq) in THF (15 ml) was added TBAF (1 ml, 1M in THF) and the reaction mixture was stirred at 23° C. for 2 h. The reaction mixture was concentrated under reduced pressure to obtain crude product which was purified by flash chromatography (Combiflash) using 100-200 mesh silica gel eluting with 10% MeOH/$CH_2Cl_2$ to obtain compound CE01111 (20 mg) as off white solid.

LCMS: m/z=457.4 [M+H], RT=3.21 minutes; (Program R1, Column W).

Examples 114-123

The 10 compounds shown in Table 6 below were synthesized using the Scheme 27.

| Example No. | Molecular Structure | LCMS |
|---|---|---|
| 114 | (structure) | LCMS: m/z = 453.4 [M + H], RT = 2.98 minutes; (Program R1, Column W). |
| 115 | (structure) | LCMS: m/z = 467.4 [M + H], RT = 3.41 minutes; (Program R1, Column W). |

-continued
| Example No. | Molecular Structure | LCMS |
|---|---|---|
| 116 | 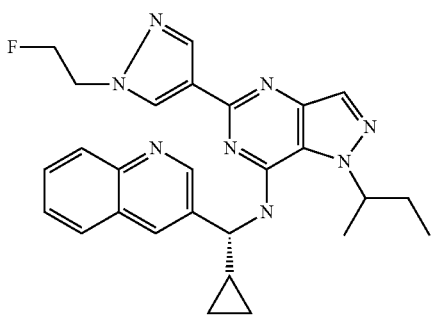 [SMILES: CCC(C)n1ncc2nc(-c3cnn(CCF)c3)nc(N[C@@H](c3cnc4ccccc4c3)C3CC3)c21] | LCMS: m/z = 485.2 [M + H], RT = 3.47 minutes; (Program R1, Column W). |
| 117 | 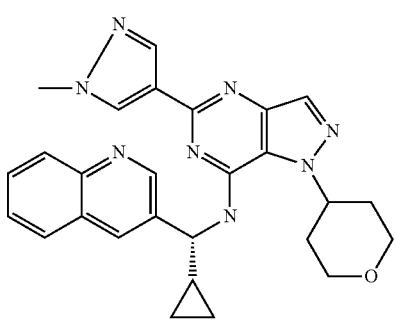 [SMILES: Cn1cc(-c2nc(N[C@@H](c3cnc4ccccc4c3)C3CC3)c3c(cnn3C3CCOCC3)n2)cn1] | LCMS: m/z = 481.2 [M + H], RT = 2.86 minutes; (Program P1, Column V). |
| 118 | 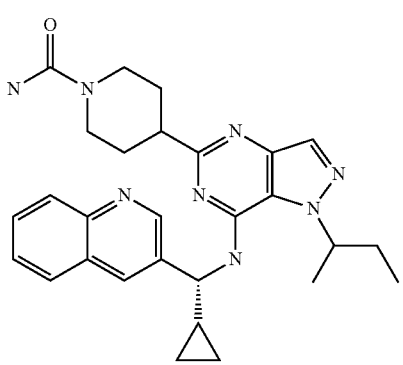 | LCMS: m/z = 499.2 [M + H], RT = 3.00 minutes; (Program R1, Column W). |
| 119 | 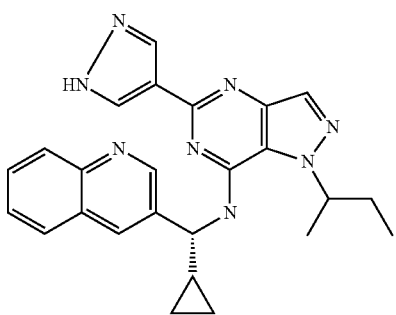 [SMILES: CCC(C)n1ncc2nc(-c3cn[nH]c3)nc(N[C@@H](c3cnc4ccccc4c3)C3CC3)c21] | LCMS: m/z = 439.2 [M + H], RT = 3.37 minutes; (Program R1, Column W). |

-continued

| Example No. | Molecular Structure | LCMS |
|---|---|---|
| 120 | 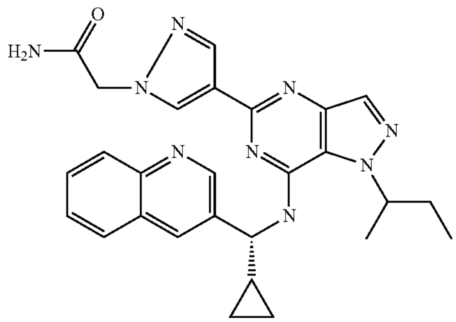 [SMILES: CCC(C)n1ncc2nc(-c3cnn(CC(N)=O)c3)nc(N[C@@H](c3cnc4ccccc4c3)C3CC3)c21] | LCMS: m/z = 496.0 [M + H], RT = 3.44 minutes; (Program R1, Column W). |
| 121 | 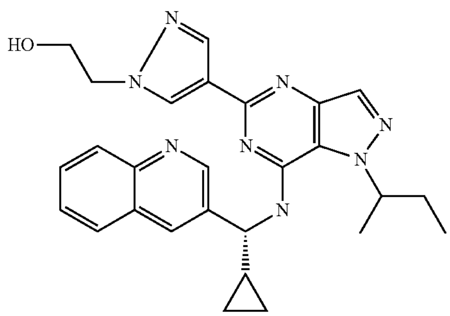 [SMILES: CCC(C)n1ncc2nc(-c3cnn(CCO)c3)nc(N[C@@H](c3cnc4ccccc4c3)C3CC3)c21] | LCMS: m/z = 483.2 [M + H], RT = 3.28 minutes; (Program R1, Column W). |
| 122 | 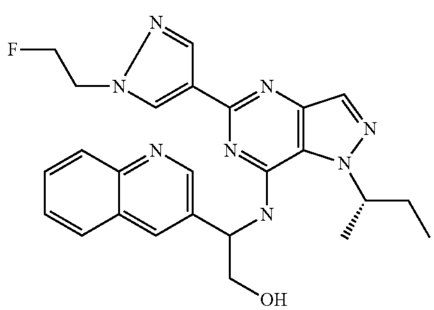 [SMILES: CC[C@H](C)n1ncc2nc(-c3cnn(CCF)c3)nc(NC(CO)c3cnc4ccccc4c3)c21] | LCMS: m/z = 475.2 [M + H], RT = 3.33 minutes; (Program R1, Column W). |
| 123 | 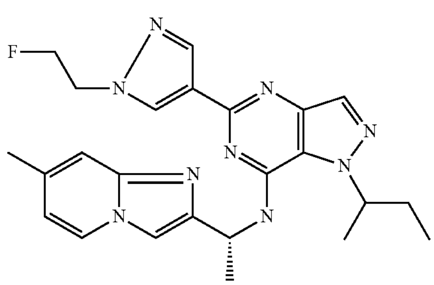 [SMILES: CCC(C)n1ncc2nc(-c3cnn(CCF)c3)nc(N[C@H](C)c3cn4ccc(C)cc4n3)c21] | LCMS: m/z = 462.2 [M + H], RT = 2.84 minutes; (Program R1, Column W). |

The compound of Example 118 was synthesized via the Suzuki reaction of VIIa as shown in Scheme 27 with 4-(4,4,5,5-Tetramethyl-[1,3,2]dioxaborolan-2-yl)-3,6-dihydro-2H-pyridine-1-carboxylic acid tert-butyl ester, followed by further reactions as steps 8 and 9 as shown in Scheme 21, with the final double bond reduction carried out by hydrogenation with 10% Pd/C in EtOH.

Example 124: Scheme 28 Below is a Representative Synthesis of 1-sec-Butyl-7-[((R)-cyclopropyl-quinolin-3-yl-methyl)-amino]-1H-pyrazolo[4,3-d]pyrimidine-5-carboxylic acid cyclopropylamide

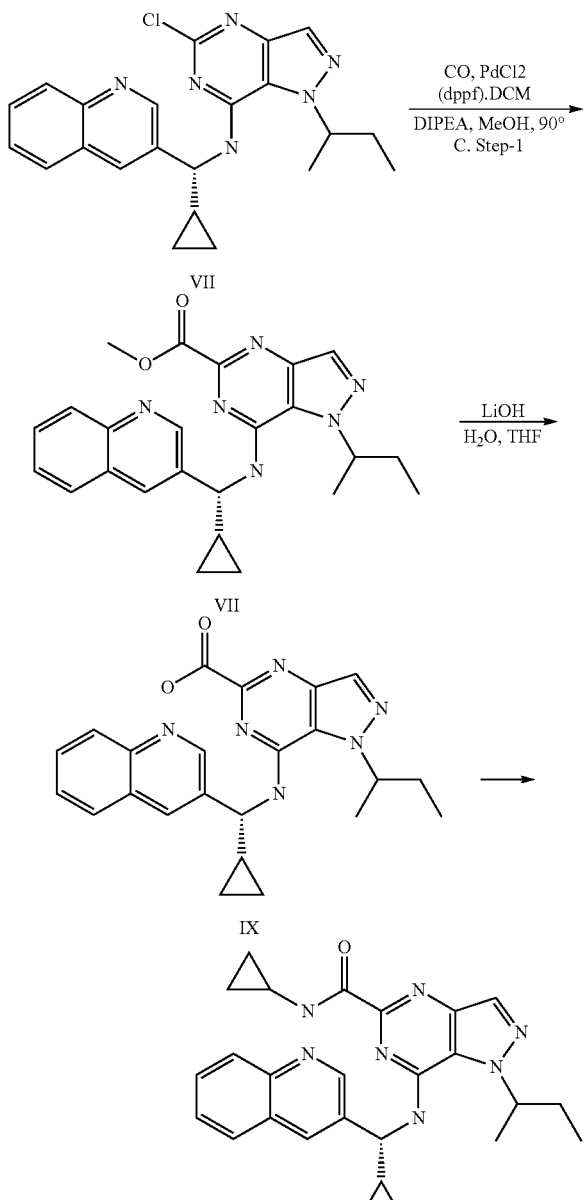

1-sec-Butyl-7-[((R)-cyclopropyl-quinolin-3-yl-methyl)-amino]-1H-pyrazolo[4,3-d]pyrimidine-5-carboxylic acid methyl ester (VIII)

To a stirred solution of VII as prepared in Scheme 21 (500 mg, 1.23 mmol, 1 eq) in MeOH (2 ml) were added PdCl$_2$(dppf).DCM (100 mg, 0.123 mmol, 0.1 eq) and DIPEA (1.1 ml, 6.16 mmol, 5 eq) and the mixture was degassed with Ar for 15 min. the resulting mixture was subjected to reaction in Parr autoclave under 50 psi CO pressure at 90° C. for 16 h. The reaction mixture was cooled to RT, filtered through Celite and the filtrate was concentrated under reduced pressure to obtain crude product which was purified by flash chromatography (Combiflash) using 100-200 mesh silica gel eluting with 65% EtOAc/hexane to obtain compound VIII (440 mg, 84%).

$^1$H NMR (400 MHz, DMSO-d$_6$) δ 9.18-9.13 (m, 1H), 8.53-8.50 (m, 1H), 8.25 (m, 1H), 8.06-7.94 (m, 3H), 7.74-7.70 (m, 1H), 7.62-7.55 (m, 1H), 5.20 (m, 1H), 4.95-4.80 (m, 1H), 3.82-3.81 (m, 3H), 1.98-1.80 (m, 3H), 1.60-1.55 (m, 3H), 0.75-0.50 (m, 7H);

LCMS: m/z=431.2 [M+H], RT=3.78 minutes; (Program R1, Column W).

1-sec-Butyl-7-[((R)-cyclopropyl-quinolin-3-yl-methyl)-amino]-1H-pyrazolo[4,3-d]pyrimidine-5-carboxylic acid (IX)

To a stirred solution of VIII (440 mg, 1.023 mmol, 1 eq) in THF (8 ml) and water (4 ml) was added LiOH.H$_2$O (86 mg, 2.05 mmol, 2 eq) and the mixture was stirred at 23° C. for 4 h. The reaction mixture was concentrated under reduced pressure and diluted with water. The aqueous layer was acidified with dilute HCl and the organic components were extracted into MeOH/CH$_2$Cl$_2$ to obtain compound IX (370 mg, crude), which was used for the next step without further purification.

$^1$H NMR (400 MHz, DMSO-d$_6$) δ 9.30-9.25 (m, 1H), 8.78-8.72 (m, 1H), 8.25 (s, 1H), 8.12-8.00 (m, 3H), 7.81 (m, 1H), 8.70 (m, 1H), 5.21 (m, 1H), 5.01-4.92 (m, 1H), 2.00-1.70 (m, 3H), 1.60-1.54 (m, 3H), 0.80-0.50 (m, 7H);

LCMS: m/z=417.2 [M+H], RT=3.29 minutes; (Program R1, Column W).

1-sec-Butyl-7-[((R)-cyclopropyl-quinolin-3-yl-methyl)-amino]-1H-pyrazolo[4,3-d]pyrimidine-5-carboxylic acid cyclopropylamide To a stirred solution of IX (50 mg, 0.12 mmol, 1 eq) in DMF (3 ml) were added cyclopropyl amine (8 mg, 0.144 mmol, 1.2 eq) DIPEA (23 mg, 0.18 mmol, 1.5 eq) and 1-[Bis(dimethylamino)methylene]-1H-1,2,3-triazolo [4,5-b] pyridinium 3-oxid hexafluorophosphate (HATU) (59 mg, 0.16 mmol, 1.3 eq) and stirred at 23° C. for 5 h. The reaction mixture was diluted with water and the organic components were extracted with CH$_2$Cl$_2$ to obtain crude product, which was purified by flash chromatography (Combiflash) using 100-200 mesh silica gel eluting with 45% MeOH/CH$_2$Cl$_2$ to obtain compound 1-sec-Butyl-7-[((R)-cyclopropyl-quinolin-3-yl-methyl)-amino]-1H-pyrazolo[4,3-d]pyrimidine-5-carboxylic acid cyclopropylamide (440 mg, 84%).

$^1$H NMR (400 MHz, DMSO-d$_6$) δ 9.17-9.16 (m, 1H), 8.50-8.49 (m, 1H), 8.21-8.20 (m, 1H), 8.19-8.12 (m, 1H), 8.01-7.90 (m, 3H), 7.74-7.68 (m, 1H), 7.62-7.57 (m, 1H), 5.30-5.20 (m, 1H), 5.05-4.90 (m, 1H), 2.80-2.70 (m, 1H), 2.00-1.90 (m, 3H), 1.63-1.55 (m, 3H), 1.25 (m, 1H), 0.80-0.45 (m, 10H);

LCMS: m/z=456.4 [M+H], RT=4.13 minutes; (Program R1, Column W).

Example 125: Scheme 29 is a Representative Synthesis of [1-sec-Butyl-5-(5-methyl-[1,3,4]oxadiazol-2-yl)-1H-pyrazolo[4,3-d]pyrimidin-7-yl]-((R)-cyclopropyl-quinolin-3-yl-methyl)-amine

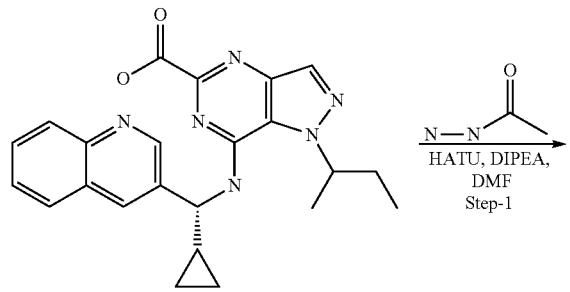

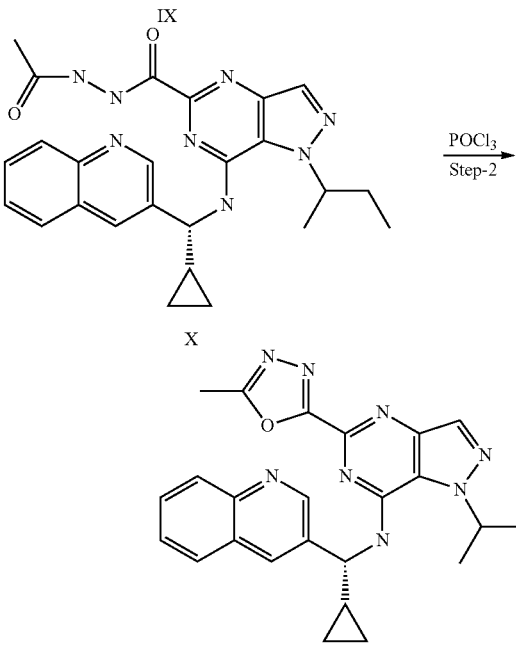

1-sec-Butyl-7-[((R)-cyclopropyl-quinolin-3-yl-methyl)-amino]-1H-pyrazolo[4,3-d]pyrimidine-5-carboxylic acid N'-acetyl-hydrazide (X)

To a stirred solution of IX as prepared in Scheme 28 (160 mg, 0.38 mmol, 1 eq) in DMF (8 ml) was added acetic acid hydrazide (34 mg, 0.46 mmol, 1.2 eq) DIPEA (73 mg, 0.58 mmol, 1.5 eq) and HATU (190 mg, 0.50 mmol, 1.3 eq) and stirred at 23° C. for 16 h. The reaction mixture was diluted with water and the organic components were extracted with $CH_2Cl_2$ to obtain crude product which was purified by flash chromatography (Combiflash) using 100-200 mesh silica gel eluting with 8% MeOH/$CH_2Cl_2$ to obtain compound X (180 mg, 99%).

LCMS: m/z=473.0 [M+H], RT=3.34 minutes; (Program R1, Column W).

[1-sec-Butyl-5-(5-methyl-[1,3,4]oxadiazol-2-yl)-1H-pyrazolo[4,3-d]pyrimidin-7-yl]-((R)-cyclopropyl-quinolin-3-yl-methyl)-amine Compound IX (180 mg, 0.38 mmol, 1 eq) was taken in $POCl_3$ (3 ml) and refluxed for 3 h. The reaction mixture was then cooled to RT, quenched with aq. $NaHCO_3$ and the organic components were extracted with $CH_2Cl_2$ to obtain crude product which was purified by flash chromatography (Combiflash) using 100-200 mesh silica gel eluting with 2% MeOH/$CH_2Cl_2$ followed by prep TLC (60% EtOAc/hexane) to obtain compound CE01108 (15 mg, 9%).

$^1$H NMR (400 MHz, DMSO-$d_6$) δ 9.22-9.18 (m, 1H), 8.61-8.58 (m, 1H), 8.28-8.27 (m, 1H), 8.18-8.15 (m, 1H), 8.00-7.93 (m, 2H), 7.74-7.69 (m, 1H), 7.61-7.57 (m, 1H), 5.28 (m, 1H), 4.90-4.80 (m, 1H), 2.59 (m, 2H), 2.00-1.80 (m, 3H), 1.62-1.56 (m, 3H), 0.76-0.56 (m, 6H);

LCMS: m/z=455.3 [M+H], RT=3.07 minutes; (Program P1, Column V).

Example 126: Scheme 30 is a Representative Synthesis of 1-{1-sec-Butyl-7-[((R)-cyclopropyl-quinolin-3-yl-methyl)-amino]-1H-pyrazolo[4,3-d]pyrimidin-5-yl}-1H-[1,2,3]triazole-4-carboxylic acid amide

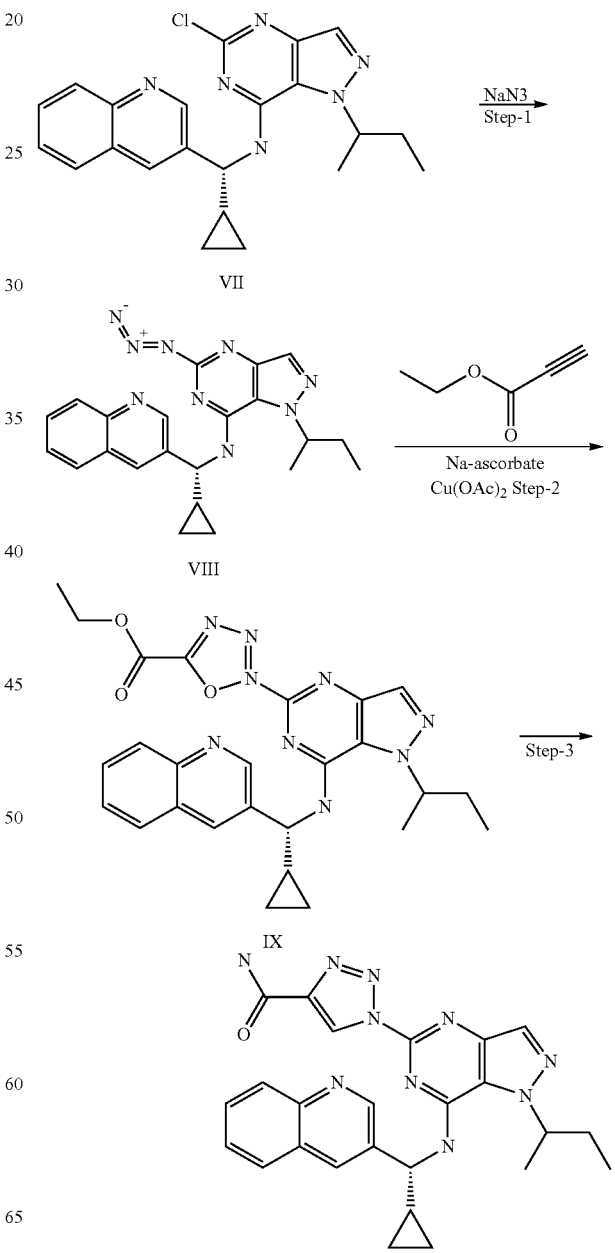

(5-Azido-1-sec-butyl-1H-pyrazolo[4,3-d]pyrimidin-7-yl)-((R)-cyclopropyl-quinolin-3-yl-methyl)-amine (VIII)

To a stirred solution of VII as prepared in Scheme 21 (100 mg, 0.25 mmol, 1 eq) in DMF (2 ml) in a sealed tube were added $K_2CO_3$ (68 mg, 0.49 mmol, 2 eq) and $NaN_3$ (32 mg, 0.49 mmol, 2 eq) and stirred at 160° C. for 2 days. The reaction mixture was cooled to RT, diluted with water and the organic components were extracted with EtOAc to obtain crude product which was purified by flash chromatography (Combiflash) using 100-200 mesh silica gel eluting with 70% EtOAc/hexane to obtain compound VIII (80 mg, 79%).

LCMS: m/z=414.2 [M+H], RT=3.80 minutes; (Program P1, Column V).

1-{1-sec-Butyl-7-[((R)-cyclopropyl-quinolin-3-yl-methyl)-amino]-1H-pyrazolo[4,3-d]pyrimidin-5-yl}-1H-[1,2,3]triazole-4-carboxylic acid ethyl ester (IX)

To a stirred solution of VIII (80 mg, 0.19 mmol, 1 eq) in MeOH (5 ml) were added a solution of sodium ascorbate (4 mg, 0.019 mmol, 0.1 eq, dissolved in 0.3 ml water), $Cu(OAc)_2 \cdot H_2O$ (4 mg, 0.019 mmol, 0.1 eq) and ethyl propiolate (0.06 ml, 0.58 mmol, 3 eq) and the resulting mixture was stirred at 23° C. for 16 h. The reaction mixture was concentrated in vacuo and purified by flash chromatography (Combiflash) using 100-200 mesh silica gel eluting with 84% EtOAc/hexane to obtain compound IX (30 mg, 30%).

LCMS: m/z=512.2 [M+H], RT=4.32 minutes; (Program P1, Column V).

1-{1-sec-Butyl-7-[((R)-cyclopropyl-quinolin-3-yl-methyl)-amino]-1H-pyrazolo[4,3-d]pyrimidin-5-yl}-1H-[1,2,3]triazole-4-carboxylic acid amide To a stirred solution of IX (30 mg, 0.058 mmol, 1 eq) in MeOH (3 ml) in a sealed tube was added aqueous ammonium hydroxide (2 ml) and the mixture was stirred at 23° C. for 16 h. The reaction mixture was concentrated in vacuo and purified by prep TLCl eluting with 70% EtOAc/hexane to obtain compound CE01091 (7 mg, 24%).

$^1$H NMR (400 MHz, DMSO-d$_6$) δ 9.22-9.18 (m, 1H), 9.13-9.09 (m, 1H), 8.60-8.56 (m, 1H), 8.38-8.34 (m, 1H), 8.25-8.24 (m, 1H), 8.03-7.92 (m, 3H), 7.73-7.69 (m, 1H), 7.61-7.58 (m, 2H), 5.26 (m, 1H), 5.14-5.03 (m, 1H), 2.00-1.70 (m, 43H), 1.63-1.57 (m, 3H), 0.79-0.57 (m, 6H);

LCMS: m/z=483.2 [M+H], RT=2.93 minutes; (Program P1, Column V).

Example 127: Scheme 31 is a Representative Synthesis of (1-sec-Butyl-5-pyridazin-3-yl-1H-pyrazolo[4,3-d]pyrimidin-7-yl)-((R)-cyclopropyl-quinolin-3-yl-methyl)-amine

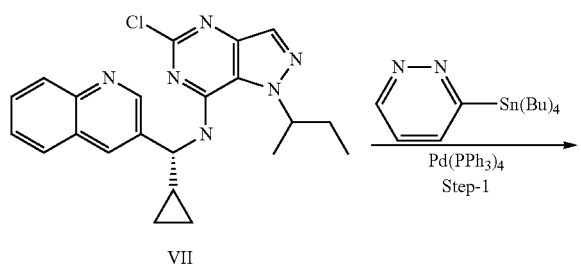

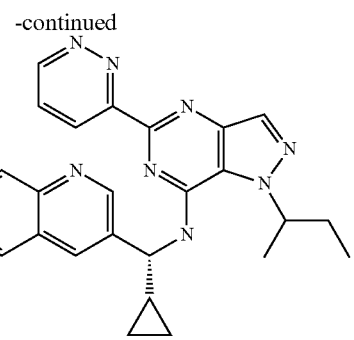

(1-sec-Butyl-5-pyridazin-3-yl-1H-pyrazolo[4,3-d]pyrimidin-7-yl)-((R)-cyclopropyl-quinolin-3-yl-methyl)-amine To a stirred solution of VII prepared in Scheme 21 [for CE00976] (100 mg, 0.25 mmol, 1 eq) in DMF (5 ml) in a sealed tube was added 3-(tributyltin)pyridazine (182 mg, 0.49 mmol, 2 eq) and the mixture was degassed with Ar for 30 min. To this reaction mixture was added $Pd(PPh_3)_4$ (30 mg, 0.025 mmol, 0.1 eq) and degassing was repeated with Ar for another 10 min. The reaction mixture was then heated at 120° C. for 18 h. The reaction mixture was cooled to RT, filtered through Celite and the filtrate was concentrated under reduced pressure to obtain crude product which was purified by flash chromatography (Combiflash) using 100-200 mesh silica gel eluting with 70% EtOAc/hexane to obtain compound CE01099 (40 mg, 36%).

$^1$H NMR (400 MHz, DMSO-d$_6$) δ 9.90-9.86 (m, 1H), 9.32-9.28 (m, 1H), 9.26-9.22 (m, 1H), 8.58 (m, 1H), 8.32-8.28 (m, 2H), 8.15-8.09 (m, 1H), 8.00-7.94 (m, 2H), 7.75-7.65 (m, 1H), 7.60-7.55 (m, 1H), 5.28 (m, 1H), 5.16-5.05 (m, 1H), 2.00-1.70 (m, 3H), 1.67-1.58 (m, 3H), 0.79-0.69 (m, 6H);

LCMS: m/z=451.6 [M+H], RT=3.98 minutes; (Program R1, Column W).

Example 128: In Vitro Studies

A. Cloning

The FLIPR® assay utilizes cells which express human or rat P2X3 or P2X2/3 receptors. Recombinant cells expressing hP2X3 (Cat #6188) and hP2X2/3 (Cat #6179) were procured from Chantest Corp. Rat P2X2 (NCBI Accession No: U14414) was amplified by PCR from PC12 cDNA (a rat adrenal medulla cell line). The PCR product obtained containing the protein coding sequence of rat P2X2 was cloned into EcoRV—digested and dephosphorylated vector pIRES-puro3 within the multiple cloning site (MCS). See, FIG. 1A.

Figure 1B:
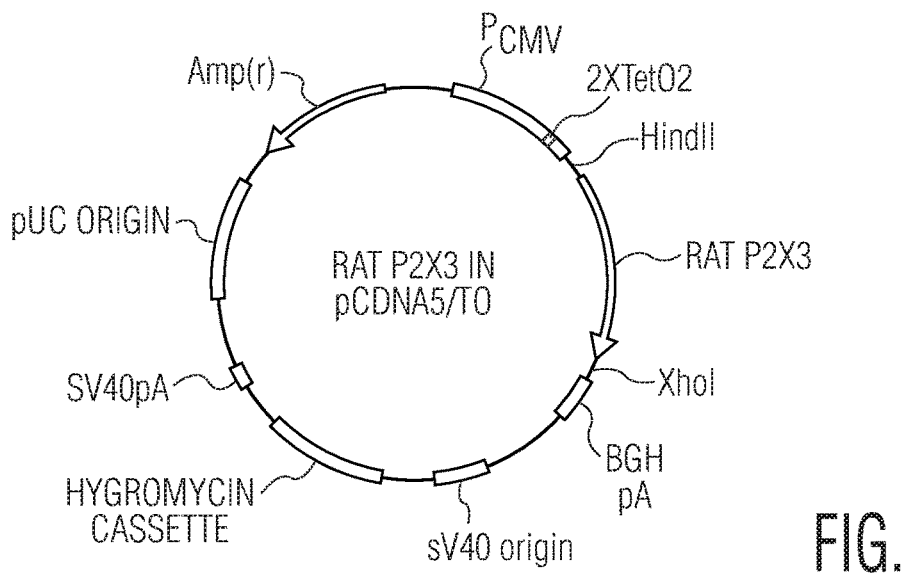
FIG. 1B is a map of a circular plasmid pCDNA-Hygro (Invitrogen) into which the coding sequence of rat P2X3 (NCBI Accession No: X91167), amplified by PCR from rat brain cDNA, has been cloned. The PCR product obtained containing the protein coding sequence of rat P2X3 was cloned into EcoRV-digested and dephosphorylated vector pCDNA-Hygro within the multiple cloning site (MCS).
Figure 1C:
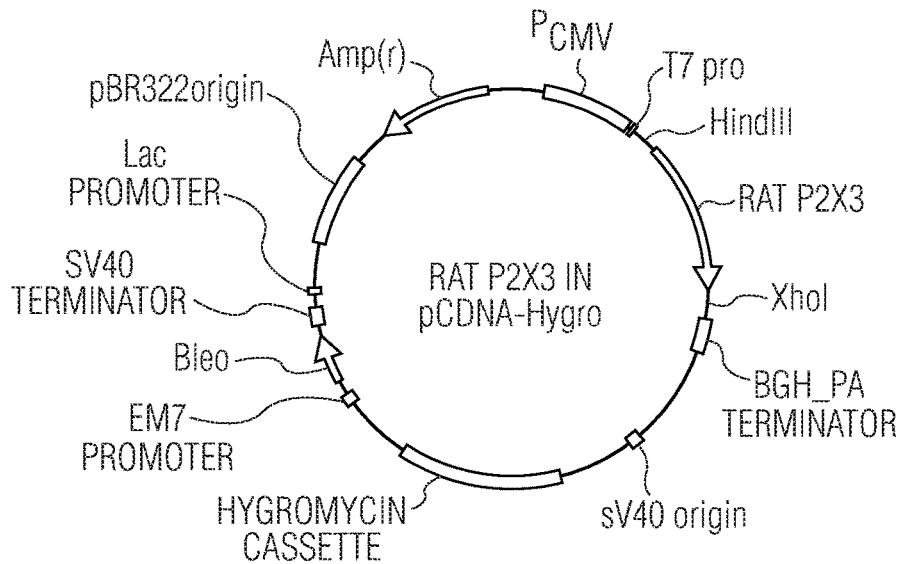
FIG. 1C is a vector generated from the pcDNA-Hygro containing the rat P2X3, which was then subcloned into pcDNA-5/TO (Invitrogen/Life Technologies) at HindIII (5') and XhoI (3') sites within the multiple cloning site (MCS) of the vector.

Rat P2X3 (NCBI Accession No: X91167) was amplified by PCR from rat brain cDNA. The PCR product obtained containing the protein coding sequence of rat P2X3 was cloned into EcoRV—digested and dephosphorylated vector pCDNA-Hygro within the multiple cloning site (MCS) (FIG. 1B). Rat P2X3 cloned into pcDNA-Hygro was then subcloned into pcDNA-5/TO at HindIII (5') and XhoI (3') sites within the multiple cloning site (MCS) of the vector (FIG. 1C).

All the constructs yielding the recombinant vector DNA were used for transfection and generation of the cell lines, after sequence verification.

B. Development of Recombinant TRex293 Cells Expressing rP2X2/3 and CHO-TRex Cells Expressing rP2X3

Transfection was carried out using super-coiled constructs (purified using QIAGEN kit) in antibiotic free, serum free DMEM using Lipofectamine® 2000 (Invitrogen) transfection agent. The DNA constructs rat P2X2 in pIRES-Puro3 and rat P2X3 in pCDNA5/TO were co-transfected into TRex293 cells in order to generate the rP2X2/3 stable line. 50 µg/mL hygromycin (Invitrogen) and 0.5 µg/mL puromycin (Fermentek) were used for selection of stable clones of rP2X2/3. Rat P2X3 in pCDNA5/TO DNA construct was transfected to CHO-TRex cells to generate the rP2X3 stable line and 500 µg/mL hygromycin (Invitrogen) was used as selection antibiotic. Transfected stable colonies were then functionally verified and robust clones suitable for assay were clonally purified through dilutions.

C. Assay Protocols (i) Intracellular Calcium Assay Protocol for Screening Compounds Cryo-vial containing $6 \times 10^6$ cells (human P2X3-HEK/human P2X2/3-TRex293/rat P2X2/3-TRex293/rat P2X3 TRex-CHO) was thawed in a 37° C. water bath. Cells were suspended in 20 mL of respective cell plating media (See annexure for composition) in a 50 mL centrifuge tube. The cell viability was checked with the help of Trypan Blue dye. Upon washing, cells were plated in a black 384-well clear bottomed, sterile poly-D-lysine coated plate such that, each well contained 10,000 cells (15,000/well for hP2X3) in 30 µL cell plating media. The plate was incubated in a 5% $CO_2$ incubator at 37° C. for 24 h.

The next day, prior to the assay, the cell plating media was removed from each well by decanting and gentle tapping. Thirty µL of FLIPR Calcium 4 dye solution was added to each well. The plate was incubated at 37° C. for 45 min (60 min for hP2X3). The plate was next equilibrated at room temperature for 15 minutes before placing it in a 384 well FLIPR for the assay.

Compounds were dissolved in DMSO and serially diluted following 11 point half log (3.16 fold) dilution with a starting concentration of 2 mM. Dilutions were mixed with assay buffer just before performing the assay.

Compounds were added to the respective wells of the assay-ready cell plate with the help of the FLIPR and fluorescence readings were captured for 5 min to observe any possible agonistic property of the compounds. The plate was then incubated at room temperature for 15 min. The cells were stimulated with respective agonist $EC_{75}$ concentration and the fluorescence readings were captured for another 5 min by FLIPR. The difference in fluorescence readings in presence of the compounds were compared with that of the control wells (wells having no compound) to calculate the inhibitory potency of the compounds. The $IC_{50}$ values of the compounds were determined using the Graph pad Prism software.

(ii) Cell Plating Media for hP$_2$X$_3$-HEK and hP$_2$X$_{2/3}$-TRex293 Cells

DMEM/F12(1:1) HAM media (Invitrogen; Cat #11039)
1×NEAA (Invitrogen; Cat #11140)
25 mM HEPES (Invitrogen; Cat #15630)
1 mM sodium pyruvate (Invitrogen; Cat #11360)
10% tetracycline negative FBS (PAA; Cat # A15-209)
1 µg/mL doxycycline (Clontech; Cat #63131) [for hP2X2/3-TRex293 cells only]

(iii) Cell Plating Media for rP$_2$X$_{2/3}$-TRex293 Cells
DMEM media (Invitrogen; Cat #11965)
25 mM HEPES (Invitrogen; Cat #15630)
10% tetracycline negative FBS (PAA; Cat # A15-209)
1 µg/mL Doxycycline (Clontech; Cat #63131)

(iv) Cell Plating Media for rP$_2$X$_3$-CHOTRex Cells
F-12 nutrient mixture (HAM) 1× (Invitrogen; Cat #11765)
1× Glutamax™ (Invitrogen; Cat #35050)

10% tetracycline negative FBS (PAA; Cat # A15-209)
1 µg/mL doxycycline (Clontech; Cat #63131)

(v) Assay Buffer Composition
HBSS (Invitrogen Cat #14025)
20 mM HEPES (Invitrogen Cat #15630)
0.01% F127 (Sigma Cat # P2443)
1.8 mM $CaCl_2$ (Sigma Cat # C5080)
pH adjusted to 7.4

(vi) Dye Solution Composition
1×FLIPR Calcium 4 dye in assay buffer (Molecular devices Cat # R8141)
1.8 mM Probenecid (Sigma Cat # P8761)
pH adjusted to 7.4

Data from the $P2X_3$ and $P2X_{2/3}$ FLIPR assays for compounds of formula (I) are shown in Table 7 below.

TABLE 7

| Example | hP2X$_3$ | hP2X$_{2/3}$ |
|---|---|---|
| 1 | A | D |
| 2 | B | |
| 3 | B | C |
| 4 | A | D |
| 5 | A | D |
| 6 | B | C |
| 7 | B | D |
| 8 | A | |
| 9 | B | |
| 10 | A | A |
| 11 | A | C |
| 12 | A | C |
| 13 | A | C |
| 14 | B | D |
| 15 | A | C |
| 16 | A | C |
| 17 | B | |
| 18 | B | C |
| 19 | A | B |
| 20 | B | |
| 21 | A | C |
| 22 | A | A |
| 23 | A | C |
| 24 | A | C |
| 25 | A | C |
| 26 | B | |
| 27 | A | |
| 28 | B | |
| 29 | A | C |
| 30 | A | C |
| 31 | A | C |
| 32 | A | C |
| 33 | A | C |
| 34 | A | A |
| 35 | A | B |
| 36 | B | |
| 37 | A | |
| 38 | B | |
| 39 | B | C |
| 40 | A | B |
| 41 | B | |
| 42 | A | B |
| 43 | A | C |
| 44 | A | A |
| 45 | A | C |
| 46 | A | B |
| 47 | A | C |
| 48 | A | C |
| 49 | A | C |
| 50 | B | |
| 51 | A | A |
| 52 | A | C |
| 53 | B | |
| 54 | B | |
| 55 | A | B |
| 56 | A | B |
| 57 | A | B |
| 58 | A | C |

TABLE 7-continued

| Example | hP2X$_3$ | hP2X$_{2/3}$ |
|---|---|---|
| 59 | A | B |
| 60 | A | B |
| 61 | A | B |
| 62 | A | B |
| 63 | B | |
| 64 | A | C |
| 65 | A | B |
| 66 | A | B |
| 67 | B | |
| 68 | A | B |
| 69 | A | A |
| 70 | A | A |
| 71 | B | |
| 72 | A | C |
| 73 | B | |
| 74 | A | B |
| 75 | A | C |
| 76 | B | C |
| 77 | A | C |
| 77 | B | C |
| 78 | B | |
| 79 | B | C |
| 80 | A | C |
| 81 | A | B |
| 82 | A | C |
| 83 | A | C |
| 84 | A | C |
| 85 | A | B |
| 86 | A | A |
| 88 | A | C |
| 89 | A | B |
| 90 | A | C |
| 91 | A | C |
| 93 | A | C |
| 94 | A | C |
| 95 | B | |
| 96 | A | D |
| 97 | A | |
| 98 | A | C |
| 99 | A | C |
| 100 | A | C |
| 101 | B | C |
| 102 | A | D |
| 103 | A | D |
| 104 | A | D |
| 105 | A | C |
| 106 | A | C |
| 107 | A | |
| 108 | A | C |
| 109 | B | |
| 110 | A | A |
| 111 | A | A |
| 112 | A | A |
| 113 | A | C |
| 114 | A | A |
| 115 | A | B |
| 116 | A | A |
| 117 | A | C |
| 118 | A | C |
| 119 | A | C |
| 120 | B | |
| 121 | A | B |
| 122 | A | B |
| 123 | A | C |
| 123 | A | B |
| 124 | A | C |
| 125 | A | C |
| 126 | A | C |
| 127 | A | C |

A: IC$_{50}$ = 1-100 nM
B: IC$_{50}$ = >100-1000 nM
C: IC$_{50}$ = >1000-10,000 nM
D: IC$_{50}$ > 10,000 nM

Example 129: In Vivo Thermal Hyperalgesia (Hargreaves Test) Studies in the Rat

Male Sprague Dawley rats of young adult age group and body weight range of 180-200 g were included in the study. Animals were housed under a 12 h light/dark cycle with food and water ad libitum. The animals underwent acclimatization with the observation chambers of the Hargreaves' apparatus for two days, twice daily for 45-60 min each time prior to initiation of study. Animals were also habituated to the apparatus for 15-30 min before each testing. Thermal hyperalgesia was assessed using the rat plantar test (Ugo Basile, Italy) following a modified method of Hargreaves (1988), "A new and sensitive method for measuring thermal nociception in cutaneous hyperalgesia", Pain 32: 77-88, the entire disclosure of which is herein incorporated by reference.

For measurement of paw withdrawal latency (PWL) values the rats were exposed to a mobile infrared heat source applied directly below the plantar surface of the rat hind paw. The PWL was defined as the time in seconds taken by the rat to remove its hind paw from the heat source. Thirty three percent IR of the instrument was used to measure PWL. Animals showing basal response between 8-14 sec on an untreated paw were included in the study. A cut off point of 20 sec was used to prevent tissue damage.

Following basal readout of PWL values to the thermal stimulus (PWL measurements described previously), 50 µL of complete Freund's Adjuvant (CFA—1 mg/mL suspension—Sigma, USA, Cat # F5881) was injected subcutaneously into the plantar surface of the right hind (ipsilateral) paw of animals under light isoflurane anesthesia. A one mL syringe and 26 g$^{1/2}$-inch needle was used for the injection. CFA suspension was mixed thoroughly before each injection. Light pressure was applied to the injection site for 10 s immediately after the needle was removed from the paw to prevent any leaking out of adjuvant oil from the injection site. The rats were then returned to their housing to recover and kept in soft bedding.

Next day (day 1) after 20-22 h of CFA injection, PWL of animals were recorded. Mean of three readings are taken as PWL recording of ipsilateral paw of each animal for pre and post CFA basal readout. Animals with PWL values of ≤6 sec on day 1 post CFA injection were considered hyperalgesic and selected for randomization into treatment groups and further test sessions following a single blind protocol.

In the test session, PWL was assessed at 1 h post oral dosing of CE test article, vehicle (20% polyethylene glycol, 1% Tween™ 80, 79% water) and naproxen (positive control).

Statistical analysis was done with One-way ANOVA followed by Dunnett's multiple comparison post-test. Post treatment PWL values were compared with pre-treatment PWL values and p<0.05 was considered statistically significant. Each group was typically comprised of 8 animals.

Compounds of the present disclosure were found to be efficacious in this thermal hyperalgesia pain model. The compound of Example 19 was found to provide 36% reversal (p<0.01) to pre-treatment PWL value at 1 hour following a dose of 60 mg/kg po. The compound of Example 10 was found to provide 32% reversal (p<0.01) to pre-treatment PWL value at 1 hour following a dose of 30 mg/kg po.

Example 130: Formalin Induced Pain (Automated Nociception Analyzer Test) in the Rat Male Sprague Dawley rats of young adult age group and body weight range of 200-250 g are included in the study.

Animals are housed under a 12 h light/dark cycle with food and water ad libitum. Animals are acclimatized in the observation chambers of Automated Nociception Analyzer (ANA) for 45-60 min, twice daily for two days prior to the study day. On the day of the study, metal bands are glued to the plantar surface of the right hind paw of each animal enrolled in the study set and kept in plastic observation chambers for 10-15 min. Formalin injection is done in the animals after 0.5 or 1 h of oral treatment with a compound of formula (I) in 20% polyethylene glycol, 1% Tween™ 80 reagent, 79% water (the "test article") or vehicle (20% polyethylene glycol, 1% Tween™ 80 reagent, 79% water). Formalin injection of the animals is done with 50 µL of 2.5% formalin (freshly prepared from formaldehyde solution, Sigma, USA, Cat # F8775) injected subcutaneously in to the dorsum of right hind paw. Animals are placed back to their respective recording chambers of ANA immediately after injection. Flinch count data for each animal is recorded from 1 to 60 min post formalin injection, using ANA motion analysis software. The study is analyzed in 2 phases, the early phase extended from 0-10 min and second phase extended from 11-60 min post formalin injection. The data is collected in 5 min time bins and the counts of each bin are added up for total count of the phase.

Statistical analysis is done with unpaired t test. Comparison is done between total count of treatment groups and vehicle group and p<0.05 is considered statistically significant. Eight animals are typically used in each of test article and vehicle treated groups.

Example 131: Acetic Acid Induced Writhing Test in Mice

Swiss albino mice of 30-40 g are included in the study. The mice are given an intraperitoneal injection of 0.7% v/v acetic acid solution at an injection volume of 10 mL/kg, 30 min after oral administration of a compound of formula (I) (the "test article") or vehicle. The test articles are administered at doses between 20 and 60 mg/kg. The mice are placed individually into glass chambers. The number of writhes produced in these animals is counted for 15 min following acetic acid administration. For scoring purposes writhing is indicated by stretching of the abdomen with simultaneous stretching of at least one hind limb.

Statistical analysis is done with One-way ANOVA followed by Dunnett's multiple comparison tests. Comparison is done between treatment groups and vehicle with respect to total number of writhes and p<0.05 is considered statistically significant. Each group is typically comprised of 6 animals.

Example X: Citric Acid Induced Cough in the Guinea Pig

Compounds of formula (I) are tested for their ability to suppress cough by using the guinea pig model of citric acid induced cough [Kamei, Takahashi, Yoshikawa, and Saitoh, Eur J Pharmacol 528, p 158-161 (2005); Kamei and Takahashi, Eur J Pharmacol 547, p 160-164, (2006); Lewis et al., Pulm Pharmacol Ther. 20, p 315-333 (2007); Leung et al., Cough 3, p 10-14 (2007), the entire disclosures of which are herein incorporated by reference]. In this model, guinea pigs are administered a compound of formula (I) (the "test article") or vehicle, orally or by intraperitoneal injection, 30 to 60 minutes before the cough assessment. The test article is administered at doses ranging from 1 mg/kg to 100 mg/kg. For the cough assessment, animals are exposed to 0.4 M citric acid aerosol inhalation for 10 minutes, and the cough response is recorded as the number of coughs per 10 minutes, as determined by an experienced investigational observer and/or by microphone. In a variation of this model, the animals are sensitized by treatment with inhaled histamine or alpha, beta-methylene ATP prior to the inhaled citric acid treatment.

All publications cited in this specification are incorporated herein by reference. While the present disclosure has been described with reference to particular embodiments, it will be appreciated that modifications can be made without departing from the spirit of the present disclosure. Such modifications are intended to fall within the scope of the appended claims.

What is claimed is:
1. A compound of the structure of formula (I):

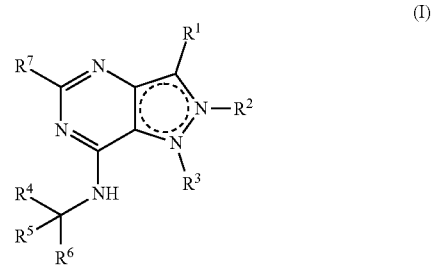

and prodrugs, enantiomers or pharmaceutically acceptable salts thereof, wherein:
$R^1$ is H, halogen, $C_1$-$C_6$ alkyl, $C_3$-$C_6$ cycloalkyl, CN or $CONH_2$;
$R^2$ is none, optionally substituted $C_1$-$C_6$ alkyl or aryl;
$R^3$ is substituted $C_1$-$C_6$ alkyl, $C_3$-$C_6$ cycloalkyl or heterocycle;
$R^4$ is optionally substituted heteroaryl, optionally substituted $C_1$-$C_6$ alkyl, optionally substituted $C_3$-$C_6$ cycloalkyl or optionally substituted aryl;
$R^5$, $R^6$ are independently H, $C_1$-$C_6$ alkyl or $C_3$-$C_6$ cycloalkyl; and
$R^7$ is optionally substituted piperazine, optionally substituted pyridine, optionally substituted pyridazine, optionally substituted pyrazole, optionally substituted triazole, optionally substituted tetrazole, optionally substituted pyrazole, substituted morpholine, or $CONHR^8$, wherein $R^8$ is H, alkyl or cycloalkyl.

2. The compound according to claim 1, wherein $R^1$ is H.
3. The compound according to claim 1, wherein $R^2$ is optionally substituted $C_1$-$C_6$ alkyl.
4. The compound according to claim 1, wherein $R^1$ is halogen, $C_1$-$C_6$ alkyl, or CN.
5. The compound according to claim 1, wherein $R^7$ is selected from the group consisting of:

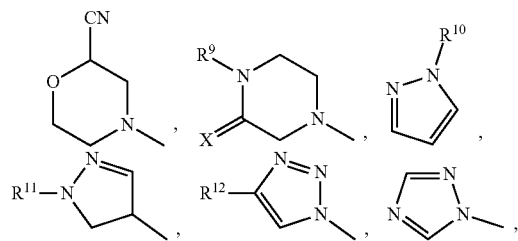

-continued

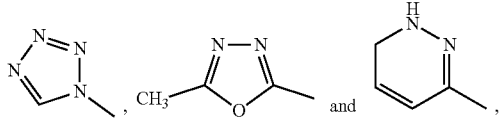

wherein: X is O or H$_2$ in a CH$_2$ group;
R$^9$ is H, optionally substituted C$_1$-C$_6$ alkyl, CO(C$_1$-C$_6$ alkyl), CONH$_2$, C(NH)NH$_2$, C(N—CN)NH$_2$ or SO$_2$NH$_2$;
R$^{10}$ is H or alkyl optionally substituted with —OH;
R$^{11}$ is H, CH$_2$—CONH$_2$ or alkyl optionally substituted with —OH or halogen; and
R$^{12}$ is H or CONH$_2$.

6. The compound according to claim 1, wherein R$^4$ is optionally substituted heteroaryl.

7. The compound according to claim 1, wherein R$^4$ is optionally substituted aryl.

8. The compound according to claim 1, wherein R$^5$ and R$^6$ are independently H or C$_1$-C$_6$ alkyl or C$_3$-C$_6$ cycloalkyl.

9. The compound according to claim 1, wherein R$^5$ and R$^6$ are independently H or C$_3$-C$_6$ cycloalkyl.

10. The compound according to claim 1, wherein R$^1$ is H and R$^2$ is optionally substituted C$_1$-C$_6$ alkyl.

11. The compound according to claim 1, wherein R$^1$ is H, R$^2$ is optionally substituted C$_1$-C$_6$ alkyl and R$^4$ is optionally substituted heteroaryl.

12. The compound according to claim 1, wherein R$^1$ is H, R$^2$ is optionally substituted C$_1$-C$_6$ alkyl, R$^4$ is optionally substituted heteroaryl, R$^5$ and R$^6$ are independently H or C$_1$-C$_6$ alkyl or are independently H and C$_3$-C$_6$ cycloalkyl, and R$^7$ is

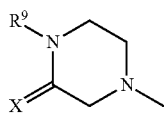

wherein X is H$_2$ in a CH$_2$ group and R$^9$ is CONH$_2$.

13. The compound according to claim 1, wherein R$^4$ is an optionally substituted heteroaryl selected from the group consisting of quinoline, benzofuran, pyridine, benzothiophene, imidazopyridine and indazole.

14. A compound which is selected from the group consisting of:
- 1-{4-[2-Isopropyl-7-((R)-1-quinolin-3-yl-ethylamino)-2H-pyrazolo[4,3-d]pyrimidin-5-yl]-piperazin-1-yl}-ethanone;
- 1-{4-[2-Isopropyl-7-(1-quinolin-3-yl-ethylamino)-2H-pyrazolo[4,3-d]pyrimidin-5-yl]-piperazin-1-yl}-ethanone;
- 1-(4-{7-[2-(4-Chloro-phenyl)-1,1-dimethyl-ethylamino]-2-isopropyl-2H-pyrazolo[4,3-d]pyrimidin-5-yl}-piperazin-1-yl)-ethanone;
- 1-{4-[2-sec-Butyl-7-(1-quinolin-3-yl-ethylamino)-2H-pyrazolo[4,3-d]pyrimidin-5-yl]-piperazin-1-yl}-ethanone;
- 1-{4-[2-sec-Butyl-7-((R)-1-quinolin-3-yl-ethylamino)-2H-pyrazolo[4,3-d]pyrimidin-5-yl]-piperazin-1-yl}-ethanone;
- 1-(4-{2-sec-Butyl-7-[2-(4-chloro-phenyl)-1,1-dimethyl-ethylamino]-2H-pyrazolo[4,3-d]pyrimidin-5-yl}-piperazin-1-yl)-ethanone;
- 1-{4-[2-Isobutyl-7-((R)-1-quinolin-3-yl-ethylamino)-2H-pyrazolo[4,3-d]pyrimidin-5-yl]-piperazin-1-yl}-ethanone;
- 1-{4-[2-(1-Ethyl-propyl)-7-((R)-1-quinolin-3-yl-ethylamino)-2H-pyrazolo[4,3-d]pyrimidin-5-yl]-piperazin-1-yl}-ethanone;
- 1-{4-[2-Phenyl-7-((R)-1-quinolin-3-yl-ethylamino)-2H-pyrazolo[4,3-d]pyrimidin-5-yl]-piperazin-1-yl}-ethanone;
- 4-{1-sec-Butyl-7-[((R)-cyclopropyl-quinolin-3-yl-methyl)-amino]-1H-pyrazolo[4,3-d]pyrimidin-5-yl}-piperazine-1-carboxylic acid amide;
- 1-{4-[1-Isopropyl-4-(1-quinolin-3-yl-ethylamino)-1H-pyrazolo[3,4-d]pyrimidin-6-yl]-piperazin-1-yl}-ethanone;
- 1-{4-[1-Isopropyl-7-((R)-1-quinolin-3-yl-ethylamino)-1H-pyrazolo[4,3-d]pyrimidin-5-yl]-piperazin-1-yl}-ethanone;
- 1-(4-{7-[2-(4-Chloro-phenyl)-1,1-dimethyl-ethylamino]-1-isopropyl-1H-pyrazolo[4,3-d]pyrimidin-5-yl}-piperazin-1-yl)-ethanone;
- 1-(4-{1-Isopropyl-7-[(quinolin-3-ylmethyl)-amino]-1H-pyrazolo[4,3-d]pyrimidin-5-yl}-piperazin-1-yl)-ethanone;
- 4-[1-Isopropyl-7-((R)-1-quinolin-3-yl-ethylamino)-1H-pyrazolo[4,3-d]pyrimidin-5-yl]-1-methyl-piperazin-2-one;
- 1-{4-[1-Isobutyl-7-((R)-1-quinolin-3-yl-ethylamino)-1H-pyrazolo[4,3-d]pyrimidin-5-yl]-piperazin-1-yl}-ethanone;
- 1-{4-[1-Isopropyl-7-((S)-1-quinolin-3-yl-ethylamino)-2H-pyrazolo[4,3-d]pyrimidin-5-yl]-piperazin-1-yl}-ethanone;
- 1-{4-[1-sec-Butyl-7-((S)-1-quinolin-3-yl-ethylamino)-1H-pyrazolo[4,3-d]pyrimidin-5-yl]-piperazin-1-yl}-ethanone;
- 1-{4-[1-((S)-sec-Butyl)-7-((R)-1-quinolin-3-yl-ethylamino)-1H-pyrazolo[4,3-d]pyrimidin-5-yl]-piperazin-1-yl}-ethanone;
- 4-[1-sec-Butyl-7-((R)-1-quinolin-3-yl-ethylamino)-1H-pyrazolo[4,3-d]pyrimidin-5-yl]-1-methyl-piperazin-2-one;
- 1-{4-[1-((R)-sec-Butyl)-7-((R)-1-quinolin-3-yl-ethylamino)-1H-pyrazolo[4,3-d]pyrimidin-5-yl]-piperazin-1-yl}-ethanone;
- 1-{4-[1-(1-Ethyl-propyl)-7-((R)-1-quinolin-3-yl-ethylamino)-1H-pyrazolo[4,3-d]pyrimidin-5-yl]-piperazin-1-yl}-ethanone;
- 1-Ethyl-4-[1-isopropyl-7-((R)-1-quinolin-3-yl-ethylamino)-1H-pyrazolo[4,3-d]pyrimidin-5-yl]-piperazin-2-one;
- 1-{4-[1-(2-Methoxy-1-methyl-ethyl)-7-((R)-1-quinolin-3-yl-ethylamino)-1H-pyrazolo[4,3-d]pyrimidin-5-yl]-piperazin-1-yl}-ethanone;
- 1-{4-[1-Cyclopentyl-7-((R)-1-quinolin-3-yl-ethylamino)-1H-pyrazolo[4,3-d]pyrimidin-5-yl]-piperazin-1-yl}-ethanone;
- 1-{4-[7-((R)-1-Quinolin-3-yl-ethylamino)-1-(tetrahydropyran-4-ylmethyl)-1H-pyrazolo[4,3-d]pyrimidin-5-yl]-piperazin-1-yl}-ethanone;
- 1-{4-[7-((R)-1-Quinolin-3-yl-ethylamino)-1-(tetrahydropyran-4-yl)-1H-pyrazolo[4,3-d]pyrimidin-5-yl]-piperazin-1-yl}-ethanone;
- 1-{4-[1-Hexyl-7-((R)-1-quinolin-3-yl-ethylamino)-1H-pyrazolo[4,3-d]pyrimidin-5-yl]-piperazin-1-yl}-ethanone;

1-{4-[7-{[1-(4-Chloro-phenyl)-cyclobutylmethyl]-amino}-1-(1-ethyl-propyl)-1H-pyrazolo[4,3-d]pyrimidin-5-yl]-piperazin-1-yl}-ethanone;
1-{4-[7-[1-(4-Ethoxy-phenyl)-ethylamino]-1-(1-ethyl-propyl)-1H-pyrazolo[4,3-d]pyrimidin-5-yl]-piperazin-1-yl}-ethanone;
1-[4-(1-sec-Butyl-7-{[1-(4-chloro-phenyl)-cyclobutylmethyl]-amino}-1H-pyrazolo[4,3-d]pyrimidin-5-yl)-piperazin-1-yl]-ethanone;
1-{4-[1-Cyclobutylmethyl-7-((R)-1-quinolin-3-yl-ethylamino)-1H-pyrazolo[4,3-d]pyrimidin-5-yl]-piperazin-1-yl}-ethanone;
1-{4-[7-[(S)-1-(4-Ethoxy-phenyl)-ethylamino]-1-(1-ethyl-propyl)-1H-pyrazolo[4,3-d]pyrimidin-5-yl]-piperazin-1-yl}-ethanone;
1-{4-[1-Dicyclopropylmethyl-7-((R)-1-quinolin-3-yl-ethylamino)-1H-pyrazolo[4,3-d]pyrimidin-5-yl]-piperazin-1-yl}-ethanone;
1-{4-[1-(1-Ethyl-propyl)-7-((R)-1-quinolin-3-yl-propylamino)-1H-pyrazolo[4,3-d]pyrimidin-5-yl]-piperazin-1-yl}-ethanone;
1-{4-[1-(1-Ethyl-propyl)-7-((S)-1-quinolin-3-yl-propylamino)-1H-pyrazolo[4,3-d]pyrimidin-5-yl]-piperazin-1-yl}-ethanone;
1-{4-[1-Isopropyl-7-((R)-1-quinolin-3-yl-ethylamino)-1H-pyrazolo[4,3-d]pyrimidin-5-yl]-piperazin-1-yl}-propan-1-one;
1-{4-[1-sec-Butyl-7-((R)-1-quinolin-3-yl-ethylamino)-1H-pyrazolo[4,3-d]pyrimidin-5-yl]-piperazin-1-yl}-propan-1-one;
1-{4-[7-(1-Benzofuran-5-yl-ethylamino)-1-(1-ethyl-propyl)-1H-pyrazolo[4,3-d]pyrimidin-5-yl]-piperazin-1-yl}-ethanone;
1-{4-[1-(1-Ethyl-propyl)-7-((R)-1-naphthalen-2-yl-ethylamino)-1H-pyrazolo[4,3-d]pyrimidin-5-yl]-piperazin-1-yl}-ethanone;
4-[1-Isopropyl-7-((R)-1-quinolin-3-yl-ethylamino)-1H-pyrazolo[4,3-d]pyrimidin-5-yl]-piperazin-2-one;
1-(4-{1-(1-Ethyl-propyl)-7-[1-(6-fluoro-quinolin-3-yl)-ethylamino]-1H-pyrazolo[4,3-d]pyrimidin-5-yl}-piperazin-1-yl)-ethanone;
1-{4-[1-sec-Butyl-7-((R)-1-quinolin-3-yl-propylamino)-1H-pyrazolo[4,3-d]pyrimidin-5-yl]-piperazin-1-yl}-ethanone;
1-{4-[7-[((R)-Cyclopropyl-quinolin-3-yl-methyl)-amino]-1-(1-ethyl-propyl)-1H-pyrazolo[4,3-d]pyrimidin-5-yl]-piperazin-1-yl}-ethanone;
1-(4-{1-sec-Butyl-7-[1-(2-methyl-benzofuran-5-yl)-ethylamino]-1H-pyrazolo[4,3-d]pyrimidin-5-yl}-piperazin4.6-1-yl)-ethanone;
1-(4-{1-(1-Ethyl-propyl)-7-[1-(2-methyl-benzofuran-5-yl)-ethylamino]-1H-pyrazolo[4,3-d]pyrimidin-5-yl}-piperazin-1-yl)-ethanone;
1-(4-{1-(1-Ethyl-propyl)-7-[1-(4-isopropoxy-phenyl)-ethylamino]-1H-pyrazolo[4,3-d]pyrimidin-5-yl}-piperazin-1-yl)-ethanone;
1-{4-[1-Cyclobutyl-7-((R)-1-quinolin-3-yl-ethylamino)-1H-pyrazolo[4,3-d]pyrimidin-5-yl]-piperazin-1-yl}-ethanone;
4-[1-Cyclobutyl-7-((R)-1-quinolin-3-yl-ethylamino)-1H-pyrazolo[4,3-d]pyrimidin-5-yl]-1-methyl-piperazin-2-one;
1-{4-[1-Ethyl-7-((R)-1-quinolin-3-yl-ethylamino)-1H-pyrazolo[4,3-d]pyrimidin-5-yl]-piperazin-1-yl}-ethanone;
4-[1-(1-Ethyl-propyl)-7-((R)-1-quinolin-3-yl-ethylamino)-1H-pyrazolo[4,3-d]pyrimidin-5-yl]-piperazine-1-carboxylic acid amide;
1-(4-{1-sec-Butyl-7-[1-(6-phenyl-pyridin-3-yl)-ethylamino]-1H-pyrazolo[4,3-d]pyrimidin-5-yl}-piperazin-1-yl)-ethanone;
1-(4-{1-sec-Butyl-7-[1-(4-pyridin-2-yl-phenyl)-ethylamino]-1H-pyrazolo[4,3-d]pyrimidin-5-yl}-piperazin-1-yl)-ethanone;
1-(4-{1-(1-Ethyl-propyl)-7-[(R)-1-(6-fluoro-quinolin-3-yl)-ethylamino]-1H-pyrazolo[4,3-d]pyrimidin-5-yl}-piperazin-1-yl)-ethanone;
1-{4-[7-[1-(2-Cyclopropyl-benzofuran-5-yl)-ethylamino]-1-(1-ethyl-propyl)-1H-pyrazolo[4,3-d]pyrimidin-5-yl]-piperazin-1-yl}-ethanone;
1-(4-{1-sec-Butyl-7-[((R)-cyclopropyl-quinolin-3-yl-methyl)-amino]-1H-pyrazolo[4,3-d]pyrimidin-5-yl}-piperazin-1-yl)-ethanone;
1-{4-[7-(1-Benzo[b]thiophen-5-yl-ethylamino)-1-(1-ethyl-propyl)-1H-pyrazolo[4,3-d]pyrimidin-5-yl]-piperazin-1-yl}-ethanone;
1-[4-(1-sec-Butyl-7-{[cyclopropyl-(6-phenyl-pyridin-3-yl)-methyl]-amino}-1H-pyrazolo[4,3-d]pyrimidin-5-yl)-piperazin-1-yl]-ethanone;
4-{7-[((R)-Cyclopropyl-quinolin-3-yl-methyl)-amino]-1-isopropyl-1H-pyrazolo[4,3-d]pyrimidin-5-yl}-1-methyl-piperazin-2-one;
1-{4-[1-(1,2-Dimethyl-propyl)-7-((R)-1-quinolin-3-yl-ethylamino)-1H-pyrazolo[4,3-d]pyrimidin-5-yl]-piperazin-1-yl}-ethanone;
1-(4-{1-(1-Ethyl-propyl)-7-[(R)-1-(6-fluoro-quinolin-3-yl)-ethylamino]-1H-pyrazolo[4,3-d]pyrimidin-5-yl}-piperazin-1-yl)-ethanone
1-{4-[7-[((R)-Cyclopropyl-quinolin-3-yl-methyl)-amino]-1-(1,2-dimethyl-propyl)-1H-pyrazolo[4,3-d]pyrimidin-5-yl]-piperazin-1-yl}-ethanone;
1-{4-[7-{[Cyclopropyl-(6-cyclopropylmethoxy-pyridin-3-yl)-methyl]-amino}-1-(1-ethyl-propyl)-1H-pyrazolo[4,3-d]pyrimidin-5-yl]-piperazin-1-yl}-ethanone;
4-{1-(1-Ethyl-propyl)-7-[(quinolin-3-ylmethyl)-amino]-1H-pyrazolo[4,3-d]pyrimidin-5-yl}-piperazine-1-carboxylic acid amide;
1-{4-[7-{[Cyclopropyl-(6-fluoro-quinolin-3-yl)-methyl]-amino}-1-(1-ethyl-propyl)-1H-pyrazolo[4,3-d]pyrimidin-5-yl]-piperazin-1-yl}-ethanone;
4-{7-[((R)-Cyclopropyl-quinolin-3-yl-methyl)-amino]-1-isopropyl-1H-pyrazolo[4,3-d]pyrimidin-5-yl}-piperazine-1-carboxylic acid amide;
4-{1-((S)-sec-Butyl)-7-[(cyclopropyl-imidazo[1,2-a]pyridin-6-yl-methyl)-amino]-1H-pyrazolo[4,3-d]pyrimidin-5-yl}-piperazine-1-carboxylic acid amide;
4-{1-((S)-sec-Butyl)-7-[1-(6,7-difluoro-quinolin-3-yl)-ethylamino]-1H-pyrazolo[4,3-d]pyrimidin-5-yl}-piperazine-1-carboxylic acid amide;
4-{1-((S)-sec-Butyl)-7-[((R)-cyclopropyl-quinolin-3-yl-methyl)-amino]-1H-pyrazolo[4,3-d]pyrimidin-5-yl}-piperazine-1-carboxylic acid amide;
4-{1-((R)-sec-Butyl)-7-[((R)-cyclopropyl-quinolin-3-yl-methyl)-amino]-1H-pyrazolo[4,3-d]pyrimidin-5-yl}-piperazine-1-carboxylic acid amide;
4-{1-((S)-sec-Butyl)-7-[1-(1H-indazol-3-yl)-ethylamino]-1H-pyrazolo[4,3-d]pyrimidin-5-yl}-piperazine-1-carboxylic acid amide;
4-{7-[((R)-Cyclopropyl-quinolin-3-yl-methyl)-amino]-1-(tetrahydro-pyran-4-yl)-1H-pyrazolo[4,3-d]pyrimidin-5-yl}-piperazine-1-carboxylic acid amide;

4-[1-((S)-sec-Butyl)-7-(1-pyrazolo[1,5-a]pyridin-2-yl-ethylamino)-1H-pyrazolo[4,3-d]pyrimidin-5-yl]-piperazine-1-carboxylic acid amide;

((R)-Cyclopropyl-quinolin-3-yl-methyl)-[1-(1-ethyl-propyl)-5-[1,2,3]triazol-1-yl-1H-pyrazolo[4,3-d]pyrimidin-7-yl]-amine;

1-{1-sec-Butyl-7-[((R)-cyclopropyl-quinolin-3-yl-methyl)-amino]-1H-pyrazolo[4,3-d]pyrimidin-5-yl}-piperidine-4-carboxylic acid amide;

4-{1-sec-Butyl-7-[((R)-cyclopropyl-quinolin-3-yl-methyl)-amino]-1H-pyrazolo[4,3-d]pyrimidin-5-yl}-morpholine-2-carbonitrile;

1-{4-[1-sec-Butyl-3-methyl-7-((R)-1-quinolin-3-yl-ethylamino)-1H-pyrazolo[4,3-d]pyrimidin-5-yl]-piperazin-1-yl}-ethanone;

(1-sec-Butyl-5-[1,2,4]triazol-1-yl-1H-pyrazolo[4,3-d]pyrimidin-7-yl)-((R)-cyclopropyl-quinolin-3-yl-methyl)-amine;

(1-sec-Butyl-5-tetrazol-1-yl-1H-pyrazolo[4,3-d]pyrimidin-7-yl)-((R)-cyclopropyl-quinolin-3-yl-methyl)-amine;

(1-sec-Butyl-5-tetrazol-2-yl-1H-pyrazolo[4,3-d]pyrimidin-7-yl)-((R)-cyclopropyl-quinolin-3-yl-methyl)-amine;

4-(1-((S)-sec-Butyl)-7-{[cyclopropyl-(1-ethyl-1H-indazol-5-yl)-methyl]-amino}-1H-pyrazolo[4,3-d]pyrimidin-5-yl)-piperazine-1-carboxylic acidamide;

1-{4-[1-((S)-sec-Butyl)-7-(2-hydroxy-1-quinolin-3-yl-ethylamino)-1H-pyrazolo[4,3-d]pyrimidin-5-yl]-piperazin-1-yl}-ethanone;

1-{4-[1-((S)-sec-Butyl)-7-(2-methoxy-1-quinolin-3-yl-ethylamino)-1H-pyrazolo[4,3-d]pyrimidin-5-yl]-piperazin-1-yl}-ethanone;

4-{1-((S)-sec-Butyl)-7-[(cyclopropyl-quinoxalin-2-yl-methyl)-amino]-1H-pyrazolo[4,3-d]pyrimidin-5-yl}-piperazine-1-carboxylic acid amide;

4-{1-sec-Butyl-7-[(R)-1-(7-methyl-imidazo[1,2-a]pyridin-2-yl)-ethylamino]-1H-pyrazolo[4,3-d]pyrimidin-5-yl}-piperazine-1-carboxylic acid amide;

4-[1-sec-Butyl-7-((R)-1-quinolin-3-yl-ethylamino)-1H-pyrazolo[4,3-d]pyrimidin-5-yl]-piperazine-1-carboxylic acid amide;

4-{1-(1-Cyclopropyl-ethyl)-7-[((R)-cyclopropyl-quinolin-3-yl-methyl)-amino]-1H-pyrazolo[4,3-d]pyrimidin-5-yl}-piperazine-1-carboxylic acid amide;

1-sec-Butyl-7-[((R)-cyclopropyl-quinolin-3-yl-methyl)-amino]-1H-pyrazolo[4,3-d]pyrimidine-5-carboxylic acid amide;

1-{4-[1-sec-Butyl-7-((R)-1-quinolin-3-yl-ethylamino)-2H-pyrazolo[4,3-d]pyrimidin-5-yl]-piperazin-1-yl}-ethanone;

1-{4-[3-Bromo-1-sec-butyl-7-((R)-1-quinolin-3-yl-ethylamino)-1H-pyrazolo[4,3-d]pyrimidin-5-yl]-piperazin-1-yl}-ethanone;

5-(4-Acetyl-piperazin-1-yl)-1-sec-butyl-7-((R)-1-quinolin-3-yl-ethylamino)-1H-pyrazolo[4,3-d]pyrimidine-3-carbonitrile;

1-{4-[1-sec-Butyl-3-cyclopropyl-7-((R)-1-quinolin-3-yl-ethylamino)-1H-pyrazolo[4,3-d]pyrimidin-5-yl]-piperazin-1-yl}-ethanone;

1-{4-[3-Bromo-2-isopropyl-7-(1-quinolin-3-yl-ethylamino)-2H-pyrazolo[4,3-d]pyrimidin-5-yl]-piperazin-1-yl}-ethanone;

5-(4-Acetyl-piperazin-1-yl)-2-isopropyl-7-(1-quinolin-3-yl-ethylamino)-2H-pyrazolo[4,3-d]pyrimidine-3-carboxylic acid amide;

1-{4-[2-Isopropyl-3-methyl-7-(1-quinolin-3-yl-ethylamino)-2H-pyrazolo[4,3-d]pyrimidin-5-yl]-piperazin-1-yl}-ethanone;

1-(4-{3-Bromo-7-[2-(4-chloro-phenyl)-1,1-dimethyl-ethylamino]-2-isopropyl-2H-pyrazolo[4,3-d]pyrimidin-5-yl}-piperazin-1-yl)-ethanone;

1-{4-[3-Bromo-2-isopropyl-7-((R)-1-quinolin-3-yl-ethylamino)-2H-pyrazolo[4,3-d]pyrimidin-5-yl]-piperazin-1-yl}-ethanone;

1-{4-[3-Chloro-2-isopropyl-7-((R)-1-quinolin-3-yl-ethylamino)-2H-pyrazolo[4,3-d]pyrimidin-5-yl]-piperazin-1-yl}-ethanone;

1-{4-[3-Bromo-1-isopropyl-7-((R)-1-quinolin-3-yl-ethylamino)-1H-pyrazolo[4,3-d]pyrimidin-5-yl]-piperazin-1-yl}-ethanone;

1-(4-{7-[2-(4-Chloro-phenyl)-1,1-dimethyl-ethylamino]-2-isopropyl-3-methyl-2H-pyrazolo[4,3-d]pyrimidin-5-yl}-piperazin-1-yl)-ethanone;

1-{4-[2-Isopropyl-3-methyl-7-((R)-1-quinolin-3-yl-ethylamino)-2H-pyrazolo[4,3-d]pyrimidin-5-yl]-piperazin-1-yl}-ethanone;

5-(4-Acetyl-piperazin-1-yl)-2-isopropyl-7-((R)-1-quinolin-3-yl-ethylamino)-2H-pyrazolo[4,3-d]pyrimidine-3-carbonitrile;

5-(4-Acetyl-piperazin-1-yl)-1-isopropyl-7-((R)-1-quinolin-3-yl-ethylamino)-1H-pyrazolo[4,3-d]pyrimidine-3-carbonitrile;

1-{4-[3-Bromo-2-sec-butyl-7-((R)-1-quinolin-3-yl-ethylamino)-2H-pyrazolo[4,3-d]pyrimidin-5-yl]-piperazin-1-yl}-ethanone;

5-(4-Acetyl-piperazin-1-yl)-2-sec-butyl-7-((R)-1-quinolin-3-yl-ethylamino)-2H-pyrazolo[4,3-d]pyrimidine-3-carbonitrile;

1-{4-[3-Cyclopropyl-2-isopropyl-7-((R)-1-quinolin-3-yl-ethylamino)-2H-pyrazolo[4,3-d]pyrimidin-5-yl]-piperazin-1-yl}-ethanone;

4-{1-sec-Butyl-7-[((R)-cyclopropyl-quinolin-3-yl-methyl)-amino]-1H-pyrazolo[4,3-d]pyrimidin-5-yl}-piperazine-1-sulfonic acid amide;

2-(4-{1-sec-Butyl-7-[((R)-cyclopropyl-quinolin-3-yl-methyl)-amino]-1H-pyrazolo[4,3-d]pyrimidin-5-yl}-piperazin-1-yl)-acetamide;

4-{1-sec-Butyl-7-[((R)-cyclopropyl-quinolin-3-yl-methyl)-amino]-1H-pyrazolo[4,3-d]pyrimidin-5-yl}-N'-cyanopiperazine-1-carboximidamide;

4-(1-sec-butyl-7-{[(R)-methyl(quinolin-3-yl)methyl]amino}-1H-pyrazolo[4,3-d]pyrimidin-5-yl)-N'-cyano-piperazine-1-carboximidamide;

4-{1-sec-Butyl-7-[((R)-cyclopropyl-quinolin-3-yl-methyl)-amino]-1H-pyrazolo[4,3-d]pyrimidin-5-yl}-piperazine-1-carboxamidine;

2-{4-[1-sec-Butyl-7-((R)-1-quinolin-3-yl-ethylamino)-1H-pyrazolo[4,3-d]pyrimidin-5-yl]-pyrazol-1-yl}-ethanol;

[1-sec-Butyl-5-(1-methyl-1H-pyrazol-4-yl)-1H-pyrazolo[4,3-d]pyrimidin-7-yl]-((R)-cyclopropyl-quinolin-3-yl-methyl)-amine;

[1-sec-Butyl-5-(1-ethyl-1H-pyrazol-4-yl)-1H-pyrazolo[4,3-d]pyrimidin-7-yl]-((R)-cyclopropyl-quinolin-3-yl-methyl)-amine;

{1-sec-Butyl-5-[1-(2-fluoro-ethyl)-1H-pyrazol-4-yl]-1H-pyrazolo[4,3-d]pyrimidin-7-yl}-((R)-cyclopropyl-quinolin-3-yl-methyl)-amine;

(R)-Cyclopropyl-quinolin-3-yl-methyl)-[5-(1-methyl-1H-pyrazol-4-yl)-1-(tetrahydro-pyran-4-yl)-1H-pyrazolo[4,3-d]pyrimidin-7-yl]-amine;

4-{1-sec-Butyl-7-[((R)-cyclopropyl-quinolin-3-yl-methyl)-amino]-1H-pyrazolo[4,3-d]pyrimidin-5-yl}-piperidine-1-carboxylic acid amide;

[1-sec-Butyl-5-(1H-pyrazol-4-yl)-1H-pyrazolo[4,3-d]pyrimidin-7-yl]-((R)-cyclopropyl-quinolin-3-yl-methyl)-amine;

2-(4-{1-sec-Butyl-7-[((R)-cyclopropyl-quinolin-3-yl-methyl)-amino]-1H-pyrazolo[4,3-d]pyrimidin-5-yl}-pyrazol-1-yl)-acetamide;

2-(4-{1-sec-Butyl-7-[((R)-cyclopropyl-quinolin-3-yl-methyl)-amino]-1H-pyrazolo[4,3-d]pyrimidin-5-yl}-pyrazol-1-yl)-ethanol;

2-{1-((S)-sec-Butyl)-5-[1-(2-fluoro-ethyl)-1H-pyrazol-4-yl]-1H-pyrazolo[4,3-d]pyrimidin-7-ylamino}-2-quinolin-3-yl-ethanol;

{1-sec-Butyl-5-[1-(2-fluoro-ethyl)-1H-pyrazol-4-yl]-1H-pyrazolo[4,3-d]pyrimidin-7-yl}-[(R)-1-(7-methyl-imidazo[1,2-a]pyridin-2-yl)-ethyl]-amine;

4-[1-((S)-sec-Butyl)-7-(2-hydroxy-1-quinolin-3-yl-ethyl-amino)-1H-pyrazolo[4,3-d]pyrimidin-5-yl]-piperazine-1-carboxylic acid amide;

1-sec-Butyl-7-[((R)-cyclopropyl-quinolin-3-yl-methyl)-amino]-1H-pyrazolo[4,3-d]pyrimidine-5-carboxylic acid cyclopropylamide;

[1-sec-Butyl-5-(5-methyl-[1,3,4]oxadiazol-2-yl)-1H-pyrazolo[4,3-d]pyrimidin-7-yl]-((R)-cyclopropyl-quinolin-3-yl-methyl)-amine;

1-{1-sec-Butyl-7-[((R)-cyclopropyl-quinolin-3-yl-methyl)-amino]-1H-pyrazolo[4,3-d]pyrimidin-5-yl}-1H-[1,2,3]triazole-4-carboxylic acid amide; and (1-sec-Butyl-5-pyridazin-3-yl-1H-pyrazolo[4,3-d]pyrimidin-7-yl)-((R)-cyclopropyl-quinolin-3-yl-methyl)-amine.

15. A pharmaceutical composition comprising a compound of claim 1 and a pharmaceutically acceptable excipient.

16. A kit comprising a compound of claim 1.

17. A kit comprising the pharmaceutical composition of claim 15.

18. A method for regulating one or both of P2X$_3$ or P2X$_{2/3}$ receptors in a subject in need thereof, said method comprising administering a therapeutically effective amount of a compound of claim 1 to the subject.

19. The method according to claim 18, wherein said regulating comprises inhibition of one or both of the P2X$_3$ or P2X$_{2/3}$ receptors.

20. A method for treating pain in a subject, comprising administering a therapeutically effective amount of a compound of claim 1 to said patient.

21. The method of claim 20, wherein the pain is nociceptive, dysfunctional, idiopathic, neuropathic, somatic, central, visceral, inflammatory, or procedural pain.

22. The method of claim 20, wherein the pain is caused by airway, bladder or visceral organ dysfunction.

23. The method of claim 20, wherein the pain is a migraine, back pain, neck pain, gynecological pain, pre-labor pain, labor pain, orthopedic pain, post-stroke pain, post-surgical pain, post herpetic neuralgia, sickle cell crisis, interstitial cystitis, urological pain, dental pain, headache, wound pain, surgical pain, suturing, fracture setting pain, or pain incident to biopsy.

24. The method of claim 20, wherein the pain is due to inflammation, nerve compression, or a mechanical force resulting from tissue distension as a consequence of invasion by a tumor into a tissue.

25. The method of claim 20, wherein the pain is caused by esophageal cancer, colitis, cystitis, irritable bowel syndrome or idiopathic neuropathy.

26. The method of claim 21, wherein the somatic pain comprises pain from bone, joint, muscle, skin or connective tissue.

27. The method of claim 21, wherein the central pain comprises pain from brain trauma, stroke or spinal cord injury.

28. The method of claim 21, wherein the visceral pain comprises pain from the respiratory tract, gastrointestinal tract, pancreas, urinary tract or reproductive organs.

29. The method of claim 21, wherein the dysfunctional pain comprises pain from a rheumatologic condition, tension type headache, irritable bowel disorder or erythermalgia.

30. The method of claim 21, wherein the nociceptive pain comprises pain from a cut, bruise, bone fracture, crush injury, burn, trauma, surgery, labor, sprain, bump, injection, dental procedure, skin biopsy or obstruction.

31. The method of claim 21, wherein the neuropathic pain comprises pain due to trauma, surgery, herniation of an intervertebral disk, spinal cord injury, diabetes, infection with herpes zoster, HIV/AIDS, late-stage cancer, amputation, carpal tunnel syndrome, chronic alcohol use, exposure to radiation, or an unintended side-effect of a neurotoxic treatment agent.

32. The method of claim 21, wherein the inflammatory pain comprises pain due to joint injury, muscle injury, tendon injury, surgical procedures, infection or arthritis.

33. The method of claim 21, wherein the procedural pain comprises pain from a medical, dental or surgical procedure.

34. The method of claim 33, wherein the procedural pain is postoperative pain, associated with an injection, draining an abscess, surgery, dermatological, dental procedure, ophthalmic procedure, arthroscopy or cosmetic surgery.

35. The method of claim 20, wherein the pain is caused by cancer.

36. The method of claim 35, wherein the cancer is bone cancer.

37. The method of claim 20, wherein the administration is oral, intramuscular, rectal, cutaneous, subcutaneous, topical, transdermal, sublingual, nasal, vaginal, epidural, intrathecal, intravesical or ocular.

38. A method for treating a respiratory dysfunction in a subject in need thereof, said method comprising administering a therapeutically effective amount of a compound of claim 1 to the subject.

39. The method of claim 38, wherein the respiratory dysfunction is one or more of bronchial hyperactivity, bronchoconstriction, bronchospasm, hypersecretion, cough, cough hypersensitivity syndrome, wheezing, dyspnea, breathlessness and chest tightness.

40. The method of claim 38, wherein the respiratory dysfunction is caused by idiopathic pulmonary fibrosis (IPF), chronic obstructive pulmonary disease (COPD), asthma, upper respiratory infection, interstitial lung disease (ILD), post-nasal drip, bronchitis, gastroesophageal reflux disease (GERD), treatment with an ACE (Angiotensin Converting Enzyme) inhibitor or smoking.

41. The method of claim 39, wherein the cough is acute cough, sub-acute cough, chronic cough, pathologic cough, or the urge to cough.

42. The method of claim 39, wherein the cough is caused by idiopathic pulmonary fibrosis (IPF), chronic obstructive pulmonary disease (COPD), asthma, upper respiratory infection, interstitial lung disease (ILD), post-nasal drip, bronchitis, gastroesophageal reflux disease (GERD), treatment with an ACE (Angiotensin Converting Enzyme) inhibitor or smoking.

43. The method of claim 38, wherein the administration is oral, intramuscular, rectal, cutaneous, subcutaneous, topical, transdermal, sublingual, nasal, vaginal, epidural, intrathecal, intravesical, ocular or inhalation.

* * * * *